(12) United States Patent
Tsuchiya et al.

(10) Patent No.: US 7,863,042 B2
(45) Date of Patent: Jan. 4, 2011

(54) FUCOSE TRANSPORTER

(75) Inventors: Masayuki Tsuchiya, Shizuoka (JP); Shigeyuki Iijima, Shizuoka (JP); Izumi Sugo, Shizuoka (JP); Yasuo Sekimori, Shizuoka (JP); Kenju Ueno, Shizuoka (JP); Kiyoshi Habu, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 308 days.

(21) Appl. No.: 10/561,191

(22) PCT Filed: Jun. 18, 2004

(86) PCT No.: PCT/JP2004/008956
§ 371 (c)(1),
(2), (4) Date: Dec. 16, 2005

(87) PCT Pub. No.: WO2005/017155
PCT Pub. Date: Feb. 24, 2005

(65) Prior Publication Data
US 2006/0246456 A1    Nov. 2, 2006

(30) Foreign Application Priority Data

| Jun. 18, 2003 | (JP) | 2003-174006 |
| Jun. 18, 2003 | (JP) | 2003-174010 |
| Jul. 29, 2003 | (JP) | 2003-282081 |
| Jul. 29, 2003 | (JP) | 2003-282102 |

(51) Int. Cl.
C07H 17/00 (2006.01)
(52) U.S. Cl. .................... 435/325; 536/23.1; 530/350
(58) Field of Classification Search .................. None
See application file for complete search history.

(56) References Cited

U.S. PATENT DOCUMENTS

| 4,748,116 A | 5/1988 | Simonsson et al. | |
| 2002/0197679 A1 | 12/2002 | Tang et al. | |
| 2003/0017480 A1 | 1/2003 | Ota et al. | |
| 2003/0068311 A1 | 4/2003 | Lasek et al. | |
| 2003/0082776 A1 | 5/2003 | Ota et al. | |
| 2003/0157569 A1 | 8/2003 | Ota et al. | |
| 2004/0110282 A1* | 6/2004 | Kanda et al. ................ | 435/325 |
| 2004/0132140 A1 | 7/2004 | Satoh et al. | |
| 2006/0246456 A1 | 11/2006 | Tsuchiya et al. | |

FOREIGN PATENT DOCUMENTS

| EP | 1 074 617 A2 | 2/2001 |
| EP | 1 130 094 A2 | 9/2001 |
| EP | 1 176 195 A1 | 1/2002 |
| EP | 1331266 A1 | 7/2003 |
| EP | 1 500 698 A1 | 1/2005 |
| EP | 1642971 A1 | 4/2006 |
| JP | 2001-333787 A | 12/2001 |
| WO | WO-00/56891 A2 | 9/2000 |
| WO | WO-00/61739 A1 | 10/2000 |
| WO | WO-01/53312 A1 | 7/2001 |
| WO | WO-02/31140 A | 4/2002 |
| WO | WO-03/085102 A2 | 10/2003 |
| WO | WO-03/085118 A1 | 10/2003 |

OTHER PUBLICATIONS

Luhn et al., The gene defective in leukocyte adhesion deficiency II encodes a putative GDP-fucose transporter, Nature Genetics, vol. 28, pp. 69-72 (2001).*
Kao et al., Genetics of somatic mammalian cells, VII. Induction and isolation of nutritional mutants in Chinese hamster cells, Genetics, vol. 60, pp. 1275-1281 (1968).*
Shields et al., J. Biol. Chem., vol. 277, No. 30, pp. 26733-26740, (2002).
P. L. Smith et al., J. Cell. Biol., vol. 158, No. 4, pp. 801-815, (2002).
Luhn K et al., "The gene defective in leukocyte adhesion deficiency II encodes a putative GDP-fucose transporter" Nature Genetics, Nature America. New York, US, vol. 28, No. 1, May 2001, pp. 69-72.
Database EMBL, Dec. 18, 2002, "Mus musculus adult male thymus cDNA, Riken full-length enriched library, clone:5830474F16 product:GDP-Fucose Transporter 1 homolog [Homo sapiens], full insert sequence." XP002400677.
Luhn K et al., "Identification and molecular cloning of a functional GDP-fucose transporter in Drosophila melanogaster" Experimental Cell Research, San Diego, CA, US, vol. 301, No. 2, Dec. 10, 2004, pp. 242-250, XP004626710.
Prati E. G.P. et al., "Antisense strategies for glycosylation engineering of Chinese hamster ovary (CHO) cells," Biotechnology and Bioengineering. Wiley & Sons, Hoboken, NJ. U.S., vol. 59, No. 4, Aug. 20, 1998, pp. 445-450.

(Continued)

Primary Examiner—Karen Cochrane Carlson
(74) Attorney, Agent, or Firm—Birch, Stewart, Kolasch & Birch, LLP.

(57) ABSTRACT

The present invention provides a gene encoding a fucose transporter, a fucose transporter polypeptide, a method for screening for a compound that binds to a fucose transporter or a compound that inhibits fucose transport activity, a cell having inhibited fucose transporter functions, and a cell wherein the expression of the fucose transporter is inhibited. The present invention further relates to a method for producing recombinant protein, and specifically, to a method for producing protein by which fucose existing within the Golgi apparatus of a host cell is decreased, a method for inhibiting the addition of fucose to protein by which fucose existing within the Golgi apparatus of a host cell is decreased upon production of recombinant protein using the host cell, a method for increasing the cytotoxic activity of an antibody by which an antibody is produced using a cell wherein fucose existing within the Golgi apparatus is decreased, and a cell having a Golgi apparatus wherein fucose existing within the Golgi apparatus is decreased.

11 Claims, 12 Drawing Sheets

OTHER PUBLICATIONS

Yamane-Ohnuki N. et al., "Establishment of FUT8 knockout chinese hamster ovary cells: an ideal host cell line for producing completely defucosylated antibodies with enhanced antibody-dependent cellular cytotoxicity," Biotechnology and Bioengineering, Interscience Publishers, London, GB, vol. 87, No. 5, Sep. 5, 2004, pp. 614-622.

Shinkawa T. et al., "The absence of fucose but not the presence of galactose or bisecting N-acetylglucosamine of human IgG1 complex-type oligosaccharides shows the critical role of enhancing antibody-dependent cellular cytotoxicity," Journal of Biological Chemistry, American Society of Biolochemical Biologists, Birmingham, U.S., vol. 278, No. 5, Jan. 31, 2003, pp. 3466-3473.

Ohyama C. et al., "Molecular cloning and expression of GDP-D-mannose-4, 6-dehydratase, a key enzyme for fucose metabolism defective in Lec13 cells," Journal of Biological Chemistry, American Society of Biolochemical Biologists, Birmingham, U.S., vol. 273, No. 23, Jun. 5, 1998, pp. 14582-14587.

Varki et al.., "Factors controlling the glycosylation potential of the Golgi apparatus," Trends in Cell Biology, Elsevier Science Ltd., XX, vol. 8, No. 1, Jan. 1998, pp. 34-40.

Abeijon C. et al., "Transporters of nucleotide sugars, nucleotide sulfate and ATP in the Golgi apparatus," Trends in Biochemical Sciences, Elsevier Haywards, GB, vol. 22, No. 5, Jun. 1997, pp. 203-207.

Zhou Y. et al., "Post-transcriptional suppression of gene expression in xenopus embryos by small interfering RNA," Nucleic Acids Research, Oxford University Press, Surrey, GB, vol. 30, No. 7, Apr. 1. 2002, pp. 1664-1669.

GenBank Acession No. AJ440724, Apr. 2, 2002, http://www.ncbi.nlm.nih.gov/sviewer/viewer.fcgi?20067424:OLD03:3737894.

GenBank Acession No. AK030977, Dec. 5, 2002, http://www.ncbi,nlm.nih.gov/sviewer/viewer.fcgi?26326910:OLD03:4671734.

Japan Office Action issued Feb. 2, 2010, in Japan Application No. 2005-513141.

Extended European Search Report issued in European Patent Application No. 05800043.1 on May 15, 2008.

Freeze, "Update and perspectives on congenital disorders of glycosylation," Glycobiology, vol. 11, No. 12, 2001, pp. 129R-143R.

Lubke et al., "Complementation cloning identifies CDG-IIc, a new type of congenital disorders of glycosylation, as a GDP-fucose transporter deficiency," Nat. Genet., vol. 28, No. 1, 2001, pp. 73-76.

Okada et al., "Gene Targeting," Shin Idenshi Kogaku Handbook, 1996, pp. 277-283.

Pennington et al., "Gene targeting in Chinese hamster ovary cells is conservative," Proc. Natl. Acad. Sci., vol. 88, No. 21, 1991, pp. 9498-9502.

Puglielli et al., "Reconstitution, identification, and purification of the rat liver golgi membrane GDP-fucose transporter," J. Biol. Chem., vol. 247, No. 50, 1999, pp. 35596-355600.

U.S. Office Action issued in U.S. Appl. No. 11/793,649 on Sep. 18, 2009.

Yagi et al., "Homologous recombination at c-fyn locus of mouse embryonic stem cells with use of diptheria toxin A-fragment gene in negative selection," Proc. Natl. Acad. Sci., vol. 87, No. 24, 1990, pp. 9918-9922.

Extended European Search Report dated Jul. 12, 2010 in European Application No. 10162932.7.

Extended European Search Report dated Jun. 21, 2010 in European Application No. 10161340.4.

Heidemann, Rüdiger et al., "A new seed-train expansion method for recombinant mammalian cell lines," Cytotechnology, vol. 38, pp. 99-108, 2002.

Mortensen, Richard et al., "Inactivation of G-Proteln Genes: Double Knockout in Cell Lines," Methods in Enzymology, vol. 237, pp. 356-366, XP008115526, Jan. 1, 1994.

Office Action dated Jul. 12, 2010 in copending U.S. Appl. No. 11/793,712.

* cited by examiner

Fig. 1-1

```
h-transporterORF    1: ATGAATAGGGCCCCTCTGAAGCGGTGTCCAGGATCCTGCACATGGCGCTGACCGGGCCTCA    60
m-transpoterORF     1: ------------------------------------ATGGCGCTGACTGGAGTCTCT       21
                                                           ** * **** h-transporterORF   61: GACCCCTCTGCAGAGGCAGAGGCCAACGGGGAGAAGCCCTTTCTGCTGCGGGCATTGCAG   120
m-transpoterORF    22: GCTGTCTCCGAGAGTCAGAGAGCGGGAACA---AGCCATTTCTGCTCCGGGCTCTGCAG    78
                        *    *  ****       *               *  *  **** h-transporterORF  121: ATCGCGCTGGTGTCTCCCTCTACTGGGTCACCTCCATCTCCATGGTGTTCCTTAATAAG   180
m-transpoterORF    79: ATCGCGCTGGTGTCTCTCTACTGGGTCACCTGGGTCAGCTGGATACCCCATTTTGTCACCTTCTACCAA  138
                      **************  ************ *     *  ** *  **  *    **** h-transporterORF  181: TACCTGCTGGACACAGCCCCTCCCTGCGGCTGGACCTCAGCGCTCTGGCCGCTCTGCCCTGGT   240
m-transpoterORF   139: TACCTGCTGGACACAGCCCCTCCCTGCGGCTGGACCTCAGCGCTCTGGCCGCTCTGCCCCGGC   198
                      ******************************************************* h-transporterORF  241: TGCCTGGTGACCACGCTGCTGCTGCAAAGGCCTCAGGGCTTGCCGCCTGGACCTGGAGACCTGG   300
m-transpoterORF   199: TGCCTGGTGACCTCCACTGCTGCTGCAAGGGCCTCAGCGCCTCTGGCCGCCTGCTGCCCGGC    258
                      ************  * ********** ****   *        * h-transporterORF  301: GCCGTGGACTTCCCCAGCTTGCCGCTCACTCAACCACCGTCTTCAACGTGCTGCTCCTCCACCTG   360
m-transpoterORF   259: ATGGTAGACTTCCCCACCACCTAAACCTGGACTGGACCTCAAGGTGCCCCGAAGTGTGCTGCCGCTG   318
                       * * *********   *  *    *                 **  ***** h-transporterORF  361: TCGGTGGTCTTCATCGGCATGATCACCTTCAATAACCTCTGCCTCAAGTACGTCGGTGTG     420
m-transpoterORF   319: TCAGTGGTCTTTATCGGCATGATCATGATAACCTTCAATAACCTCTGCCTCAAGTACGTAGGGGTG   378
                       ****  **********   * **** ** **********  *** h-transporterORF  421: GCCTTTCTACAATGTGGGCGCTCACTCACCACCGTCTTCAACGTGCTGCTCTCCTACCTG    480
m-transpoterORF   379: CCCTTCTACACAGATCGCTCGCGCTCACCACTTCCTTCTGCTCTATGCCCGTCTTCAACGTCAACTTCAACGTT   438
                      **** *       *             ******** h-transporterORF  481: CTGCTCAAGCAGACCACCTCCTTCTATGCCCTCACCTGCGGTATCATCATCGGGGGC    540
m-transpoterORF   439: CTGCTCAAACAGACCACTTCCTTCTATGCCCTCACCTGCGGCGTCATCATTGGTGGT    498
                      ****** ****  ********************   *  ** h-transporterORF  541: TTCTGGCTTGGTGTGGACCAGGAGGGGCAGAAGGCACCCTGTCGTGGCTGGGCACCGTC    600
m-transpoterORF   499: TTCTGGCTGGGTATAGACCAAGAG                                        558
                      ******** **  * *****  **
```

Fig. 1-2

```
h-transporterORF  601:TTCGGCGTGCTGCTGGCTAGCCTCTGTGTCTCGCTCAACGCCATCTACACCACGAAGGTGCTC 660
m-transpoterORF   559:TTCGGGGTGCTGCTGGCCAGCCTCTGCGTCTCCGTCTCCCTCAATGCCATCTATACCAAGAAGGTGCTC 618
                      **** **** *******   * ***   * * ***** **** h-transporterORF  661:CCGGGCGGTGGACGGCAGCATCTGGGCGCCTGCCTGACTTTCTACAACGTCAACGCCTGCATC 720
m-transpoterORF   619:CCTGCAGTAGACCACACTATCTGGGCGCCGCCTAACCTTCTATATAACATGTCAATGCCTGCGTG 678
                        * * *  *  * *   ** *   * *  ******* * h-transporterORF  721:CTCTTCCTGCCCCCTGCTCCTGCTCGGGGAGCTTCAGGCCCTGCCTGACTTTGCCCAG 780
m-transpoterORF   679:CTCTTCTTGCCCCTGATAGTGCTGGGCGAGCTCCGTGCCCTCCTGGCCTTCACTCAT 738
                      **** ****  *   * *   *****     **  *  *  ** * h-transporterORF  781:CTGGGCAGTGCCCACTTCTGGGGATGATGACGCTGGGCGGCCTGTTTGGCTTTGCCATC 840
m-transpoterORF   739:CTGAGCAGTGCCCACTTCTGGCTCATGATGACGCTGGGTGGCCTGTTTGGCTTTGCCATC 798
                      * **************  *  ************ ***************** h-transporterORF  841:GGCTACGTGACAGGACTGCAGATCAAGTTCACCAGTCCGCTGACCCACAATGTGTCGGGC 900
m-transpoterORF   799:GGCTATGTGACAGGACTGCAGATCAAATCAAATTCACCAGTCCCTGACCCATTAACGTGTCAGGC 858
                      *** ****************  *  *   ********* **  **** * h-transporterORF  901:ACGGCCAAGGCCTGTGCCCAGACAGTGCTGGCCGTGCTCTACTACGAGAGACCAAGAGC 960
m-transpoterORF   859:ACGGCCAAGGCCTGTGCACAGACAGTGCTGGCCGTGCTCTACTACGAAGAGATTAAGAGC 918
                      ***************  * **********************     *** h-transporterORF  961:TTCCTCTGGTGGTGGACAGAGCAACATGATGGTGCTGGGCGGCTCCTCCGCCTACACCTGGTC 1020
m-transpoterORF   919:TTCCTGTGTGGTGGACAAGCAACCTGATGGTGCTGTGGTGCTGGTGGCTCCTCCGCCTACACCTGGGTC 978
                      ***  ******** *  **  **  *   ************* * h-transporterORF  1021:AGGGGCTGGGAGATGAAGAAGACTCCGGAGGAGCCCAGCCCAAAGACAGCGGAGAAGAGC 1080
m-transpoterORF   979:AGGGGCTGGGAGATGCAGAAGACCCCAGCCCCAGCTCCAAAGATGGTGAGAAGAGT 1038
                      *************  ****   *    **  * *******  * ********* h-transporterORF  1081:GCCATGGGGGTGTGA 1095
m-transpoterORF   1039:GCTATCAGGGTGTGA 1053
                       ** ** ********
```

For RT-PCR  Forward primer: TGCAGATCGCGCTGGTGGTCTC
Reverse primer: GCCCCTGACCCAGGTGTAGGC

Fig. 2 gattcggcacgaggCGCTCCGCTTCCCACGCGGTCCCGACCTGTTCTTCCCTCCTCCACCCTGCCCTTCGTCCCTCTCCCTTCCTTTC
TCCCCTGACTCGTCCCTATTAGGCAACAGCCCCTGTGGTCCAGCCGCCATGGCTGTCAAGGCTGTCACACCCTTAGCCCCCTTCTC
CCTTCCCTGGGTCTTGTCTCATGACCCCCTGCCCCGCGGAGCGAGCGCGATGTGGAGCAGTGCCTCTGGCAAGCAGAACTTCACCCA
AGCCATGTGACAATTGAAGGCTGTACCCCCCAGACCCTAACATCTTGGAGCCCTGTAGACCAGGAGTGCTTCGCCGTGGGTGACCT
AGCTCTTCTACCACCATGAACAGGCCCCTCTGAAGGCGGTCCAGATCCTGCCAGATCGCGCTGGTCGTCTCTACTGGCGCCTCTGAGGAG
GCAGATGAAGACAGCAGGAACAAGCCGTTTCTGCTGGACAGCCCCTCAGCCCCTCTGCCTGCACCGTGGATACCCCTATCTTCGTCACTTTCGTCACTTGGGTCACCATCTCC
ATGGTATTCCTCAACAAGTACCTGCTGACAGCCCTCAGCACTCTGGCCACTCTGCATGGCTTTCATTGCATGATAAGTTTCAATAACCTCTGACTTCCCCACCCTGACTTGCCCTTAAGGTTGCC
TCTCTGCTGTGCAAGGGCTGCCACTGTGCCACCGTGTTCTGTGGGTAGTCTTCATTGCATGATAAGTTTCAATAACCTCTGCACCCCTGAAGTAGGGGGTGGCCTTCACATTGTGCC
CGCAGCGTGCTGCCTCGCTGCCACCGTGTCTGCCTGGATATAGACAAGAGGAAGTGCTCCCAGCTGAGCTCCGTTGCTGACAGTGCCCCAACAGCATCTGGCGCCTAACCTTCTATAAC
GTGGGGCGTCGCTGCCACCGTGTTCTGCCAATGCCATCTATACCAAGAGAAGTGCTCCCAGCTGAGCTCCGTTGCTGACCCGGCGCCTAACCTTCTATAAC
GCCAGCCCTGCGTCTGTGCTCATGATGACGCTGGGGTGCTCCTCCAGCCTATACCTGCTTCTTCCAGGACCTGCTTCAGACCCTCCCTTGGAATATGATCTAAGAGGAGCCCCAGCTCC
AATGTCAATGCCTCGGCTCATGATGACGCTGGGGTGCTCCTCCAGCCTATACCTGCTTCTTCCAGGACCTGCTTCAGACCCTCCCTTGGAATATGATCTAAGAGGAGCCAGCTCC
CACTTCTGGCTCACACATGTCATCAGGCACACAGCAGGCTCTGGGTGCTATTGGCCCTGAGCAATACTGTTTACATCCTCCTTGGAATATGATCTAAGAGGAGCCACCCACACCTGAAGGCTT
ACCCACACAATGAACCTGATGGTGCTCCAGTGCTGCCAATCTCCTGCTCTGCCCCATTCTGTTGTTTGGAAAACCTACCAGGAATGGCACCCTGCCTCCTCCTCCTCCTCAGAG
AAAGGGGTGAGAAAGCTCCAGAGTGCTGGGTGTGAGCAATACTGTTTACATCCTCCTTGGAATATGATCTAAGAGGAGCCACACAGGGGTCTTTCTGGTAA
CCTATGAGAGCTACGTGTGCCAGTGTGCGGGGTTGGGAGTAGAAGCTGCAGCTGCAATCTCCTGCTCTGCCCCATTGTTGGGACCAGCTGCAGCCTTAAGGGCTGAGTTGAAGGGGCTGGATTGATGAAGTGATGTCTTCTACACAAGGGAG
CCTGTCTACCTCACCTCCATATCATCTCGGGGTTGGGACCAGCTGCAGCCTTAAGGGCTGAGTTGATGAAGTGATGTCTTCTACACAAGGGAG
ATGGGTTGTGATCCCACCTAATTGAAGGGATTTGAAGGAAGTGGGAAGTGGGGAGCTTGCCCAAGGAGGAAATGCCATTCTGCCCCTCTTCAGTGTGATGA
ACATCAGGAACACCTCAGCCTGTCATGGCAGCTGCACACATCTTTACGGGGTGCCACCTGATAAGAAAACATTCACCTTCTGCATTTCATATTTGCAGCTCTAGAACG
GTATGGCAGACCTGTTCATGGCAGCTGCACACATCTTTACGGGGTTAAGTAGGGTGATGAGCTCTTCCGTCATGGCCTCCTAACCCCAGTTTACCTGCCTGCTTCCCTTG
GGGGAGACCACACATCTTTACGGGGTTAAGTAGGGTGATGAGCTCTTCCGTCATGGCCTCCTAACCCCAGTTTACCTGCCTGCTTCCCTTG
CCCAGCTACCTGTAACCTCTGTTCCCATGACAGAGCCCTTTGAATACCTGAATACTGAACCCTCATGACAGTAAGAGACATTTATGTTCTCGGGGCTG
GTCCACTTGTAACCTCTGTTCCCATGACAGAGCCCTTTGAATACCTGAATACTGAACCCTCATGACAGTAAGAGACATTTATGTTCTCGGGGCTG
GGGCTGAAGGAGCCCACTGGTTCTCACTTAGCCATTAGCCTCTGCTCCTCTGTCACAAAAAAAAAAAAAAAAAAActcgag For Probe5' side
Forward primer: TGCAGATCGCGCTGGTGGTCTC
Reverse primer: GCTCCTTCTTGGTCTATACC 3' side
Forward primer: AGACCACTTCCTTCTATGCC
Reverse primer: GCCCCTGACCCAGGTGTAGGC

```
GGTGAGGCCTTGCGCCGCCATGCCTCTGTCATTGCCCTCGGGCCGCCTCCCTGAACCTCCGTGACCGCCCTTGACTCG
GCGGGCGGCTTCCGGGCGGCTCCGCAGCCCTTCTCCCTTCCCTGGTCTTGTCACTAGCCACACTCCTCCCGGGCCCCACACCTGTCCCCCTGTCTTCCTC
TCCACCCTGCCCTTCTGTCCCTCCCTTCCCTGGTCTTGTCACTGTCCTCCCCTGACTGTCCCCTGACTGTCCAGCCGGCCATGCTGCTGTCAAGGCTCA
CACCCTTAGCTAGGCCCCTTCTCCCTTCCCTGGTCTTGTCATGATGCCCCCTGCCCCGGGAGCGAGCGAGTGGAGCCCTCTGGCAAGC
AGAACTTCACCCAAGCCATGTGACAATTGAAGGCTACCCCAGACATTTGAAGCCCTAACATTGGAGCCTAGACCAGGAGTGCTTCTGGCCGTGGGTGA
CCTAGCTCTTCTACCACCATGAACAGGGCCCCTCTGAAGCGGTCCAGATCGCGCTGTCGTCTCTACTGGGTCACCTCATCCATGGTATTCCTCAACA
GAAGACAGCAGGAACAGCCCCTGCTGCAGCTGGATACCCCTATCTTCGTCACTTTCTACAATGCCTGGTGACCTGTGCAAGGGCCTCAGCACT
CTGCCACCTGCTGCCACCGTTGACTTCCCACCGTAAGGTGGCCCGCAGCGTGCTCACCACGTGTTCAATGTCGTCTTCTGTCCTACCT
TGATAAGTTCAATAACCTCTGCCAAGTACGTAGGGGTGGCCTTCTACAACGTGGGGCGCTCGCTGCTCACCACGTGTTCAATGTCGTCTTCTGTCCTACCT
GCTCAAACAGACACTTCCTTCTCTATGCCCTGCTCACATGGCATCATCATTGGTGACCCTAAAACGTGGGGCGCTCGAGTGGGGCAGGATGGCATGAA
CTGAAGCCCTAAAGTCAACACTGTAGGTACCTTTACTTGTCCCAGTCCATCAGCAGTTACAGAAGAGCCCTGTAGAAAACAAATAACT
TCCTTATGGTCATTCAACAAGTTAGGGACCCAGGCAGGTGAAAATAATGTTAGCAACTACAGCAAAGATGGCTCTCGCCACTTGCATGATTAAAA
TGTGCCAGTTACTCAGATCTAAGCATTGGATCCACATTAACTACCACAGCAAGTTAACTACCAGTAATATATCCGAATTTTACAGAGGAAACCAAG
GCACAGAGAGGCTAAGTAGCTTGACCAGGATCACACAGCTTGAGGATTAAACATAAGCAGTTACCTCATAGATCACACTA
TGACCACCATGCCACTGTTCCTTCTCAAGAGTTCCAGGAGTTTAAGTTTTTATTCTTACTTTTATGTGTGTGTTTATGTGTGAGATAAGGGG
CATTTGAATAGTGGGTAGACATATGTTTTAAGTTTTTATTCTTACTTTTATGTGTGTGTTTATGTGTGAGATAAGGGG
ACAACTTAAGAATTGGTCTTCCCACCACAGAGGCTTTAAGAGAGGCTCTGAACTCAGGATTGGCACAAATCCCTTTACCGTGAGCCATTTC
ACTGGTCCAATATATGTGGTCGTCTGCATACAAATGGAAACTGCAACAAAGGCTACTTCCCCAGATGTCCTGATCATTATCCCTTACCGGAAGCCCTCGGGA
GGTGCCATCCCTGGTGGCCACACTGGCCACCTCCCTGGCTCAAGCCAGTTTACTTGTCTCTGCTTCAAGCCAGTTAGCATGTGCAGTCAAACACATAACT
ACAGGCCAAAAGTGCTTTAAATTAAAGTCAGATGAACTTTAAACATCCAGAGCTCTCAACTGCAGGAGTTACAACCTGATTCTGCAACCATCTTTGC
AGTGCCGGTAGTCATATGTAGCTAGGACTCTGGGCAAGCTCGGGCGACCTAAGACCCTCTACACGATGCCCCTACTACCAGTTCACTTCAAGACTGCTGGGT
GACAAAGACCAAGGCATCCGTTCCCGTCTCAGAGGCATCTGACCAGGCAAGCAGGAGTCAGATAAAAAGCTGACACTGGGACTCGACACTGGGCCACTGCCCC
CTTAGTCTCCTGAATCATCCTAAGAGAACTTCATCGGTAAAGGGTCTGACCAGGTCGACCAGGAGAGTCAGATAAAAAGCTGACACTGGGGACTCCACTGCCCC
CAGCTCCTGAATCATCCTAAGAGAACTTCATCGGTAAAGGGTCTGACCAGGTCGACCAGGAGAGTCAGATAAAAAGCTGACACTGGGAACTCCACCTGCCC
CACACATCCTGAATCATCCTAAGAGAACTTCATCGGTAAAGGGTCTGACCAGGTCGACCAGGAGAGTCAGATAAAAAGCTGACACTGGGAACTCCACCTGCCC
GGCATGAGCCTCCTTGTGGCAGCAGCCTGTGAACTGCGCCTGAACTCAGTCCAAAGTAACAGTACCTGAGCTTGCCAGGGTTAGAG
CAGCTGAGAACCGCAGCAGCCTGTGAACTGCGCCTGAACTCAGTCCAAAGTAACAGTACCTGAGCTTGCCAGGGTTAGAG
GGCCCATCTCTGATAGTGCTGTGGGACTCTAGAGGGTAAGGAGGAGAAGAGCAATCTAAGAGGCCTTACTGAAGTCCTTGCTGCATGTGGCTGC
CTGAGGAGTACAGACTGGGAACACCCATTTGAATGAGTAAGGTTTTTCCTGAAGGCCACGAGGAGAAATCATTTAGTTACAAGACAA
AGAGTAGATTGGTTAACATGGGAGCAAGGACATGCCCCAATTTTCATAGATGAAGGAAATTGGAACTCAGAGAGGTTAAGTAACTTCTCCCAAATAG
CTCAGCTTCAAATCACAGAACAGTCCAGGATCTAAATGAAGAGAAGCAACATGTCCCATTCCATGTGCTGATCCCTGTTGCTGATCCGTGCATCAGTAAGCC
TCTACCTTGTGGGAATGCAGGATCTAAATGAAGAGAAGCAACATGTCCCATGGCTCTGAAAGCTATGCAGGCTCTTTGAGCAGAGAGTGACC
CACAAGTGAATAGAGTCCTATGAGACTCAAAGCAACATCCACCCTTAAGCAGCTCTAACCAAATGCTCACACTGAGGGAGCCAAAGCCAAGTTAGAGT
CCTGTGCTTGCCCAAGGTCACTTTGCCTGGCCCTCCTCTAGAATTGCTGCTTATCTTATAGCCACCGTGTTATCTTATAGCCCCTCATCAATTACATTAGAGAGGTA
ACAGGGCCACACTGTCCTTACACATTCCCCTGCTAGATTGTAGCTGTAGGAGGGGAGAGTGTAGGTGGCTGGGAGTGGGAGGGAAGATGCAGATTT
```

Fig. 4-3

```
TCATTCTGGGCTCTACTCCCTGACCATTTTTGGTGTGGGAGTTAGACTTTGGATATGTTGATGATGAGGTAAGGGCCACAGAACAGTCTGAACTGTGG
TATCAGAATCCTGTCCCTCTCCCTCATCCCTCCTCACCTTGTCACTCCTCTGTCTGTCTGCTACAGGTGGTTTCTGGCTGGGTATAGACCAAGAGGGA
GCTGAGGGCACCCTGTCCCTCATAGGCACCATCTTCGGGGTGCTGGCCAGCCTCCCCAATGCCATCTATACCAAGAAGTGCTCCAGCAG
TGGACAACAGCATcTGGGCGCTAACCTTCTATAACAATGTCAAGCCTGTGTCTCTTCTGCCCCTGATGGTTCTGCTGGGTGAGCTCCGTGCCCTCCTT
GACTTTGCTCATCTGTACAGTGCCCACTTCTGGCTCATGATGACCAAGGCCTGTCATGAGCCAAGCCTATACCTGGGTCTGCCGTGCAGACTAAGAGACTTCCTGTG
CACCAGTCCCCCTGACCCACAAACCTGATGGTCTGCGGTGTGCGCAGACAGTGCTGCCGTGCTGCCGTCTACTATGAAGAGACTAAGAGACTTCCTGTG
GTGGACAAGCAAGCCTGATGTGGTCTGCGGTGTGAGCTCTTCAGGGACCTGGGCTGTGAGCCTATACCTGGGACTGGGAGATGCAGAAGACCCAAGCTCAAAG
AGGGTGAGAAGAGTGCTATTGGGGTGTGAGCTCTTCAGGGACCTGGGGACTGAACCTGAGAATATGGGGCCTACACAGCACTGAAGGCTTCCATGAGCTA
GCCAGTGTGGCCCTGAGCAATACTGTTTACATCTCCTTGGAAATATGATCTAAGAGGAGCCAGGGTCTTCTCAGAGCCTGTAATGTCAAAGCTGCCAAATCTC
CTGTCTGCCCCATCTGTTTGGGAAAACCTGCTGGATTGAAGTGATGTCTTCTACACAAGGGAGATGGGTTGTGATCCCACTAATTGAAGGGATTTGGGTGACCC
ACCAGCTGCAGCCTTAAGGGCTGCAGGTAGAGTAGCTTAGGTGCTATTAACATCAGGAACACCTCAGCTGCACCCTGCCTTTGAAGGAAGTGGGAGCTTGCCAA
ACACCTCTGGGATCCAGGGACATTCTGCCCTCTTCAGTGTGGATGAGTGAGTAGGGCAGAATCTTTCATGGCAGAACCTGTTCATGCCGTGCTGATAAGAAACATTCACC
GGGAGGAAATGGCATTCTGCCCTCTTCAGTGTGGATGAGTGAGTAGGGCAGAATCTTTCATGGCAGAACCTGTTCATGCCGTGCTGATAAGAAACATTCACC
TCTGCATTTCATATTTGCAGCTCTAGAACGGGGAGAGCCACACATCTTCCCTTCTGAACCCCTGACTGCTGCTGATGGTTAAGTAGGTGATGAGCTCCTCCGTACCCCAGTT
TACCTGCCTGGCTCCTGCCCAGCTACCTCTGTTCCATGCCCTATCCTGCCTCCTTTGAATACCTGAAGAGGACATTTATGTTCTCGGGGCTGGG
GAAGTGGAGTCCACTTGATACCTCTGTTCCATGCCCTATCCTGGCTCCTGTCACAAAAAAAAAGCATAAACCAAGTTACTAAGAACAG
GCTGAAGGAGCCCACTGTTCTCACTTAGCCTCATAGGCAGCAAAGCCCAGATGAAGGACCCATGAGGGGCCCTCATATCCTCTGTCCATGTGCAGAAGACTCCAACGTAAATTT
AAGTTGGTTTATAGGAACCTCATAGAACACTAGCTTCACTGCCCAGCCTACACAGCAGCTAGCCTCACTGAGGGTTTACTCCGTAACCTCAGTGCTCCATGTCAAATGAGGACTCAACGTAAATTT
CTTTAAGCCTCATATAGGAACACTAGCTTCACTGCCCAGCCTACACAGCAGCTAGCCTCACTGAGGGTTTACTCCGTAACCTCAGTGCTCCATGTCAAATGAGGACTCAACGTAAATTT
GGGGACAGAAGCACTCAGAACTAGGACACCATACCCCAGCAGCAGCACTCCAGCCAGCACACCATAACCTCAGGGTAGCTCATTCCTCGGCCTTTAGAACCCCCC
ATTTCCTTGGGGTAATGTCTGATGTGTTGTCCCTGATGTTTGTCCTCATAAAAGATGAGAGACTGTGTCCAGCCTTTGATTCCTACAATCCCAGTTCTAA
TGAAGTTGTGGGGCCTGATGCCCTGAGTTGTATGTGATTTAATAAAAAAAGCAAGCATGTGTGGACTGAGTGAGGGCCACAGGATCT
AAAAGCCAAGTGTGAGGGACCAGTACACAGGCAGCATCCTGAGCCTGTGCTCTTACTGAAGGCAGACATGGCACTGAGTCTGTCCATCTGTCACTCA
GTAGGTGGCCAGAGTTCAAGTTCCTAATGTGTGGGGTGGGAGCTGGGAGCCACCTTGGAAGGAGAAGAGGCTTGTCACACAGCACCATATGACCTTGAGCCAGGCTGTGTGTGAGAAAGTAG
TCTCCACAGCAATTCCAGAGTGCCTGGCCTTCTTCTTCAGATGAGAGGTGGACACCCAGGCTTCTAAGGTGTGTCAGTGTCCTGAATCAGGGGCTGAACCTGACCTTGATCAGTCACTCCTACCAGA
CAGCAGAATTCAGAGTGCCTGGCCTTCTTCTTCAGATGAGAGGTGGACACCCAGGCTTCTAAGGTGTGTCAGTGTCCTGAATCAGGGGCTGAACCTGACCTTGATCAGTCACTCCTACCAGA
CAGCCTAGAGTCCCTGGCTCCCAGCCTGGCTCCCCAGCTTCTTTTCAGATGAGAGGTGGACACCCAGGCTTCTAAGGTGTGTCAGTGTCCTGAATCAGGGGCTGAACCTGACCTTGATCAGTCACTCCTACCAGA
GGGAGGATTACTGTGGCTCCCAGCCTGGCTCCCCAGAAGAGGTGGACACCCAGGCTTCTAAGGTGTGTCAGTGTCCTGAATAGGCATTTCTGCTCACCCTATACCCTGAGCAGTAGG
ATGTGGGGAATGGGATATCCACAAACCAGTAGCCGTTCCTGGCAGTGGGTGTAAGTGTGTGGCAGTGGGTGAATACTGCCAAGGCAGTAGAACCACC
AAGGCCCTGTGGAGAATATCTAGAGAAATTACAGGTCATCTTAAGCCTCTAAATTGTGGAGAAACTGACATGCGCACGATTCTAACCTGCTAGCCTAGGGTGC
CAACCCACACAATCTAGAGAAATTACAGGTCATCTTAAGCCTCTAAATTGTGGAGAAACTGACATGCGCACGATTCTAACCTGCTAGCCTAGGGTGC
GGGTGGATAATTTAAGGAAACTGGGTTTCTTATAGAATGGAGGCTCCATGAAGCTCACATCTGGGTGTCTATAGGTGTGACTGTGTCTGAGATACTGCCTCAGTGCCAGCAGCCATTGCAA
CTCCTAAGCCTTAGCCCATGGGTTGGGATAGCAGCAAGCAGCAGCAGCCTGTAAAGCAAATGCTGTTTCCCTTAAACTGCCCAAACCATTGTTTGCAGTGAGCTGATGATAAGAAAACAAGCCCA
TGGGCCCTTAGCCCATGGGTTGGGATAGCAGCAAGCAGCAGCAGCCTGTAAAGCAAATGCTGTTTCCCTTAAACTGCCCAAACCATTGTTTGCAGTGAGCTGATGATAAGAAAACAAGCCCA
AAATGTTTTCTTTCCAGACTCTGATCTTTCTTTGTTCAAAAATGTCTGTTTCCCTTAAACTGCCCAAACCATTGTTTGCAGTGAGCTGATGATAAGAAAACAAGCCCA
AGAAAGATTAAAGGAAGTTTCTGAGGTTACAGAGCAAAGTTTTCACCTGAGCCAAAGTAAGAGTACTGCTCACCTGAGTGCTGAGATAGAGACAGGTGCCTGATCCTGATTTGAGCTC
```

FUCOSE TRANSPORTER

TECHNICAL FIELD

The present invention relates to a fucose transporter polypeptide, a DNA encoding the fucose transporter polypeptide, a cell having inhibited fucose transporter functions, and a method for screening for a compound that binds to a fucose transporter or a compound that inhibits fucose transport activity. The present invention further relates to a method for producing a recombinant protein and particularly an antibody using the cell having inhibited fucose transporter functions.

BACKGROUND ART

Antibodies can exert anti-tumor effects via their ADCC (antibody-dependent cell-mediated cytotoxicity) activity or CDC (complement dependent cytotoxicity) activity. Antibodies are sugar chain-bound glycoproteins. It is known that an antibody's cytotoxic activity can vary depending on the types and amounts of sugar chains that bind to the antibody. In particular, it has been reported that the amount of fucose binding to an antibody is strongly involved in the cytotoxic activity (Shields et al., J Biol Chem., 277(30), 26733-26740, 2002). Furthermore, a method for producing a recombinant antibody not having fucose has been reported. Such method involves preventing an enzyme that catalyzes the binding of fucose to a sugar chain from being expressed upon antibody production in order to obtain an antibody with enhanced cytotoxic activity (International Patent Publication No. WO00/61739).

SUMMARY OF THE INVENTION

An object of the present invention is to isolate a fucose transporter gene or polypeptide intracellularly involved in fucose transport. Furthermore, another object of the present invention is to obtain a cell for producing a foreign protein having inhibited fucose transporter functions. Furthermore, another object of the present invention is to isolate a compound that can inhibit fucose transporter functions. Furthermore, another object of the present invention is to provide a method for easily and reliably producing a recombinant protein wherein the binding of fucose is eliminated or decreases. In particular, an object of the present invention is to provide a method for producing an antibody wherein the binding of fucose is eliminated or decreases and whose cytotoxic activity is enhanced. Furthermore, another object of the present invention is to provide a host cell for producing such protein.

In a mechanism by which fucose binds to an antibody within an antibody-producing cell, it is known that GDP binds to fucose that has been incorporated into a cell. GDP-fucose is then incorporated into the Golgi apparatus and then the fucose of the GDP-fucose is transferred to N-acetylglucosamine that has been added as a sugar chain to protein within the Golgi apparatus. Specifically, the Fc region of an antibody molecule has two sites to which an N-glycoside-bound sugar chain binds. Fucose binds to the N-acetylglucosamine portion of an N-glycoside-bound sugar chain (Pate L. Smith et al., J. Cell Biol. 2002, 158, 801-815). The present inventors have studied this mechanism and inferred that if incorporation of GDP-fucose into the Golgi apparatus can be inhibited, the binding of fucose to protein can be suppressed. As a result of intensive studies concerning a substance that incorporates GDP-fucose into the Golgi apparatus, the present inventors isolated the substance as a fucose transporter and have discovered that an antibody to which no fucose binds and which has enhanced cytotoxic activity can be obtained by using a cell (having inhibited fucose transporter functions) as a host for the production of recombinant protein. Thus, the present inventors have completed the present invention.

In the present invention, to satisfy conditions where the addition of fucose to an antibody is inhibited, it is not necessary that all the produced antibodies do not experience the addition of fucose thereto, but the proportion of protein to which fucose has been added should be decreased among antibody compositions.

The present invention will be described in detail as follows.
[1] A recombinant polypeptide or a fragment thereof as shown in (a) or (b):
(a) a polypeptide comprising the amino acid sequence represented by SEQ ID NO: 2; or
(b) a polypeptide comprising an amino acid sequence derived from the amino acid sequence represented by SEQ ID NO: 2 by deletion, substitution, insertion, or addition of 1 or several amino acids and being functionally equivalent to the polypeptide (a).
[2] A DNA, which encodes the following polypeptide (a) or (b):
(a) a polypeptide comprising the amino acid sequence represented by SEQ ID NO: 2; or
(b) a polypeptide comprising an amino acid sequence derived from the amino acid sequence represented by SEQ ID NO: 2 by deletion, substitution, insertion, or addition of 1 or several amino acids and being functionally equivalent to the polypeptide (a).
[3] A DNA, which comprises the following DNA (c) or (d):
(c) a DNA comprising the nucleotide sequence represented by SEQ ID NO: 1; or
(d) a DNA hybridizing under stringent conditions to a DNA consisting of a sequence complementary to the DNA comprising the nucleotide sequence of SEQ ID NO: 1 and encoding a polypeptide that is functionally equivalent to a polypeptide encoded by the DNA (c).
[4] A DNA fragment, which is a fragment of the DNA according to [2] or [3] or is a fragment of a DNA that is complementary to the DNA according to [2] or [3] and consists of at least 15 nucleotides.
[5] A recombinant vector, which comprises the DNA according to [2] or [3].
[6] A transformant, which comprises the recombinant vector according to [5].
[7] A method for producing the polypeptide according to [1], which comprises culturing the transformant according to [6] and collecting the polypeptide from the cultured transformant or the culture supernatant thereof.
[8] An antibody, which binds to the polypeptide according to [1].
[9] A screening method for a compound that binds to the polypeptide according to [1], which comprises the steps of:
(a) contacting a sample to be tested with the polypeptide;
(b) detecting the binding activity between the polypeptide and the sample to be tested; and
(c) selecting a compound having activity of binding to the polypeptide.
[10] A compound binding to the polypeptide according to [1], which can be isolated by the method according to [9].
[11] A screening method for a compound that inhibits the GDP-fucose transport activity of the polypeptide according [1], which comprises the steps of:
(a) contacting a sample to be tested and GDP-fucose with the polypeptide;

(b) detecting the GDP-fucose-incorporating ability of the polypeptide; and (c) selecting a compound that inhibits the GDP-fucose transport activity of a polypeptide.

[12] A compound that inhibits the GDP-fucose transport activity of the polypeptide according [1], which can be isolated by the method according to [11].

[13] A cell, which has a Golgi apparatus wherein fucose is decreased.

[14] A cell, which exhibits decreased fucose transport ability or lacks such ability.

[15] A cell, which exhibits decreased activity of incorporating fucose into a Golgi apparatus, or which lacks such activity.

[16] The cell according to any one of [13] to [15], which is treated with a compound that binds to a fucose transporter or a compound that inhibits fucose transport activity.

[17] A cell, wherein the expression of a fucose transporter is artificially suppressed.

[18] The cell according to [17], wherein the expression of a fucose transporter is suppressed by using RNAi.

[19] A cell, wherein a fucose transporter gene is disrupted.

[20] The cell according to any one of [13] to [19], which is an animal cell.

[21] The cell according to [20], wherein the animal cell is a Chinese hamster cell.

[22] The cell according to [20], wherein the animal cell is a CHO cell.

[23] The cell according to any one of [19] to [22], wherein the gene is disrupted by homologous recombination using a gene targeting vector.

[24] A targeting vector, which targets a gene encoding a fucose transporter.

[25] The targeting vector according to [24], wherein the fucose transporter is a Chinese hamster fucose transporter.

[26] A method for producing a recombinant protein, wherein fucose existing in the Golgi apparatus of a host cell is decreased.

[27] A method for producing a recombinant protein, wherein the incorporation of fucose into the Golgi apparatus in a host cell is inhibited.

[28] A method for producing a recombinant protein, wherein the incorporation of fucose mediated by a fucose transporter in a host cell is inhibited.

[29] A method for producing a recombinant protein, wherein fucose transporter functions of a host cell are inhibited.

[30] The method for producing a recombinant protein according to any one of [26] to [29], wherein the fucose transporter functions are inhibited by artificially suppressing the expression of the fucose transporter in a host cell.

[31] The method for producing a protein according to [30], wherein the expression of the fucose transporter is suppressed using RNAi.

[32] The method for producing a recombinant protein according to any one of [26] to [30], wherein the fucose transporter functions are inhibited by deleting a gene encoding the fucose transporter in a host cell.

[33] The production method according to any one of [26] to [32], wherein the protein is an antibody.

[34] The production method according to any one of [26] to [33], wherein a protein not having fucose added thereto is produced.

[35] The production method according to any one of [26] to [34], wherein the host cell is a CHO cell.

[36] A method for inhibiting the addition of fucose to a protein, wherein fucose existing in the Golgi apparatus in a host cell is decreased when a recombinant protein is produced using the host cell.

[37] A method for inhibiting the addition of fucose to a protein, wherein fucose transporter functions in a host cell are inhibited when a recombinant protein is produced using the host cell.

[38] The method for inhibiting the addition of fucose to a protein according to [36] or [37], wherein the expression of a fucose transporter is artificially suppressed when a recombinant protein is produced using a host cell.

[39] The method for inhibiting the addition of fucose to a protein according to [38], wherein the expression of a fucose transporter is suppressed using RNAi.

[40] The method for inhibiting the addition of fucose to a protein according to any one of [36] to [38], wherein a gene encoding a fucose transporter is deleted when a recombinant protein is produced using a host cell.

[41] A method for inhibiting the addition of fucose to a protein, wherein the incorporation of fucose mediated by a fucose transporter is inhibited when a recombinant protein is produced using a host cell.

[42] The method for inhibiting the addition of fucose to a protein according to any one of [36] to [41], wherein the protein is an antibody.

[43] The method for inhibiting the addition of fucose to a protein according to any one of [36] to [42], wherein the host cell is a CHO cell.

[44] A method for increasing the cytotoxic activity of an antibody, wherein an antibody is produced with a cell in which fucose existing in the Golgi apparatus is decreased.

[45] A method for increasing the cytotoxic activity of an antibody, wherein an antibody is produced with a host cell having inhibited fucose transporter functions.

[46] A method for increasing the cytotoxic activity of an antibody, wherein an antibody is produced with a cell in which the expression of a fucose transporter is artificially suppressed.

[47] A method for increasing the cytotoxic activity of an antibody, wherein an antibody is produced with a cell that lacks a gene encoding a fucose transporter.

[48] A method for increasing the cytotoxic activity of an antibody, wherein an antibody is produced by inhibiting the incorporation of fucose into the Golgi apparatus.

[49] The method for increasing the cytotoxic activity of an antibody according to any one of [44] to [48], wherein the host cell is a CHO cell.

This specification includes part or all of the contents as disclosed in the specification and/or drawings of Japanese Patent Application Nos. 2003-174006, 2003-174010, 2003-282081, and 2003-282102, which are priority documents of the present application.

BRIEF DESCRIPTION OF THE DRAWINGS

FIG. 1 shows human (SEQ ID NO: 11)and mouse (SEQ ID NO: 12)GDP-fucose transporter cDNA sequences and PCR primer sequences (SEQ ID NO: 13 and 14)for producing a probe, which have been designed to obtain CHO-derived GDP-fucose transporter cDNA from these common sequences.

FIG. 2 shows a CHO-cell-derived GDP-fucose transporter cDNA sequence(SEQ ID NO: 15) obtained by cloning (lower-case letters indicate vector-derived cloning sites). FIG. 2 also shows PCR primer sequences (SEQ ID NO: 16-19)for producing a probe that was used for obtaining GDP-fucose transporter genomic DNA.

FIG. 4 shows a CHO-derived GDP-fucose transporter gene sequence (SEQ ID NO: 1).

BEST MODE FOR CARRYING OUT THE INVENTION

Figure 3:
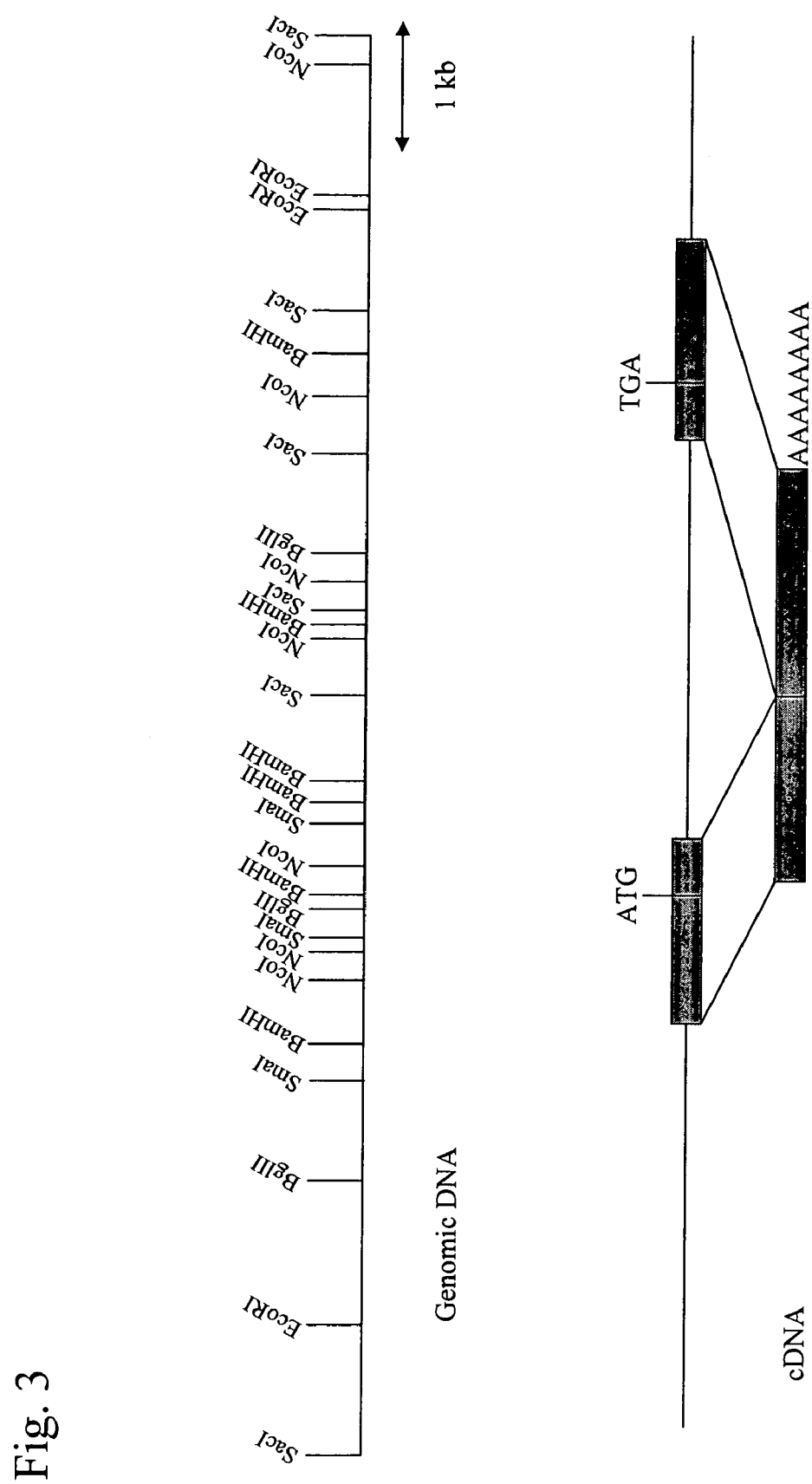
FIG. 3 shows a restriction enzyme map of a GDP-fucose transporter gene obtained by cloning. The underlined portion indicates a sequence (lower-case letter: intron) located at the boundary portion between an exon and an intron.

The present invention provides a Chinese hamster (CH) fucose transporter.

Chinese hamster ovary cells (CHO cells) are currently widely used as host cells for producing proteins such as antibodies. Thus, the Chinese hamster fucose transporter of the present invention is particularly useful.

The present invention also encompasses DNA encoding polypeptides that are functionally equivalent to the CH fucose transporter gene. Examples of such DNA include DNA encoding a mutant, allele, variant, homolog, or the like of a CH fucose transporter polypeptide. Here, "functionally equivalent" indicates that a subject polypeptide has biological functions equivalent to those of the CH fucose transporter polypeptide.

In the present invention, "biological functions equivalent to those of the CH fucose transporter" indicates fucose transport activity, and preferably the fucose transport activity in CHO cells.

As a method for preparing a polypeptide that is functionally equivalent to a polypeptide that is well known by persons skilled in the art, a method for introducing mutation into a polypeptide is known. For example, persons skilled in the art can prepare a polypeptide that is functionally equivalent to the CH fucose transporter polypeptide by appropriately introducing mutation into amino acids of the polypeptide through the use of, for example, the site-directed mutagenesis method (Gotoh, T. et al. (1995), Gene 152, 271-275; Zoller, M J, and Smith, M. (1983), Methods Enzymol. 100, 468-500; Kramer, W. et al. (1984), Nucleic Acids Res. 12, 9441-9456; Kramer W and Fritz H J (1987), Methods. Enzymol. 154, 350-367; Kunkel, T A (1985), Proc Natl Acad Sci U.S.A. 82, 488-492; and Kunkel (1988), Methods Enzymol. 85, 2763-2766).

Furthermore, amino acid mutation can also take place in nature. Thus, the present invention also includes a polypeptide consisting of an amino acid sequence derived from the amino acid sequence of the CH fucose transporter polypeptide by mutation of 1 or a plurality of amino acids that is functionally equivalent to the polypeptide. The number of mutated amino acids in such a mutant is generally 30 amino acids or less, preferably 15 amino acids or less, further preferably 5 amino acids or less, and particularly preferably 3 amino acids or less.

It is desirable that amino acid residues are mutated to result in other amino acids while retaining the properties of an amino acid side chain. Examples of such properties of an amino acid side chain include hydrophobic amino acids (A, I, L, M, F, P, W, Y, and V), hydrophilic amino acids (R, D, N, C, E, Q, G, H, K, S, and T), amino acids having aliphatic side chains (G, A, V, L, I, and P), amino acids having hydroxyl-group-containing side chains (S, T, and Y), amino acids having sulfur-atom-containing side chains (C and M), amino acids having carboxylic-acid- and amide-containing side chains (D, N, E, and Q), amino acids having base-containing side chains (R, K, and H), and amino acids having aromatic-containing side chains (H, F, Y, and W) (all the capital letters in parentheses represent single-letter denotations for amino acids).

It is already known that a polypeptide having an amino acid sequence derived from an amino acid sequence by modification such as by deletion of 1 or a plurality of amino acid residues, addition of 1 or a plurality of amino acid residues, and/or substitution with other amino acids retains its biological activity (Mark, D. F. et al., Proc. Natl. Acad. Sci. U.S.A.. (1984) 81, 5662-5666; Zoller, M. J. & Smith, M., Nucleic Acids Research (1982) 10, 6487-6500; Wang, A. et al., Science 224,1431-1433; Dalbadie-McFarland, G. et al., Proc. Natl. Acad. Sci. U.S.A. (1982) 79, 6409-6413).

Examples of a polypeptide having an amino acid sequence derived from the amino acid sequence of the CH fucose transporter polypeptide by addition of a plurality of amino acids include fusion polypeptides comprising such polypeptides. Such fusion polypeptides result from the fusion of such polypeptides with other polypeptides. Such fusion polypeptides are also included in the present invention. To prepare a fusion polypeptide, for example, DNA encoding the CHO fucose transporter polypeptide is ligated to a DNA encoding another polypeptide so that the frames match. The resultant is then introduced into an expression vector and expressed by a host. Examples of other polypeptides that can be fused with the polypeptide of the present invention include, but are not specifically limited to, known peptides such as FLAG (Hopp, T. P. et al., BioTechnology (1988) 6, 1204-1210), 6 x His consisting of 6 His (histidine) residues, 10× His, influenza hemagglutinin (HA), human c-myc fragments, VSV-GP fragments, p18HIV fragments, T7-tag, HSV-tag, E-tag, SV40T antigen fragments, lck tags, α-tubulin fragments, B-tags, and Protein C fragments. Furthermore, examples of other polypeptides to be fused with the polypeptide of the present invention include GST (glutathione-S-transferase), HA (influenza hemagglutinin), immunoglobulin constant region, β-galactosidase, and MBP (maltose-binding protein). These polypeptides and genes encoding the polypeptides are marketed. Hence, a fusion polypeptide can be prepared by fusing a DNA encoding such marketed polypeptide with DNA encoding the polypeptide of the present invention and then expressing the thus prepared fusion DNA.

Furthermore, another example of a method for preparing a DNA encoding a polypeptide that is functionally equivalent to a polypeptide that is well known by persons skilled in the art is a method using hybridization techniques (Sambrook, J et al., Molecular Cloning $2^{nd}$ ed., 9. 47-9. 58, Cold Spring Harbor Lab. Press, 1989). Specifically, techniques known by persons skilled in the art are isolation of a DNA having high homology with a DNA sequence that encodes the CH fucose transporter polypeptide or a portion thereof and isolation of a polypeptide functionally equivalent to the CH fucose transporter polypeptide from the DNA.

The present invention includes DNA hybridizing under stringent conditions to the DNA encoding the CH fucose transporter polypeptide and encoding a polypeptide functionally equivalent to the CH fucose transporter polypeptide. Examples of such DNA include homologs derived from humans or other mammals (e.g., rats, rabbits, and cattle).

Hybridization conditions for the isolation of DNA encoding a polypeptide that is functionally equivalent to the CH fucose transporter polypeptide can be appropriately selected by persons skilled in the art. Such stringent conditions for hybridization are, for example, low stringent conditions. Such low stringent conditions comprise, upon washing after hybridization, for example, 42° C., 0.1×SSC, and 0.1% SDS, and preferably 50° C., 0.1×SSC, and 0.1% SDS. More preferable hybridization conditions are, for example, high stringent conditions. Such high stringent conditions comprise, for example, 65° C., 0.1×SSC, and 0.1% SDS. Under these conditions, it can be expected that DNA having high homology as the temperature is elevated may be efficiently obtained. However, a plurality of factors such as temperature and salt concentration may influence the stringency concerning hybridization. Persons skilled in the art can realize stringency similar to the above stringency by appropriately selecting these factors.

Moreover, DNA encoding a polypeptide functionally equivalent to the CH fucose transporter polypeptide can also be isolated by a gene amplification method (e.g., a polymerase chain reaction (PCR) method) using primers that are synthesized based on the sequence information concerning the DNA encoding the CH fucose transporter polypeptide.

A polypeptide that is encoded by DNA isolated by these hybridization techniques and gene amplification techniques and that is functionally equivalent to the CH fucose transporter polypeptide generally has high homology with the CH fucose transporter polypeptide in terms of amino acid sequence. Examples of the polypeptide of the present invention also include polypeptides that are functionally equivalent to the CH fucose transporter polypeptide and that have high homology with the amino acid sequences of the polypeptide. Such high homology at the amino acid level indicates generally 70% or more homology, preferably 80% or more homology, further preferably 92% or more homology, and further preferably 95% or more homology.

Furthermore, such high homology at the nucleotide sequence level indicates generally 70% or more homology, preferably 80% or more homology, further preferably 90% or more homology, and further preferably 95% or more homology.

The homology of amino acid sequences or nucleotide sequences can be determined by, for example, algorithm BLAST (Proc. Natl. Acad. Sci. U.S.A. 90: 5873-5877, 1993) according to Karlin and Altschul. Based on this algorithm, a program called BLASTN or a program called BLASTX has been developed (Altschul et al., J. Mol. Biol. 215: 403-410, 1990). When nucleotide sequences are analyzed by BLASTN based on BLAST, parameters are determined to be, for example, score=100 and word length=12. Furthermore, when amino acid sequences are analyzed by BLASTX based on BLAST, parameters are determined to be, for example, score =50 and word length=3. When BLAST and Gapped BLAST programs are used, default parameters for each program are used. Specific techniques for these analysis methods are known.

The DNA of the present invention is used for, for example, in vivo or in vitro production of the polypeptide of the present invention as described later. The DNA of the present invention may be in any form as long as it can encode the polypeptide of the present invention. Specifically, such DNA may be cDNA synthesized from mRNA, genomic DNA, or chemically-synthesized DNA. Furthermore, a DNA having an arbitrary nucleotide sequence based on genetic code degeneration is included herein, as long as it encodes the polypeptide of the present invention.

The DNA of the present invention can be prepared by methods known by persons skilled in the art. For example, such DNA can be prepared by constructing a cDNA library from a cell expressing the polypeptide of the present invention and then carrying out hybridization using as a probe a portion of the DNA sequence of the present invention. Such cDNA library may also be prepared by a method described in, for example, relevant literature (Sambrook, J. et al., Molecular Cloning, Cold Spring Harbor Laboratory Press (1989)). Alternatively, a commercial DNA library may also be used. Furthermore, the DNA of the present invention can also be prepared by preparing RNA from a cell expressing the polypeptide of the present invention, synthesizing cDNA using reverse transcriptase, synthesizing oligo DNA based on the DNA sequence of the present invention, carrying out PCR reaction using the resultants as primers, and then amplifying the cDNA that encodes the polypeptide of the present invention.

Moreover, through the determination of the nucleotide sequence of the thus obtained cDNA, a translation region encoded by the sequence can be determined and the amino acid sequence of the polypeptide of the present invention can be obtained. Furthermore, through screening of a genomic DNA library using the thus obtained cDNA as a probe, a genomic DNA can be isolated.

Specifically, the following steps are carried out. First, mRNA is isolated from cells, tissues, and organs expressing the polypeptide of the present invention. To isolate mRNA, total RNA is prepared by a known method such as guanidine ultracentrifugation (Chirgwin, J. M. et al., Biochemistry (1979) 18, 5294-5299) or an AGPC method (Chomczynski, P. and Sacchi, N., Anal. Biochem. (1987) 162, 156-159). mRNA is then purified from the total RNA using a mRNA Purification Kit (Pharmacia Corporation) or the like. In addition, mRNA can also be directly prepared using a QuickPrep mRNA Purification Kit (Pharmacia Corporation).

cDNA is synthesized from the thus obtained mRNA using reverse transcriptase. cDNA can also be synthesized using an AMV Reverse Transcriptase First-strand cDNA Synthesis Kit (SEIKAGAKU CORPORATION) or the like. Furthermore, through the use of primers and the like described in this specification, cDNA synthesis and cDNA amplification can be carried out according to the 5'-RACE method (Frohman, M. A. et al., Proc. Natl. Acad. Sci. U.S.A. (1988) 85, 8998-9002; Belyavsky, A. et al., Nucleic Acids Res. (1989) 17, 2919-2932) using a 5'-Ampli FINDER RACE Kit (produced by Clontech) and polymerase chain reaction (PCR).

A target DNA fragment is prepared from the thus obtained PCR product and then ligated to a vector DNA. Furthermore, a recombinant vector is constructed using the resultant, the recombinant vector is introduced into *Escherichia coli* or the like, and then colonies are selected, thereby preparing a desired recombinant vector. The nucleotide sequence of a target DNA can be confirmed by a known method such as a dideoxy nucleotide chain termination method.

Furthermore, regarding the DNA of the present invention, a nucleotide sequence having higher expression efficiency can be designed in view of the codon usage frequency of a host to be used for expression (Grantham, R. et al., Nucleic Acids Research (1981) 9, r43-74). Moreover, the DNA of the present invention can be altered using a commercial kit or by a known method. Examples of such alteration include digestion with a restriction enzyme, insertion of a synthetic oligonucleotide or an appropriate DNA fragment, addition of a linker, and insertion of an initiation codon (ATG) and/or termination codon (TAA, TGA, or TAG).

The present invention provides a polypeptide encoded by the above DNA of the present invention. The polypeptide of the present invention may differ in amino acid sequence, molecular weight, isoelectric point, or the sugar chain presence, absence, or form, due to the cells or hosts that produce such polypeptide or purification methods as described later. However, the thus obtained polypeptide is included in the present invention, as long as it has functions equivalent to those of the CH fucose transporter polypeptide. For example, when the polypeptide of the present invention is expressed in prokaryotic cells such as *Escherichia coli*, a methionine residue is added to the N-terminus of the amino acid sequence of the original polypeptide. The polypeptide of the present invention also encompasses such polypeptide.

The polypeptide of the present invention can be prepared by a method known by persons skilled in the art as a recombinant polypeptide or a natural polypeptide. Such recombinant polypeptide can be purified and prepared as follows. DNA encoding the polypeptide of the present invention is incorporated into an appropriate expression vector, a transformant that has been obtained by introducing the vector into an appropriate host cell is collected, and then an extract is obtained. Subsequently, the resultant is subjected to chromatography such as ion exchange chromatography, reverse phase chromatography, or gel filtration, affinity chromatography using a column (to which an antibody against the polypeptide of the present invention has been immobilized), or chromatography using combination of a plurality of such columns.

Furthermore, when the polypeptide of the present invention is expressed as a fusion polypeptide with a glutathione-S-transferase protein or as a recombinant polypeptide to which a plurality of histidines have been added in host cells (e.g., animal cells or *Escherichia coli*), the expressed recombinant polypeptide can be purified using a glutathione column or a nickel column. After purification of the fusion polypeptide, if necessary, regions other than the target polypeptide can also be cleaved and removed from the fusion polypeptide using thrombin or factor Xa.

In the case of a natural polypeptide, such polypeptide can be isolated by a method known by persons skilled in the art, such as by causing an affinity column (to which an antibody that binds to the polypeptide of the present invention has been bound as described later) to act on extracts obtained from tissues or cells (e.g., testis) expressing the polypeptide of the present invention for purification. An antibody used herein may be a polyclonal or monoclonal antibody.

The present invention further encompasses partial peptides of the polypeptide of the present invention. Such partial peptides of the present invention can be used for, for example, producing an antibody against the polypeptide of the present invention or screening for a compound that binds to the polypeptide of the present invention.

When used as an immunogen, the partial peptide of the present invention generally consists of an amino acid sequence of at least 7 or more amino acids, preferably 8 or more amino acids, and further preferably 9 or more amino acids. When used as a competitive inhibitor for the polypeptide of the present invention, such partial peptide consists of an amino acid sequence of at least 100 or more amino acids, preferably 200 or more amino acids, and further preferably 300 or more amino acids.

Such partial peptides of the present invention can be produced by a genetic engineering technique known as the peptide synthesis method, or by cleaving the polypeptide of the present invention with appropriate peptidase. Peptides may be synthesized by, for example, either a solid-phase synthesis method or a liquid-phase synthesis method.

The present invention also provides a vector into which the DNA of the present invention is inserted. Such vector of the present invention is useful for retaining the DNA of the present invention within host cells or expressing the polypeptide of the present invention.

For example, when *Escherichia coli* is used as a host, such vector is amplified in large quantities in *Escherichia coli* (e.g., JM109, DH5α, HB101, and XL1Blue) for mass preparation. Hence, vectors used herein are not specifically limited, as long as they have "ori" for amplification in *Escherichia coli* and have a gene for the selection of transformed *Escherichia coli* (e.g., a drug resistance gene that enables distinguishment by the use of a drug such as ampicillin, tetracycline, kanamycin, or chloramphenicol).

Examples of such vector include M13-based vectors, pUC-based vectors, pBR322, pBluescript, and pCR-Script. Furthermore, for the purpose of cDNA subcloning or excision of cDNA, examples of such vector include, in addition to the above vectors, pGEM-T, pDIRECT, and pT7.

When a vector is used for the purpose of producing the polypeptide of the present invention, an expression vector is particularly useful. As an expression vector, for example, when a vector is used for expression in *Escherichia coli*, such vector should have the above characteristics that enable amplification in *Escherichia coli*. Furthermore, when a host is *Escherichia coli* such as JM109, DH5α, HB101, or XL1-Blue, such vector essentially has a promoter that enables efficient expression in *Escherichia coli*, such as a lacZ promoter (Ward et al., Nature (1989) 341, 544-546; FASEB J. (1992) 6, 2422-2427), an araB promoter (Better et al., Science (1988) 240, 1041-1043), or a T7 promoter. Examples of such vector include, in addition to the above vectors, pGEX-5X-1 (produced by Pharmacia Corporation), pQE used in the "QIAexpress system" (produced by QIAGEN), pEGFP, and pET (in this case, a host is preferably BL21 expressing T7 RNA polymerase).

Furthermore, such vector may also contain a signal sequence for polypeptide secretion. As a signal sequence for polypeptide secretion, when polypeptides are produced in periplasms of *Escherichia coli*, a pelB signal sequence (Lei, S. P. et al., J. Bacteriol. (1987) 169, 4379) may be used. Vectors can be introduced into host cells using, for example, a calcium chloride method or an electroporation method.

Microorganisms other than *Escherichia coli* can also be used as hosts for producing the polypeptide of the present invention. In this case, examples of vectors for producing the polypeptide of the present invention include expression vectors derived from mammals (e.g., pcDNA3 (produced by Invitrogen Corporation) and pEGF-BOS (Nucleic Acids. Res.1990, 18(17), p. 5322), pEF, and pCDM8), expression vectors derived from insect cells (e.g., the "Bac-to-BAC baculovirus expression system" (produced by GIBCO-BRL Life Technologies Inc.) and pBacPAK8), expression vectors derived from plants (e.g., pMH1 and pMH2), expression vectors derived from animal viruses (e.g., pHSV, pMV, and pAdexLcw), expression vectors derived from retroviruses (e.g., pZIPneo), expression vectors derived from yeast (e.g., the "Pichia Expression Kit" (produced by Invitrogen Corporation), pNV11, and SP-QO1), and expression vectors derived from *Bacillus subtilis* (e.g., pPL608 and pKTH50).

For the purpose of expression in animal cells such as CHO cells, COS cells, or NIH3T3 cells, a vector used herein essentially has a promoter required for expression within cells, such as an SV40 promoter (Mulligan et al., Nature (1979) 277, 108), an MMLV-LTR promoter, an EF1α promoter (Mizushima et al., Nucleic Acids Res. (1990) 18, 5322), or a CMV promoter. It is further preferable that such vector has a gene for selection of transformed cells (e.g., a drug resistance gene that enables distinguishment by the use of a drug (e.g., neomycin and G418)). Examples of a vector having such properties include pMAM, pDR2, pBK-RSV, pBK-CMV, pOPRSV, and pOP13.

Furthermore, an example of a method for the purpose of stable expression of a gene and amplification of the number of copies of a gene within cells involves introducing a vector (e.g., pCHOI) having a complementary DHFR gene into CHO cells lacking the nucleic acid synthesis pathway, followed by amplification using methotrexate (MTX). Furthermore, an example of a method for the purpose of transient expression of a gene involves transforming COS cells having a gene that expresses SV40 T antigen on the chromosome with a vector (e.g., pcD) having an SV40 replication origin. As a replication initiation site, a site derived from polyoma virus, adenovirus, bovine papilloma virus (BPV), or the like can also be used. Furthermore, to amplify the number of copies of a gene in a host cell system, an expression vector may contain as a selection marker an aminoglycoside transferase (APH) gene, thymidine kinase (TK) gene, *Escherichia coli* xanthine-guanine phosphoribosyltransferase (Ecogpt) gene, dihydrofolate reductase (dhfr) gene, or the like.

In the meantime, examples of a method for expressing in vivo the DNA of the present invention within animals involves incorporating the DNA of the present invention into an appropriate vector and then introducing the vector into an animal body by, for example, a retrovirus method, a liposome method, a cationic liposome method, or an adenovirus method. Examples of vectors used herein include, but are not limited to, adenovirus vectors (e.g., pAdexlcw) and retrovirus vectors (e.g., pZIPneo). General genetic engineering techniques including, for example, insertion of the DNA of the present invention into a vector can be carried out according to a standard method (Molecular Cloning, 5.61-5.63). Administration into living bodies may be carried out by an ex vivo method or an in vivo method.

Furthermore, the present invention provides a host cell having the vector of the present invention introduced therein. Such host cell into which the vector of the present invention is introduced is not specifically limited. For example, *Escherichia coli*, various animal cells, or the like can be used. Such host cell of the present invention can be used as, for example, a production system for producing or expressing the polypeptide of the present invention. As such a production system for producing a polypeptide, in vitro and in vivo production systems can be employed. Examples of an in vitro production system include a production system using eukaryotic cells and a production system using prokaryotic cells.

When eukaryotic cells are used, animal cells, plant cells, and fungal cells, for example, can be used as hosts. As animal cells, mammalian cells such as CHO (J. Exp. Med. (1995) 108, 945), COS, 3T3, myeloma, BHK (baby hamster kidney), HeLa, and Vero are known. As amphibian cells, Xenopus oocytes (Valle, et al., Nature (1981) 291, 358-340), for example, are known. As insect cells Sf9, Sf21, and Tn5, for example, are known. As CHO cells, in particular, dhfr-CHO cells (Proc. Natl. Acad. Sci. U.S.A. (1980) 77, 4216-4220) or CHO K-1 cells (Proc. Natl. Acad. Sci. U.S.A. (1968) 60, 1275), which are deficient in a DHFR gene, can be preferably used. For the purpose of mass-expression in animal cells, CHO cells are particularly preferable. A vector can be introduced into a host cell by, for example, a calcium phosphate method, a DEAE dextran method, a method using cationic ribosome DOTAP (produced by Boehringer Mannheim), an electroporation method, or lipofection.

As plant cells *Nicotiana tabacum*-derived cells, for example, are known to comprise a polypeptide production system. Polypeptides can be obtained by culturing the calli of *Nicotiana tabacum*-derived cells. As fungal cells, yeast such as that of the genus *Saccharomyces* (e.g., *Saccharomyces cerevisiae*) and filamentous bacteria such as those of the genus *Aspergillus* (e.g., *Aspergillus niger*) are known.

When prokaryotic cells are used, a production system using bacterial cells may be employed. Examples of bacterial cells include *Escherichia coli* (*E. coli*) such as JM109, DH5α, and HB101. In addition, *Bacillus subtilis* is also known.

Polypeptides can be obtained by transforming these cells with a target DNA and then culturing in vitro the thus transformed cells. Culture can be carried out according to a known method. As a culture solution for animal cells, DMEM, MEM, RPMI1640, or IMDM, for example, can be used. At this time, a serum fluid such as fetal calf serum (FCS) can be used together therewith. Alternatively serum-free culture may also be carried out. pH during culture is preferably between approximately 6 and 8. Culture is generally carried out at approximately 30° C. to 40° C. for approximately 15 to 200 hours. If necessary, exchange of media, aeration, and agitation are carried out.

Meanwhile, examples of systems for in vivo production of polypeptides include production systems using animals and production systems using plants. Target DNA is introduced into these animals or plants, polypeptides are produced in vivo within the animals or the plants, and then the polypeptides are collected. The term "host" in the present invention encompasses these animals and plants.

When animals are used, there are production systems using mammals and production systems using insects. As mammals, goats, pigs, sheep, mice, or cattle can be used (Vicki Glaser, SPECTRUM Biotechnology Applications, 1993). Furthermore, when mammals are used, transgenic animals can be used.

For example, a target DNA is prepared in the form of a fusion gene with a gene encoding a polypeptide such as goat β casein that is uniquely produced in milk. Subsequently, a DNA fragment comprising the fusion gene is injected into a goat embryo and then the embryo is transplanted into a female goat. A target polypeptide can be obtained from milk that is produced by transgenic goats born from goats that have accepted such embryos, or from the progenies of such transgenic goats. To increase the amount of milk containing polypeptides, which is produced by transgenic goats, an appropriate hormone may also be used for such transgenic goats (Ebert, K. M. et al., Bio/Technology (1994) 12, 699-702).

Furthermore, as insects, silkworm, for example, can be used. When silkworms are used, a target polypeptide can be obtained from the body fluid of a silkworm by infecting the silkworm with a baculovirus wherein a DNA encoding the target polypeptide has been inserted (Susumu, M. et al., Nature (1985) 315, 592-594).

Furthermore, when plants are used, tobacco, for example, can be used. When tobacco is used, a DNA encoding a target polypeptide is inserted into an expression vector for a plant, such as pMON 530, and then the vector is introduced into bacteria such as *Agrobacterium tumefaciens*. Tobacco such as *Nicotiana tabacum* is infected with such bacteria and then the desired polypeptide can be obtained from the tobacco leaves (Julian K.-C. Ma et al., Eur. J. Immunol. (1994) 24, 131-138).

The polypeptide of the present invention that is obtained by such method can be isolated from within host cells or outside the cells (e.g., media) and then purified as a substantially pure and uniform polypeptide. To separate and purify polypeptides, separation and purification methods that are generally used for polypeptide purification may be employed and are not specifically limited. For example, polypeptides can be separated and purified by the use of appropriate selection and combination of a chromatography column, a filter, ultrafiltration, salting-out, solvent precipitation, solvent extraction, distillation, immunoprecipitation, SDS-polyacrylamide gel electrophoresis, an isoelectric focusing method, dialysis, recrystallization, and the like.

Examples of chromatography include affinity chromatography, ion exchange chromatography, hydrophobic chromatography, gel filtration, reverse phase chromatography, and adsorption chromatography (Strategies for Protein Purification and Characterization: A Laboratory Course Manual, Ed Daniel R. Marshak et al., Cold Spring Harbor Laboratory Press, 1996). These types of chromatography can be carried out using liquid-phase chromatography such as HPLC or FPLC. The present invention also encompasses polypeptides that are purified at high levels using these purification methods.

In addition, when a proper protein modification enzyme is caused to act on polypeptides before or after purification, modification can be arbitrarily carried out or peptides can be partially removed. As protein modification enzymes, trypsin, chymotrypsin, lysylendopeptidase, protein kinase, and glucosidase, for example, are used.

The present invention also provides an antibody that binds to the polypeptide of the present invention. Examples of forms of such antibodies of the present invention include, but are not specifically limited to, monoclonal antibodies and polyclonal antibodies. Moreover, the origins of such antibodies are not limited. Any antibodies may be used, such as mouse antibodies, rat antibodies, rabbit antibodies, camel antibodies, and human antibodies. Furthermore, chimeric antibodies or humanized antibodies produced by genetic recombination are also included in the antibodies of the present invention.

Polypeptides that are used as sensitizing antigens in the present invention may be complete proteins or partial peptides of a protein. Examples of such partial peptides of a protein include amino group (N)-terminal fragments or carboxyl (C) terminal fragments of a protein. "Antibody" in this specification means an antibody that reacts with the full-length protein or a fragment thereof.

A gene encoding the polypeptide or a fragment thereof of the present invention is inserted into a known expression vector system. Host cells described in this specification are transformed with the vector and then the target polypeptide or a fragment thereof is obtained by a known method from the inside or the outside of the host cells. Such polypeptide or fragment may be used as a sensitizing antigen. Moreover, a cell expressing the polypeptide, a lysate of such cells, or a chemically synthesized polypeptide of the present invention can also be used as a sensitizing antigen. Preferably, a short peptide is appropriately bound to a carrier protein such as keyhole limpet hemocyanin, bovine serum albumin, or ovalbumin, so as to prepare an antigen.

Mammals to be immunized with such sensitizing antigen are not specifically limited. Preferably, mammals are selected in view of compatibility with a parent cell to be used for cell fusion. In general, animals of the order Rodentia, the order Lagomorpha, or the order Primates are used.

As animals of the order Rodentia, mice, rats, and hamsters, for example, are used. As animals of the order Lagomorpha, rabbits, for example, are used. As animals of the order Primates, monkeys, for example, are used. As such monkeys, monkeys of the order Catarrhini (Monkeys of the Old World), such as crab-eating monkeys, Rhesus monkeys, Hamadryas baboons, and chimpanzees are used.

Animals are immunized with a sensitizing antigen according to a known method. In a general method, a sensitizing antigen is intraperitoneally or subcutaneously injected into mammals. Specifically, a sensitizing antigen is diluted and suspended to an appropriate amount using PBS (Phosphate-Buffered Saline) or physiological saline. If desired, a general adjuvant such as Freund's complete adjuvant is mixed in an appropriate amount with the suspension. After emulsification, the resultant is administered to mammals. Furthermore, it is preferable to administer the sensitizing antigen (which has been mixed in an appropriate amount with Freund's incomplete adjuvant) several times over a period of every 4 to 21 days. Furthermore, at the time of immunization with a sensitizing antigen, an appropriate carrier can be used. Immunization is carried out as described above. An increase in the desired antibody level in serum is confirmed by a standard method.

Here, to obtain a polyclonal antibody against the polypeptide of the present invention, after confirmation of an increase in the desired antibody level in serum, blood of mammals that have been sensitized with the antigen is collected. Serum is separated from the blood by a known method. As polyclonal antibodies, serum containing polyclonal antibodies may also be used. If necessary, a fraction containing polyclonal antibodies may be further isolated from the serum and then used. For example, immunoglobulin G or M can be prepared by obtaining a fraction for recognition of only the polypeptide of the present invention using an affinity column (with which the polypeptide of the present invention has been coupled) and then purifying the fraction using a protein A column or a protein G column.

To obtain a monoclonal antibody, after confirmation of an increase in the desired antibody level in the serum of a mammal that has been sensitized with the above antigen, immunocytes are removed from the mammal and then subjected to cell fusion. At this time, a particularly preferable example of such an immunocyte to be used for cell fusion is a spleen cell. The other (parent) cell to be fused with the above immunocyte is preferably a mammalian myeloma cell and more preferably a myeloma cell that has acquired properties for the selection of the resultant fusion cells through the use of a drug.

Cell fusion of the above immunocyte with a myeloma cell can be carried out according to basically a known method such as Milstein et al.'s method (Galfre, G. and Milstein, C., Methods Enzymol. (1981) 73, 3-46).

Hybridomas obtained by cell fusion are selected by culture in a general culture solution for selection, such as an HAT culture solution (culture solution containing hypoxanthine, aminopterin, and thymidine). Culture in such an HAT culture solution is continued for a time sufficient for cells (unfused cells) other than the target hybridomas to die. In general, culture is carried out for several days to several weeks. Next, a general limiting dilution method is conducted. Then, screening for and cloning of hybridomas that produce a target antibody are carried out.

The above hybridomas are obtained by immunizing non-human animals with an antigen. In addition to this method, hybridomas that produce a desired human antibody having activity of binding to a polypeptide can also be obtained by in vitro sensitization of human lymphocytes, such as human lymphocytes that have been infected with the EB virus, with a polypeptide, a polypeptide-expressing cell, or a lysate thereof, followed by fusing of the thus sensitized lymphocytes with myeloma cells having a human-derived ability to permanently divide, such as U266 (JP Patent Publication (Kokai) No. 63-17688 A (1988)).

Subsequently, the thus obtained hybridomas are transplanted into a mouse abdominal cavity and then ascite is collected from the mouse. The thus obtained monoclonal antibody can be prepared by purification using, for example, an ammonium sulfate precipitation, a protein A column, a protein G column, DEAE ion exchange chromatography, or an affinity column with which the polypeptide of the present invention has been coupled. Such antibody of the present invention is also used for purification or detection of the polypeptide of the present invention, and is used as a candidate of an agonist or an antagonist of the polypeptide of the present invention.

For the purpose of, for example, lowering heterologous antigenicity against humans, artificially altered gene recombinant antibody such as a chimeric antibody or a humanized antibody can be appropriately used. Such gene recombinant antibodies can be produced using a known method. A chimeric antibody comprises the variable region of the heavy and light chains of an antibody of a non-human mammal such as a mouse and the constant region of the heavy and light chains of a human antibody. DNA encoding the variable region of a mouse antibody is ligated to DNA encoding the constant region of a human antibody. The resultant is incorporated into an expression vector, and then the vector is introduced into a host to cause the host to produce the gene product. Thus a gene recombinant antibody can be obtained. A humanized antibody is also referred to as a reshaped human antibody. A humanized antibody is obtained by transplanting the complementarity determining region (CDR) of an antibody of a non-human mammal such as a mouse into the complementarity determining region of a human antibody. General gene recombination techniques therefor are also known. Specifically, DNA sequences designed to have the CDR of a mouse antibody ligated to the framework region (FR) of a human antibody are synthesized by the PCR method from several oligonucleotides, adjacent oligonucleotides of which have an overlap region at their terminal portions. The thus obtained DNA is ligated to DNA encoding the constant region of a human antibody, the resultant is incorporated into an expression vector, and then the vector is introduced into a host to cause the host to produce the gene product, so that a gene recombinant antibody can be obtained (see European Patent Application Publication No. EP 239400 and International Patent Application Publication No. WO 96/02576). As the FR of a human antibody, which is ligated via CDR, FR that allows the formation of an antigen-binding site with a good complementarity determining region is selected. If necessary, for the formation of an antigen-binding site having the appropriate complementarity determining region of a reshaped human antibody, the amino acids of the framework region of an antibody variable region may be substituted (Sato, K. et al., Cancer Res, 1993, 53, 851-856. ). Furthermore, methods for obtaining human antibodies are also known. For example, a desired human antibody having activity of binding to an antigen can also be obtained by sensitizing a human lymphocyte in vitro with a desired antigen or a cell that expresses a desired antigen and then fusing the sensitized lymphocyte to a human myeloma cell such as U266 (see JP Patent Publication (Kokoku) No. 1-59878 B (1989)). Moreover, a desired human antibody can be obtained by immunizing a transgenic animal that has all the repertoires of a human antibody gene with a desired antigen (see International Patent Application Publication No. WO93/12227, WO92/03918, WO94/02602, WO94/25585, WO96/34096, and WO96/33735). Furthermore, a technique is also known by which a human antibody is obtained by panning using a human antibody library. For example, the variable region of a human antibody is expressed as a single chain antibody (scFv) on the surface of a phage by a phage display method. A phage that binds to an antigen can be selected. A DNA sequence encoding the variable region of a human antibody that binds to the antigen can be determined by analyzing the gene of the thus selected phage. When the DNA sequence of scFv that binds to an antigen is revealed, an appropriate expression vector is constructed based on the sequence, and then a human antibody can be obtained. These methods are already known. Concerning these methods, WO92/01047, WO92/20791, WO93/06213, WO93/11236, WO93/19172, WO95/01438, and WO95/15388 can be referred to.

Furthermore, the antibody of the present invention may be an antibody fragment or a modified antibody product, as long as it binds to the polypeptide of the present invention. Examples of such antibody fragment include Fab, F(ab')$_2$, Fv, or single chain Fv(scFv) wherein Fv of the H chain and Fv of the L chain are linked using an appropriate linker (Huston, J. S. et al., Proc. Natl. Acad. Sci. U.S.A. (1988) 85, 5879-5883), and a diabody. Specifically, an antibody is treated with an enzyme such as papain or pepsin to generate antibody fragments. Alternatively, a gene encoding such antibody fragment is constructed, the gene is introduced into an expression vector, and then the gene is expressed in an appropriate host cell (e.g., see Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137). A diabody is prepared by dimerization; specifically, by linking two fragments (e.g., scFv), each of which is prepared by linking two variable regions using a linker or the like (hereinafter, referred to as a fragment composing a diabody). Generally, a diabody contains two VLs and 2 VHs (P. Holliger et al., Proc. Natl. Acad. Sci. U.S.A. 90, 6444-6448 (1993); EP404097; WO93/11161; Johnson et al., Methods in Enzymology, 203, 88-98, (1991); Holliger et al., Protein Engineering, 9, 299-305, (1996); Perisic et al., Structure, 2, 1217-1226, (1994); John et al., Protein Engineering, 12(7), 597-604, (1999); Holliger et al., Proc. Natl. Acad. Sci. U.S.A. 90, 6444-6448, (1993); and Atwell et al., Mol. Immunol. 33, 1301-1312, (1996)).

As a modified product of an antibody, antibodies to which various molecules such as polyethylene glycol (PEG) have been bound can also be used. The term "antibody" of the present invention also encompasses such modified product of an antibody. Such modified products of an antibody can be obtained by chemically modifying an obtained antibody. Methods therefor have already been established in the field.

Antibodies obtained as described above can be purified to a uniform level. To separate and purify antibodies used in the present invention, separation and purification methods that are generally used for polypeptides may be used. Antibodies can be separated and purified by appropriate selection or combination of, for example, a column for chromatography such as affinity chromatography, a filter, ultrafiltration, salting-out, dialysis, SDS-polyacrylamide gel electrophoresis, and an isoelectric focusing method (Antibodies: A Laboratory Manual, Ed Harlow and David Lane, Cold Spring Harbor Laboratory, 1988). However, methods for separation and purification are not limited to the above methods. The concentrations of antibodies obtained above can be measured by absorbance measurement, enzyme-linked immunosorbent assay (ELISA), or the like.

Examples of a column to be used for affinity chromatography include a protein A column and a protein G column. Examples of a column using protein A include Hyper D, POROS, and Sepharose F. F. (Pharmacia).

Examples of chromatography other than affinity chromatography include ion exchange chromatography, hydrophobic chromatography, gel filtration, reverse phase chromatography, and adsorption chromatography (Strategies for Protein Purification and Characterization: A Laboratory Course Manual, Ed Daniel R. Marshak et al., Cold Spring Harbor Laboratory Press, 1996). These types of chromatography can be carried out using liquid-phase chromatography such as HPLC or FPLC.

As a method for measuring the antigen-binding activity of the antibody of the present invention, absorbance measurement, ELISA (enzyme-linked immunosorbent assay), EIA (enzyme-linked immunoassay), RIA (radioimmunoassay), or a fluorescent antibody technique can be used, for example, when ELISA is used, the polypeptide of the present invention is added to a plate to which the antibody of the present invention has been immobilized and then a sample containing a target antibody, such as the culture supernatant of antibody-producing cells or a purified antibody, is added. A secondary antibody that recognizes an antibody labeled with an enzyme such as alkaline phosphatase is added and then the plate is incubated. After washing, an enzyme substrate such as p-nitrophenyl phosphate is added and then absorbance is measured, so that antigen-binding activity can be evaluated. As a polypeptide, a polypeptide fragment such as a fragment comprising the C-terminus of the polypeptide may also be used. For evaluation of the activity of the antibody of the present invention, BIAcore (produced by Pharmacia) can be used.

The method for detecting or measuring the polypeptide of the present invention comprises contacting the antibody of the present invention with a sample that presumably contains the polypeptide of the present invention and detecting or measuring an immune complex of the antibody and the polypeptide. Through the use of these techniques, the method for detecting or measuring the polypeptide of the present invention can be conducted. The method for detecting or measuring the polypeptide of the present invention enables specific detection or measurement of polypeptides. Hence, the method is useful in various experiments and the like using polypeptides.

The present invention also provides DNA encoding the CH fucose transporter polypeptide or a polynucleotide comprising at least 15 nucleotides complementary to a complementary strand of the DNA.

Here "complementary strand" indicates a strand that is complementary to the other strand when the two strands form a double-strand nucleic acid; that is, a base pair consisting of A:T (in the case of RNA, "U") or a base pair consisting of G:C. Furthermore, "complementary" is not limited to a case where a sequence is completely complementary to a sequence in terms of a region consisting of at least 15 sequential nucleotides. A complementary sequence that can be used herein has at least 70%, preferably at least 80%, more preferably 90%, and further preferably 95% or more homology in terms of nucleotide sequence. As algorithm for the determination of homology, the algorithm described in this specification may be used.

Antisense oligonucleotides used in the present invention may be single-stranded, double-stranded, or greater number-stranded.

Nucleotides may be DNA, RNA, or mixtures of DNA and RNA.

Such nucleic acid can be used for probes and primers to be used for detecting or amplifying DNA that encodes the polypeptide of the present invention, probes and primers to be used for detecting the expression of such DNA, production of DNA chips, and the like.

Moreover, nucleotides or nucleotide derivatives (e.g., an antisense oligonucleotide, a ribozyme, or DNAs encoding them) for controlling the expression of the polypeptide of the present invention are included. When the expression of the polypeptide of the present invention is inhibited, a target site therefor is not specifically limited. A protein-coding region, a 5' untranslation region, or the like can be targeted. For example, an antisense oligonucleotide that inhibits the expression of the polypeptide of the present invention can inhibit fucose transport into the Golgi apparatus in CHO cells, so as to be able to inhibit the addition of fucose to an antibody. Thus, such antisense oligonucleotide is useful for production of an antibody having high cytotoxic activity, and the like.

When used as a primer, the 3' side region is designed to be a complementary region, and a restriction enzyme recognition sequence, a tag, or the like can be added to the 5' side.

An example of an antisense oligonucleotide is an antisense oligonucleotide that hybridizes to any position in the nucleotide sequence of SEQ ID NO: 1 or a complementary sequence thereof. Preferably, such antisense oligonucleotide corresponds to at least 15 sequential nucleotides in the nucleotide sequence of SEQ ID NO: 1. Further preferably, such antisense oligonucleotide is characterized in that at least 15 sequential nucleotides contain a translation initiation codon. Specific hybridization conditions are, for example, the above conditions.

As antisense oligonucleotides, derivatives or modified products thereof can be used. Examples of such modified products include methylphosphonate-type or ethylphosphonate-type products such as modified lower alkyl phosphonate, modified phosphorothioate, and modified phosphoroamidate.

Examples of such antisense oligonucleotides include not only antisense oligonucleotides (wherein all the nucleotides corresponding to the nucleotides that compose a predetermined region of DNA or mRNA form a complementary sequence), but also include, as long as DNA or mRNA and oligonucleotides can specifically hybridize to the nucleotide sequence represented by SEQ ID NO: 1, oligonucleotides wherein a mismatch of 1 or a plurality of nucleotides is present.

The antisense oligonucleotide derivative of the present invention acts on cells that produce the polypeptide of the present invention and binds to DNA or mRNA encoding the polypeptide, thereby inhibiting transcription or translation and promoting mRNA degradation. As a result of suppression of the expression of the polypeptide of the present invention, the derivative has an effect of suppressing the action of the polypeptide of the present invention.

When RNA is used as an oligonucleotide, a phenomenon that is generally referred to as RNA interfearence (RNAi) takes place. RNAi is a phenomenon whereby when double-strand RNA (dsRNA) is introduced into a cell, intracellular mRNA corresponding to the RNA sequence is specifically degraded so that the gene is not expressed as protein. In the case of RNAi, double-strand RNA is generally used, but RNAi is not limited thereto. For example, double strands that are formed in self-complementary single-strand RNAs can also be used. Regarding regions where double strands are formed, double strands may be formed in all the regions or single strands or the like may be formed in partial regions (e.g., both ends or one end). The length of oligo RNA to be used for RNAi is not limited. The length of the oligo RNA of the present invention is, for example, 5 to 1000 nucleotides (in the case of double strands, 5 to 1000 bp), preferably 10 to 100 nucleotides (in the case of double strands, 10 to 100 bp), further preferably 15 to 25 nucleotides (in the case of double strands, 15 to 25 bp), and particularly preferably 19 to 23 nucleotides (in the case of double strands, 19 to 23 bp).

Furthermore, the present invention provides a method for screening for a compound that binds to the polypeptide of the present invention. Such method comprises contacting the polypeptide of the present invention with a sample to be tested that presumably contains a compound binding to the polypeptide, detecting binding activity between the polypeptide and the sample to be tested, and then selecting the compound that has activity of binding to the polypeptide of the present invention.

Furthermore, the present invention provides a method for screening for a substance that inhibits the fucose transport activity, and particularly the GDP-fucose transport activity, of the polypeptide of the present invention. Such method comprises contacting the polypeptide of the present invention with a sample to be tested, detecting the fucose transport activity of the polypeptide of the present invention, and then selecting a compound that inhibits the fucose transport activity of the polypeptide of the present invention.

The polypeptide of the present invention that is used for screening may be a recombinant polypeptide, a polypeptide derived from nature, or a partial peptide. Furthermore, the polypeptide of the present invention to be used for screening may be in a form whereby it is expressed on the cell surface or the form of a membrane fraction. Examples of a sample to be tested are not specifically limited and include cell extracts, cell culture supernatants, products of fermentation microorganisms, extracts of marine organisms, plant extracts, purified or crudely purified polypeptides, non-peptide compounds, synthetic low molecular weight compounds, and natural compounds. The polypeptide of the present invention (that is contacted with such sample to be tested) can be contacted in the form of, for example, a purified polypeptide, a soluble polypeptide, a polypeptide bound to a carrier, a polypeptide that is fused with another polypeptide, a polypeptide expressed on the cell membrane, or a membrane fraction, with a sample to be tested.

As a method for screening for a polypeptide that binds to the polypeptide of the present invention, many methods known by persons skilled in the art can be used. Such screening can be carried out by an immunoprecipitation method, for example. Specifically, such screening can be carried out as follows. A gene encoding the polypeptide of the present invention is inserted into a vector for expressing a foreign gene, such as pSV2neo, pcDNA I, or pCD8, so that the gene is expressed in animal cells or the like. As promoters to be used for expression, any promoters that can be generally used can be used. Examples of such promoter include an SV40 early promoter (Rigby In Williamson (ed.), Genetic Engineering, Vol.3. Academic Press, London, p.83-141 (1982)), an EF-1α promoter (Kim et al., Gene 91, pp. 217-223 (1990)), a CAG promoter (Niwa et al. Gene 108, pp. 193-200 (1991)), an RSV LTR promoter (Cullen Methods in Enzymology 152, pp. 684-704 (1987)), an SRa, promoter (Takebe et al. Mol. Cell. Biol. 8, p. 466 (1988)), a CMV immediate early promoter (Seed and Aruffo Proc. Natl. Acad. Sci. U.S.A. 84, pp. 3365-3369 (1987)), an SV40 late promoter (Gheysen and Fiers, J. Mol. Appl. Genet. 1, pp. 385-394 (1982)), an Adenovirus late promoter (Kaufman et al. Mol. Cell. Biol. 9, p. 946 (1989)), and an HSV TK promoter.

Examples of a method for expressing a foreign gene by introducing the gene into animal cells include an electroporation method (Chu, G. et al., Nucl. Acid Res. 15, 1311-1326 (1987)), a calcium phosphate method (Chen, C and Okayama, H. Mol. Cell. Biol. 7, 2745-2752 (1987)), a DEAE dextran method (Lopata, M. A. et al., Nucl. Acids Res. 12, 5707-5717 (1984); Sussman, D. J. and Milman, G., Mol. Cell. Biol. 4, 1642-1643 (1985)), and a lipofectin method (Derijard, B., Cell 7, 1025-1037 (1994); Lamb, B. T. et al., Nature Genetics 5, 22-30 (1993); Rabindran, S. K. et al., Science 259, 230-234 (1993)). Any of these methods may be employed.

The polypeptide of the present invention can be expressed as a fusion polypeptide by introducing a recognition site (epitope) of a monoclonal antibody, the specificity of which has been clarified, into the N- or C-terminus of the polypeptide of the present invention. As an epitope-antibody system to be used herein, a commercial system can be used (Experimental Medicine 13, 85-90 (1995)). A vector that enables expression of a fusion polypeptide with β-galactosidase, a maltose-binding protein, glutathione-S-transferase, a green fluorescent protein (GFP), or the like via a multi-cloning site is marketed.

To keep the properties of the polypeptide of the present invention unchanged as far as possible when it is prepared in the form of a fusion polypeptide, a method has been reported wherein only a small epitope portion consisting of several to more than a dozen amino acids is introduced, so as to prepare a fusion polypeptide. For example, epitopes such as polyhistidine (His-tag), influenza hemagglutinin HA, human c-myc, FLAG, a vesicular stomatitis virus glycoprotein (VSV-GP), a T7 gene 10 protein (T7-tag), a human herpes simplex virus glycoprotein (HSV-tag), and an E-tag (an epitope on a monoclonal phage) and monoclonal antibodies that recognize such epitopes can be used as epitope-antibody systems for screening for polypeptides that bind to the polypeptide of the present invention (Experimental Medicine 13, 85-90 (1995)).

In immunoprecipitation, such antibody is added to a cell lysis solution prepared using an appropriate surfactant, so as to form an immune complex. The immune complex comprises the polypeptide of the present invention, a polypeptide capable of binding thereto, and an antibody. In addition to the use of an antibody against the above epitope, immunoprecipitation can also be carried out using an antibody against the polypeptide of the present invention. Such antibody against the polypeptide of the present invention can be prepared by, for example, introducing a gene encoding the polypeptide of the present invention into an appropriate *Escherichia coli* expression vector for expression within *Escherichia coli*, purifying the thus expressed polypeptide, and then immunizing rabbits, mice, rats, goats, chickens, or the like with the polypeptide. Moreover, such antibodies can also be prepared by immunizing a partial peptide of the synthesized polypeptide of the present invention with the above animals.

Immune complexes can be precipitated using Protein A Sepharose or Protein G Sepharose, for example, if antibodies are mouse IgG antibodies. Furthermore, when the polypeptide of the present invention is prepared as, for example, a fusion polypeptide with an epitope such as GST, an immune complex can also be formed using a substance such as glutathione Sepharose 4B that specifically binds to such epitope in a manner similar to that in a case where an antibody of the polypeptide of the present invention is used.

General methods for immunoprecipitation can be carried out by or according to, for example, a method described in literature (Harlow, E. and Lane, D.:.Antibodies, pp. 511-552, Cold Spring Harbor Laboratory Publications, New York (1988)).

SDS-PAGE is generally employed for the analysis of immunoprecipitated polypeptides. Through the use of gel with an appropriate concentration, a bound polypeptide can be analyzed based on the molecular weight of the polypeptide. At this time, it is generally difficult to detect such polypeptide that has bound to the polypeptide of the present invention by a general staining method for polypeptides, such as Coomassie staining or silver staining. Detection sensitivity can be improved by culturing cells in a culture solution containing $^{35}$S-methionine or $^{35}$S-cysteine, which is a radioactive isotope, so as to label polypeptides within the cells and then detecting them. If the molecular amount of a polypeptide is revealed, such target polypeptide can be directly purified from SDS-polyacrylamide gel and then the sequence thereof can also be determined.

Furthermore, as a method for isolating a polypeptide that binds to the polypeptide of the present invention, a West western blotting method (Skolnik, E. Y. et al., Cell (1991) 65, 83-90), for example, can be employed. Specifically, a cDNA library is constructed from cells, tissues, or organs (e.g., testis) that are predicted to express a polypeptide that binds to the polypeptide of the present invention using a phage vector (e.g., λgt11 and ZAP). The resultant is then expressed on LB-agarose and then the expressed polypeptide is immobilized on a filter. The purified and labeled polypeptide of the present invention is caused to react with the above filter. Subsequently, plaques expressing polypeptides binding to the polypeptide of the present invention are detected based on the labels. Examples of a method for labeling the polypeptide of the present invention include a method using binding between biotin and avidin, a method using an antibody that specifically binds to the polypeptide of the present invention or a polypeptide (e.g., GST) fusing with the polypeptide of the present invention, a method using a radioisotope, and a method using fluorescence.

Another embodiment of the screening method of the present invention is a method that is conducted using a 2-hybrid system using cells (Fields, S., and Sternglanz, R., Trends. Genet. (1994) 10, 286-292; Dalton S, and Treisman R (1992), Characterization of SAP-1, a protein recruited by serum response factor to the c-fos serum response element., Cell 68, 597-612; "MATCHMARKER Two-Hybrid System," "Mammalian MATCHMAKER Two-Hybrid Assay Kit," "MATCHMAKER One-Hybrid System" (these systems and kits are all produced by Clontech), and "HybriZAP Two-Hybrid Vector System" (produced by Stratagene Corp.)).

In the 2-hybrid system, the polypeptide of the present invention or a partial peptide thereof is fused with an SRF DNA-binding region or a GAL4 DNA-binding region and then the product is expressed in yeast cells. A cDNA library that is expressed while being fused with a VP16 or GAL4 transcription activation region is constructed from cells that are predicted to express a polypeptide binding to the polypeptide of the present invention. The cDNA library is then introduced into the above yeast cells. A library-derived cDNA is isolated from a detected positive clone. (A positive clone can be confirmed when a polypeptide that binds to the polypeptide of the present invention is expressed within a yeast cell, following which a reporter gene is activated because of the binding of the two.) By introducing the isolated cDNA into *Escherichia coli* for expression, the polypeptide encoded by the cDNA can be obtained. Accordingly, a polypeptide that binds to the polypeptide of the present invention or the gene thereof can be prepared.

Examples of a reporter gene to be used in the 2-hybrid system include, but are not limited to, in addition to an HIS3 gene, an Ade2 gene, a LacZ gene, a CAT gene, a luciferase gene, and a PAI-1 (Plasminogen activator inhibitor type 1) gene. Screening by the 2-hybrid method can also be carried out using mammalian cells in addition to yeast.

A compound that binds to the polypeptide of the present invention can also be screened for using affinity chromatography. For example, the polypeptide of the present invention is immobilized to a carrier of an affinity column and then a sample to be tested, which is predicted to express a polypeptide that binds to the polypeptide of the present invention, is applied. Examples of a sample to be tested in this case include a cell extract and a cell lysate. After application of a sample to be tested, the column is washed, and then a polypeptide that has bound to the polypeptide of the present invention can be prepared.

The amino acid sequence of the thus obtained polypeptide is analyzed and then an oligo DNA is synthesized based on the sequence. A DNA encoding the polypeptide can be obtained by screening a cDNA library using the DNA as a probe.

Furthermore, an example of a method for isolating not only a polypeptide but also a compound (including agonists and antagonists) that binds to the polypeptide of the present invention, which is known by persons skilled in the art, is a method that involves causing a synthetic compound, a natural product bank, or a random phage peptide display library to act on the immobilized polypeptide of the present invention and then screening for a molecule that binds to the polypeptide of the present invention, or a screening method using high throughput based on combinatorial chemistry technology (Wrighton N C; Farrell F X; Chang R; Kashyap A K; Barbone F P; Mulcahy L S; Johnson D L; Barrett R W; Jolliffe L K; Dower W J., Small peptides as potent mimetics of the protein hormone erythropoietin, Science (UNITED STATES) Jul. 26 1996, 273, pp. 458-64; Verdine G L., The combinatorial chemistry of nature, Nature (ENGLAND) Nov. 7 1996, 384, pp. 11-13; Hogan J C Jr., Directed combinatorial chemistry, Nature (ENGLAND) Nov. 7 1996, 384, pp. 17-9).

In the present invention, a biosensor using the surface plasmon resonance phenomenon can also be used as a means for detecting or measuring bound compounds. With such a biosensor, interaction between the polypeptide of the present invention and a compound to be tested can be observed in real time as surface plasmon resonance signals using a fine amount of polypeptides without labeling them (e.g., produced by BIAcore or Pharmacia). Hence, by the use of a biosensor produced by BIAcore or the like, binding between the polypeptide of the present invention and a compound to be tested can be evaluated.

A method for screening for a substance that inhibits the fucose transport activity of the polypeptide of the present invention can be carried out by a method known by persons skilled in the art. For example, the polypeptide of the present invention is expressed on a membrane (e.g., cell membrane, Golgi apparatus membrane, or viral membrane). Fucose labeled with a fluorescent substance or the like is contacted with a substance to be tested and then the amount of incorporated fucose is measured. Thus, a substance that inhibits the fucose transport activity of the polypeptide of the present invention can be screened for.

A compound that can be isolated by the screening according to the present invention is a candidate for regulating the activity of the polypeptide of the present invention and may be applied for the production of an antibody with high cytotoxic activity.

"Fucose transporter" in the present invention means a polypeptide having fucose transport activity. For example, when a fucose transporter is expressed on the cell membrane, it generally incorporates fucose into the cells. When a fucose transporter is expressed on the Golgi membrane, it generally incorporates fucose into the Golgi apparatus. In the present invention, a preferable fucose transporter is a Chinese hamster fucose transporter, and a more preferable example is a fucose transporter having the amino acid sequence represented by SEQ ID NO: 2. SEQ ID NO: 1 shows the nucleotide sequence of the Chinese hamster fucose transporter gene.

A method for decreasing fucose existing in the Golgi apparatus is not specifically limited. That is, such fucose can be decreased by any method. An example of such method is a method by which the amount of fucose to be incorporated into the Golgi apparatus is decreased.

The Golgi apparatus incorporates fucose into itself mainly via fucose transporters existing on the Golgi membrane. Through inhibition of the fucose transporter functions, incorporation of fucose into the Golgi apparatus can be inhibited and the amount of fucose to be incorporated into the Golgi apparatus can be decreased.

To inhibit fucose transporter functions of cells means to cause a decrease or disappearance of the fucose transport activity of a fucose transporter.

The fucose transporter functions of cells may be inhibited by any method, that is, by a method known by persons skilled in the art. Specific examples of such method include a method by which the number of fucose transporters is decreased by inhibiting fucose transporter expression, or the like, and a method by which the fucose transport ability of a fucose transporter is lowered by the use of, for example, an antagonist for the fucose transporter.

A method for inhibiting fucose transporter expression is not specifically limited, as long as the number of fucose transporters having normal transport ability decreases. Fucose transporter expression can be inhibited by, for example, removal of a fucose transporter gene contained in a genome, inhibition of the process for transcription to mRNA, mRNA degradation, or inhibition of the process for translation into protein. Specific examples of a method for inhibiting the expression of a fucose transporter gene include a method that involves deleting (knockout) a gene that encodes a fucose transporter using a targeting vector or the like that targets the fucose transporter, a method that uses an antisense DNA for a gene encoding a fucose transporter, or a method that uses RNA interference (RNAi). Cells having inhibited fucose transporters may be cells having fucose transporter functions that have been inhibited by any method. For use in production of pharmaceutical products and the like, cells for which no Cre-loxp is used are preferable as cells having highly stable chromosomes (Schumidt E. E. et al., PNAS 97, 13702-13707 (February 2001)).

Protein produced by the production method of the present invention may be any protein. In general, such protein is a glycoprotein and preferably an antibody.

Types of antibody that are produced by the method of the present invention are not specifically limited. For example, mouse antibodies, rat antibodies, rabbit antibodies, sheep antibodies, camel antibodies, human antibodies, and artificially altered (for the purpose of, for example, lowering heterologous antigenicity against humans) gene recombinant antibody such as a chimeric antibody or a humanized antibody can be appropriately used. Such gene recombinant antibodies can be produced using a known method. A chimeric antibody comprises the variable region of the heavy and light chains of an antibody of a non-human mammal such as a mouse and the constant region of the heavy and light chains of a human antibody. DNA encoding the variable region of a mouse antibody is ligated to DNA encoding the constant region of a human antibody. The resultant is incorporated into an expression vector, and then the vector is introduced into a host to cause the host to produce the gene product. Thus a gene recombinant antibody can be obtained. A humanized antibody is also referred to as a reshaped human antibody. A humanized antibody is obtained by transplanting the complementarity determining region (CDR) of an antibody of a non-human mammal such as a mouse into the complementarity determining region of a human antibody. General gene recombination techniques therefor are also known. Specifically, DNA sequences designed to have the CDR of a mouse antibody ligated to the framework region (FR) of a human antibody are synthesized by the PCR method from several oligonucleotides, adjacent oligonucleotides of which have an overlap region at their terminal portions. The thus obtained DNA is ligated to DNA encoding the constant region of a human antibody, the resultant is incorporated into an expression vector, and then the vector is introduced into a host to cause the host to produce the gene product, so that a gene recombinant antibody can be obtained (see European Patent Application Publication No. EP 239400 and International Patent Application Publication No. WO 96/02576). As the FR of a human antibody, which is ligated via CDR, FR that allows the formation of an antigen-binding site with a good complementarity determining region is selected. If necessary, for the formation of an antigen-binding site having the appropriate complementarity determining region of a reshaped human antibody, the amino acids of the framework region of an antibody variable region may be substituted (Sato, K. et al., Cancer Res, 1993, 53, 851-856. ). Furthermore, methods for obtaining human antibodies are also known. For example, a desired human antibody having activity of binding to an antigen can also be obtained by sensitizing a human lymphocyte in vitro with a desired antigen or a cell that expresses a desired antigen and then fusing the sensitized lymphocyte to a human myeloma cell such as U266 (see JP Patent Publication (Kokoku) No. 1-59878 B (1989)). Moreover, a desired human antibody can be obtained by immunizing a transgenic animal that has all the repertories of a human antibody gene with a desired antigen (see International Patent Application Publication No. WO93/12227, WO92/03918, WO94/02602, WO94/2558, WO96/34096, and WO96/33735). Furthermore, a technique is also known by which a human antibody is obtained by panning using a human antibody library. For example, the variable region of a human antibody is expressed as a single chain antibody (scFv) on the surface of a phage by a phage display method. A phage that binds to an antigen can be selected. A DNA sequence encoding the variable region of a human antibody that binds to the antigen can be determined by analyzing the gene of the thus selected phage. When the DNA sequence of scFv that binds to an antigen is revealed, an appropriate expression vector is constructed based on the sequence, and then a human antibody can be obtained. These methods are already known. Concerning these methods, WO92/01047, WO92/20791, WO93/06213, WO93/11236, WO93/19172, WO95/01438, and WO95/15388 can be referred to.

Furthermore, the antibody of the present invention may be a lower molecular weight antibody such as an antibody fragment or a modified product of the antibody, as long as such antibody can bind to an antigen. Examples of such antibody fragment include Fab, F(ab')$_2$, Fv, or single chain Fv(scFv) wherein Fv of the H chain and Fv of the L chain are linked using an appropriate linker (Huston, J. S. et al., Proc. Natl. Acad. Sci. U.S.A. (1988) 85, 5879-5883), and a diabody. To obtain such antibody fragment, a gene encoding such antibody fragment is constructed, the gene is introduced into an expression vector, and then the gene is expressed in an appropriate host cell (e.g., see Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137). A diabody is prepared by dimerization; specifically, by linking two fragments (e.g., scFv), each of which is prepared by linking two variable regions using a linker or the like (hereinafter, referred to as a fragment composing a diabody). Generally, a diabody contains two VLs and 2 VHs (P. Holliger et al., Proc. Natl. Acad. Sci. U.S.A. 90, 6444-6448 (1993); EP404097; WO93/11161; Johnson et al., Methods in Enzymology, 203, 88-98, (1991); Holliger et al., Protein Engineering, 9, 299-305, (1996); Perisic et al., Structure, 2, 1217-1226, (1994); John et al., Protein Engineering, 12(7), 597-604, (1999); Holliger et al., Proc. Natl. Acad. Sci. U.S.A. 90, 6444-6448, (1993); and Atwell et al., Mol. Immunol. 33, 1301-1312, (1996)).

As a modified product of an antibody, antibodies to which various molecules such as polyethylene glycol (PEG) have been bound can also be used. Furthermore, a radioactive isotope, a chemical therapeutic agent, a cytotoxic substance such as toxin derived from bacteria, or the like can be bound to an antibody. In particular, a radiolabeled antibody is useful. Such modified product of an antibody can be obtained by chemically modifying an obtained antibody. In addition, methods for modifying antibodies have already been established in the field.

A recombinant polypeptide can be produced by a method known by persons skilled in the art. In general, such recombinant polypeptide can be purified and prepared as follows. DNA encoding a polypeptide is incorporated into an appropriate expression vector, a transformant that has been obtained by introducing the vector into an appropriate host cell is collected, and then an extract is obtained. Subsequently, the resultant is subjected to chromatography such as ion exchange chromatography, reverse phase chromatography, or gel filtration, affinity chromatography using a column (to which an antibody against the polypeptide of the present invention has been immobilized), or chromatography using combination of a plurality of such columns.

Furthermore, when protein is expressed as a fusion polypeptide with a glutathione-S-transferase protein or as a recombinant polypeptide to which a plurality of histidines have been added in host cells (e.g., animal cells or *Escherichia coli*), the expressed recombinant polypeptide can be purified using a glutathione column or a nickel column. After purification of the fusion polypeptide, if necessary, regions other than the target polypeptide can also be cleaved and removed from the fusion polypeptide using thrombin or factor Xa.

Protein to be produced by the production method of the present invention is preferably an antibody with cytotoxic activity that is affected by fucose binding thereto.

A method for producing an antibody using genetic recombination techniques, which is well known by persons skilled in the art, involves incorporating an antibody gene into an appropriate vector, introducing the vector into a host, and thus causing the production of the antibody using genetic recombination techniques (e.g., see Carl, A. K. Borrebaeck, James, W. Larrick, THERAPEUTIC MONOCLONAL ANTIBODIES, Published in the United Kingdom by MACMILLAN PUBLISHERS LTD, 1990).

Furthermore, the present invention encompasses a host cell that can produce a foreign protein, wherein no fucose is added to the foreign protein.

Such cells are characterized in that fucose existing in the cells, such as in the Golgi apparatus, is decreased. A method for decreasing fucose existing in the Golgi apparatus is not specifically limited. That is, such fucose can be decreased by any method. An example of such method is a method by which the amount of fucose to be incorporated into the Golgi apparatus is decreased. The Golgi apparatus incorporates fucose into itself mainly via fucose transporters existing on the Golgi membrane. Through inhibition of the fucose transporter functions, incorporation of fucose into the Golgi apparatus can be inhibited and the amount of fucose to be incorporated into the Golgi apparatus can be decreased.

To inhibit fucose transporter functions of cells means to cause a decrease or disappearance of the fucose transport activity of a fucose transporter.

The fucose transporter functions of cells may be inhibited by any method, that is, by a method known by persons skilled in the art. Specific examples of such method include a method by which the number of fucose transporters is decreased by inhibiting fucose transporter expression, or the like, and a method by which the fucose transport ability of a fucose transporter is lowered by the use of, for example, an antagonist for the fucose transporter.

A method for inhibiting fucose transporter expression is not specifically limited, as long as the number of fucose transporters having normal transport ability decreases. Fucose transporter expression can be inhibited by, for example, removal of a fucose transporter gene contained in a genome, inhibition of the process for transcription to mRNA, mRNA degradation, or inhibition of the process for translation into protein. Specific examples of a method for inhibiting the expression of a fucose transporter gene include a method that involves deleting (knockout) a gene that encodes a fucose transporter using a targeting vector or the like that targets the fucose transporter, a method that uses an antisense DNA for a gene encoding a fucose transporter, or a method that uses RNA interference (RNAi). These methods will be described later.

Protein having no fucose binding thereto can be obtained by expressing a foreign protein using such cells having inhibited fucose transporter functions as host cells. Here, a foreign protein means a protein not derived from the cell itself. Host cells are not specifically limited. For example, cells wherein sugar is added to a recombinant protein when the protein is expressed can be used. More specifically, various animal cells or the like can be used. Preferably CHO cells can be used. In the present invention, in particular, CHO cells wherein a fucose transporter gene has been knocked out can be appropriately used. As animal cells, mammalian cells such as CHO (J. Exp. Med. (1995) 108, 945), COS, 3T3, myeloma, BHK (baby hamster kidney), HeLa, and Vero are known. As amphibian cells, Xenopus oocytes (Valle, et al., Nature (1981) 291, 358-340), for example, are known. As insect cells Sf9, Sf21, and Tn5, for example, are known. Examples of CHO cells include dhfr-CHO cells (Proc. Natl. Acad. Sci. U.S.A. (1980) 77, 4216-4220) and CHO K-1 cells (Proc. Natl. Acad. Sci. U.S.A. (1968) 60, 1275), which are deficient in a DHFR gene. For the purpose of mass-expression in animal cells, CHO cells are particularly preferable.

Protein having no fucose binding thereto can be obtained by incorporating a gene encoding a foreign protein such as an antibody to be produced into an expression vector and then incorporating the expression vector into host cells capable of producing such foreign protein; that is, cells having inhibited fucose transporter functions. Examples of vectors include expression vectors derived from mammals (e.g., pcDNA3 (produced by Invitrogen Corporation) and pEGF-BOS (Nucleic Acids. Res.1990, 18(17), p. 5322), pEF, and pCDM8), expression vectors derived from insect cells (e.g., the "Bac-to-BAC baculovirus expression system" (produced by GIBCO-BRL Life Technologies Inc.) and pBacPAK8), expression vectors derived from plants (e.g., pMH1 and pMH2), expression vectors derived from animal viruses (e.g., pHSV, pMV, and pAdexLcw), expression vectors derived from retroviruses (e.g., pZIPneo), expression vectors derived from yeast (e.g., the "Pichia Expression Kit" (produced by Invitrogen Corporation), pNV11, and SP-Q01), and expression vectors derived from *Bacillus subtilis* (e.g., pPL608 and pKTH50). When CHO cells are used as host cells, it is preferable to use a vector derived from a mammal.

For the purpose of expression in animal cells such as CHO cells, COS cells, or NIH3T3 cells, generally a vector used herein has a promoter required for expression within cells, such as an SV40 promoter (Mulligan et al., Nature (1979) 277, 108), an MMLV-LTR promoter, an EF1α promoter (Mizushima et al., Nucleic Acids Res. (1990) 18, 5322), or a CMV promoter. It is further preferable that such vector hase a gene for selection of transformed cells (e.g., a drug resistance gene that enables distinguishment by the use of a drug (e.g., neomycin and G418)). Examples of a vector having such properties include pMAM, pDR2, pBK-RSV, pBK-CMV, pOPRSV, and pOP13.

Furthermore, an example of a method for the purpose of stable expression of a gene and amplification of the number of copies of a gene within cells involves introducing a vector (e.g., pCHOI) having a complementary DHFR gene into CHO cells that are deficient in the nucleic acid synthesis pathway, followed by amplification using methotrexate (MTX). Furthermore, an example of a method for the purpose of transient expression of a gene involves transforming COS cells having a gene that expresses SV40 T antigen on the chromosome with a vector (e.g., pcD) having an SV40 replication origin. As a replication initiation site, a site derived from polyoma virus, adenovirus, bovine papilloma virus (BPV), or the like can also be used. Furthermore, to amplify the number of copies of a gene in a host cell system, an expression vector may contain as a selection marker an aminoglycoside transferase (APH) gene, thymidine kinase (TK) gene, *Escherichia coli* xanthine-guanine phosphoribosyltransferase (Ecogpt) gene, dihydrofolate reductase (dhfr) gene, or the like.

A vector can be introduced into a host cell by, for example, a calcium phosphate method, a DEAE dextran method, a method using cationic ribosome DOTAP (produced by Boehringer Mannheim), an electroporation method, or lipofection.

Cell culture can be carried out according to a known method. As a culture solution for animal cells, DMEM, MEM, RPMI1640, or IMDM, for example, can be used. At this time, a serum fluid such as fetal calf serum (FCS) can be used together therewith. Alternatively serum-free culture may also be carried out. pH during culture is preferably between approximately 6 and 8. Culture is generally carried out at approximately 30° C. to 40° C. for approximately 15 to 200 hours. If necessary, exchange of media, aeration, and agitation are carried out.

Protein produced by the host cells of the present invention may be any protein. In general, such protein is a glycoprotein and preferably an antibody.

Types of antibody that are produced by the method of the present invention are not specifically limited. For example, mouse antibodies, rat antibodies, rabbit antibodies, sheep antibodies, camel antibodies, human antibodies, and artificially altered (for the purpose of, for example, lowering heterologous antigenicity against humans) gene recombinant antibody such as a chimeric antibody or a humanized antibody can be appropriately used. Such gene recombinant antibodies can be produced using a known method. Information about antibodies has already been described above.

An example of a cell wherein fucose transporter expression is inhibited is a cell wherein a gene encoding a fucose transporter is disrupted. "Disruption of a gene" means the suppression of the expression of the gene by partial deletion, substitution, insertion, addition, or the like conducted for the nucleotide sequence of the gene. "Disruption of a gene" of the present invention includes not only a case where gene expression is completely suppressed, but also a case wherein gene expression is partially suppressed. "Deletion (knockout) of a gene" and "inactivation of a gene" are also used so as to have a meaning equivalent to that of "disruption of a gene." Furthermore, cells having a gene disrupted by homologous recombination using gene targeting are referred to as gene-knock out cells. A cell wherein a gene encoding a fucose transporter is disrupted is an example of a cell wherein fucose transporter expression is artificially suppressed. A cell wherein a gene encoding a fucose transporter is disrupted is a cell wherein the amount of fucose existing in the Golgi apparatus is significantly decreased compared with that in a cell wherein a fucose transporter gene is not disrupted, a cell wherein intracellular fucose transport ability is lowered or deleted, or a cell wherein intracellular activity to incorporate fucose into the Golgi apparatus is lowered or eliminated. The amount of fucose in the Golgi apparatus can be measured by isolating the Golgi apparatus from a cell, extracting sugar, and then carrying out an antigen antibody reaction, a binding reaction between sugar and lectin, liquid chromatography, electrophoresis, or the like. Moreover, intracellular fucose transport ability and intracellular activity to incorporate fucose into the Golgi apparatus can be measured by, for example, using fucose labeled with a fluorescent substance, a radioisotope, or the like.

A gene can be disrupted by, for example, a homologous recombination method.

Such homologous recombination method means a method by which only the target gene is arbitrarily altered by homologous gene recombination between a gene on a chromosome and a foreign DNA. Another DNA sequence is inserted into an exon of a gene for the purpose of dividing a sequence encoding a protein. To facilitate identification of a cell having a gene targeting vector, a selection marker such as a neomycin resistance gene derived from a bacterium is generally used as a sequence to divide the gene. A targeting vector is designed and produced based on the sequence information of the fucose transporter gene described in this specification and the fucose transporter gene to be disrupted is then subjected to homologous recombination using the targeting vector. For example, a substitution vector can contain a homologous region that has been ligated to the 5' and the 3' side of mutation to be introduced, a positive selection marker, a restriction enzyme site for linearizing the vector outside the homologous region, a negative selection marker arranged outside the homologous region, a restriction enzyme cleavage site for detecting mutation, and the like. Targeting vectors can be produced according to methods described in, for example, edited by Kenichi Yamamura et al., Transgenic Animal, KYORITSU SHUPPAN CO., LTD., Mar. 1, 1997; Shinichi Aizawa, Gene Targeting, Production of Mutant Mice using ES cells, Bio Manual Series 8, YODOSHA CO., LTD., 1995; Hogan et al., Manipulating the Mouse Embryo, Cold Spring Harbor Laboratory Press (1944); Joyner, A. L., Gene Targeting, A Practical Approach Series, IRL Press (1993); and edited by Masami Matsumura et al., Experimental Medicine, Separate Volume, New Genetic Engineering Handbook (3rd revised version), YODOSHA CO., LTD., 1999. Both insertion and substitution targeting vectors may be used. Furthermore, recombination can also be caused by targeting using a Cre-lox system. Targeting using the Cre-lox system can be carried out according to a method described in, for example, JP Patent Publication (Kohyo) NO. 11-503015 A (1999). As a method for selecting homologous recombinants that have experienced homologous recombination, a known selection method such as positive selection, promoter selection, negative selection, or polyA selection may be used. For identification of a homologous recombinant, both the PCR method and the Southern blotting method can be used.

In addition, examples of a method for producing a cell wherein fucose transporter expression is inhibited include an antisense method, a ribozyme method, a method using a retrovirus, a method using a transposon, an RNAi method, an RDO method, a TFO method, and a method for obtaining established cells from mammals wherein a fucose transporter gene has been knocked out.

The antisense method is a method for inhibiting fucose transporter translation in cells using an antisense oligonucleotide of the fucose transporter gene of the present invention. An example of an antisense oligonucleotide is an antisense oligonucleotide that hybridizes to any position in the nucleotide sequence of SEQ ID NO: 1 or a complementary sequence thereof. For example, such antisense oligonucleotide generally corresponds to at least 15 sequential nucleotides in the nucleotide sequence of SEQ ID NO: 1. Further preferably, such antisense oligonucleotide is characterized in that at least 15 sequential nucleotides contain a translation initiation codon. Examples of such antisense oligonucleotides include not only antisense oligonucleotides (wherein all the nucleotides corresponding to the nucleotides that compose a predetermined region of DNA or mRNA form a complementary sequence), but also include, as long as DNA or mRNA and oligonucleotides can specifically hybridize to the nucleotide sequence represented by SEQ ID NO: 1, oligonucleotides wherein a mismatch of 1 or a plurality of nucleotides is present. Specific conditions for hybridization are, for example, low stringent conditions. Such low stringent conditions comprise, upon washing after hybridization, for example, 42° C., 0.1×SSC, and 0.1% SDS, and preferably 50° C., 0.1×SSC, and 0.1% SDS. More preferable hybridization conditions are, for example, high stringent conditions. Such high stringent conditions comprise, for example, 65° C., 5×SSC, and 0.1% SDS. However, a plurality of factors such as temperature and salt concentration may influence the stringency concerning hybridization. Persons skilled in the art can realize stringency similar to the above stringency by appropriately selecting these factors.

As antisense oligonucleotides, derivatives or modified products thereof can be used. Examples of such modified products include methylphosphonate-type or ethylphosphonate-type products such as modified lower alkyl phosphonate, modified phosphorothioate, and modified phosphoroamidate.

Such antisense oligonucleotide acts on cells that produce the polypeptide of the present invention and binds to DNA or mRNA encoding the polypeptide, thereby inhibiting transcription or translation and promoting mRNA degradation. As a result of suppression of the expression of the polypeptide of the present invention, the antisense oligonucleotide has an effect of suppressing the action of the polypeptide of the present invention.

An antisense oligonucleotide is inserted downstream of a promoter of an appropriate expression vector, and then host cells can also be transformed with the expression vector.

A ribozyme method involves cleaving mRNA of a fucose transporter gene in cells using RNA having activity to cleave nucleic acids, so as to avoid the expression of the gene. A ribozyme comprises a recognition site complementary to a substrate RNA, a loop-shaped enzyme active site, and a stem II region accompanying the enzyme active site. Such recognition site may be designed so as to become complementary to a part of the fucose transporter gene of the present invention. In a manner similar to that in the above antisense method, a ribozyme is inserted downstream of a promoter of an appropriate expression vector that enables expression of the ribozyme. Host cells are then transformed with the expression vector. The ribozyme method can be carried out according to the descriptions in Cell Technology, 12, 239 (1993); BIO/TECHNOLOGY, 17, 1097 (1999); Hum. Mol. Genet., 5, 1083 (1995); Cell Technology, 13, 255 (1994); and Proc. Natl. Acad. Sci, U.S.A. 96, 1886 (1999). Screening for cells that have become unable to produce any fucose transporter because of the antisense method or the ribozyme method may be carried out using fucose transporter activity as an index. Alternatively, such screening can also be carried out by Western blotting or Northern blotting using fucose transporter gene transcription or expression as an index.

Furthermore, a fucose transporter gene can be disrupted using a retrovirus. A retrovirus is introduced into host cells by infecting the host cells with the retrovirus. Then, cells having disrupted fucose transporter genes are screened for. Thus, cells not having fucose transporter activity can be obtained. Cells may be screened for using fucose transporter activity as an index. Alternatively, cells may also be screened for by Western blotting or Northern blotting using fucose transporter gene transcription or expression as an index.

Furthermore, a fucose transporter gene is disrupted in a similar manner using a transposon. Then, cells having disrupted fucose transporter genes are obtained by screening. The thus obtained cells may also be used for antibody production. A transposon system may be constructed according to a method described in NatureGent, 25, 35, (2000) or the like.

Furthermore, cells wherein the expression of the fucose transporter of the present invention is inhibited can also be obtained using RNA interference (RNAi). RNAi is a phenomenon whereby when double-strand RNA (dsRNA) is introduced into a cell, intracellular mRNA corresponding to the RNA sequence is specifically degraded so that the gene is not expressed as protein. In the case of RNAi, double-strand RNA is generally used, but RNAi is not limited thereto. For example, double strands that are formed in self-complementary single-strand RNAs can also be used. Regarding regions where double strands are formed, double strands may be formed in all the regions or single strands or the like may be formed in partial regions (e.g., both ends or one end). The length of oligo RNA to be used for RNAi is not limited. The length of the oligo RNA of the present invention is, for example, 5 to 1000 nucleotides (in the case of double strands, 5 to 1000 bp), preferably 10 to 100 nucleotides (in the case of double strands, 10 to 100 bp), further preferably 15 to 25 nucleotides (in the case of double strands, 15 to 25 bp), and particularly preferably 19 to 23 nucleotides (in the case of double strands, 19 to 23 bp).

As described above, the RNAi method makes use of a phenomenon whereby a double-strand RNA (dsRNA) being homologous to a gene and consisting of sense RNA and antisense RNA disrupts a homologous portion of a gene transcription product (mRNA). A double-strand RNA corresponding to the full-length sequence of a fucose transporter gene to be used herein may be used or a short (e.g., 21 to 23 b) dsRNA (small interfering RNA; siRNA) corresponding to a partial sequence may also be used. A double-strand RNA may be directly incorporated into a cell. Alternatively, a vector producing a double-strand RNA is constructed, the vector is introduced into a host cell, and then the double-strand RNA may be produced within the cell. For example, the whole or a portion of the DNA encoding the fucose transporter of the present invention is incorporated into a vector such that it becomes an inverted repeat sequence, and then the vector may be introduced into a host cell. The RNAi method can be conducted according to the descriptions in Nature, 391, 806, (1998); Proc. Natl. Acsd. Sci. U.S.A. 95, 15502 (1998); Nature, 395, 854, (1998); Proc. Natl. Acsd. Sci. U.S.A. 96, 5049, (1999); Cell, 95, 1017, (1998); Proc. Natl. Acsd. Sci. U.S.A. 96, 1451, (1999); Proc. Natl. Acsd. Sci. U.S.A. 95, 13959, (1998); Nature Cell Biol., 2, 70, (2000); and the like. Screening for cells that have become unable to produce any fucose transporter as a result of the use of the RNAi method may be carried out using fucose transporter activity as an index. Alternatively, such screening can also be carried out by Western blotting or Northern blotting using fucose transporter gene transcription or expression as an index.

The fucose transporter of the present invention can also be disrupted by an RDO method or a TFO method. RDO (chimeric RNA-DNA oligonucleotide) is a double strand formed by binding a DNA strand to an RNA strand, and is characterized by having a GC clamp and a T loop. Through the use of RDO corresponding to a fucose transporter gene, mutation can be introduced into the fucose transporter gene and the gene can be disrupted. RDO can be constructed according to the descriptions in Science, 273, 1386, (1996); Nature Medicine, 4, 285, (1998); Hepatology, 25, 1462, (1997); Gene Therapy, 5, 1960, (1999); J. Mol. Med., 75, 829, (1997); Proc. Natl. Acsd. Sci. U.S.A. 96, 8774, (1999); Proc. Natl. Acsd. Sci. U.S.A. 96, 8768, (1999); Nuc. Acids. Res., 27, 1323, (1999); Invest, Dematol., 111, 1172, (1998); Nature Biotech., 16, 1343, (1998), Nature Biotech., 18, 43, (2000); Nature Biotech., 18, 555, (2000); J. Mol. Med., 80, 620, (2002); and the like. A triplex-forming oligonucleotide (TFO) is a short single-strand DNA segment that can bind to a specific site of double-strand genomic DNA and can induce mutation at its binding site. TFO can be constructed according to the descriptions in J. Mol. Med., 80, 620, (2002) and the like.

Furthermore, a cell wherein the fucose transporter gene of the present invention is disrupted can also be obtained by randomly introducing mutation into a cell. Examples of a method for randomly introducing mutation into a cell include a method that involves randomly introducing a gene disruption vector containing a marker into the genome of a cell and then screening for a cell having a disrupted fucose transporter gene, and a method that involves randomly introducing mutation using an chemical mutagen such as ENU (N-ethyl-N-nitrosourea) and then screening for such cell having a disrupted fucose transporter gene. Screening for cells that have become unable to produce any fucose transporter may be carried out using fucose transporter activity as an index. Alternatively, such screening can also be carried out by Western blotting or Northern blotting using fucose transporter gene transcription or expression as an index.

Furthermore, the cell of the present invention having a disrupted fucose transporter gene can also be obtained from an animal having a knocked-out fucose transporter gene. Such animal having a knocked-out fucose transporter gene can be produced by disrupting a fucose transporter of an ES cell by the above method and then producing from the ES cell according to, for example, a method disclosed in WO02/33054 Publication. Examples of animals that are used in this case include, but are not limited to, goats, pigs, sheep, cattle, mice, hamsters, and rats. Established cells having no fucose transporter genes can be obtained by producing such established cells from animals having a knocked-out fucose transporter gene.

Cells wherein fucose transport ability is lowered or disappears can be obtained by various methods. For example, such cells can be obtained by inhibiting fucose transporter functions using a compound (specifically, an antagonist for the fucose transporter) that binds to the fucose transporter and then inhibits fucose transport from the cytoplasm into the Golgi apparatus. The present invention also encompasses a method for inhibiting cellular fucose transporter functions using such compound and cells wherein fucose transporter functions are inhibited by such compound. Cells wherein fucose transporter functions are inhibited are cells wherein the amount of fucose existing in the Golgi apparatus is significantly decreased compared with cells wherein fucose transporter functions are not inhibited. Furthermore, cells wherein fucose transporter functions are inhibited are cells wherein fucose transport ability is lowered or eliminated in the Golgi membrane. Such cells also mean cells wherein intracellular activity to incorporate fucose into the Golgi apparatus is lowered or eliminated. Examples of such compound that inhibits fucose transporter functions include a compound that is isolated by the above screening method and an antibody that binds to fucose transporter activity. Such compound may be added to a medium for host cells that are caused to produce a recombinant protein. Moreover, when such compound is protein, DNA encoding the protein is introduced into an appropriate expression vector, host cells are transformed with the expression vector, and then the protein can be expressed and produced in host cells.

When foreign recombinant protein is produced in host cells having disrupted fucose transporter genes or the fucose transport activity of the fucose transporter of the present invention is inhibited, intracellular fucose is not transported into the Golgi apparatus. Thus, fucose is not added to protein. In the case of such recombinant protein produced in host cells having disrupted fucose transporter genes, the amount of bound fucose is significantly lower or preferably unable to be detected, compared with the case of recombinant protein produced in host cells having an undisrupted fucose transporter gene. When a foreign protein is an antibody, a product can be obtained wherein no fucose is binding to an N-glycoside-bound sugar chain binding to 2 sugar-chain-binding sites existing in 1 molecule of an antibody; that is, existing in the Fc region composed of 2 H chains. Such antibody having no fucose binding thereto has enhanced cytotoxic activity. Incorporation of an antibody gene in a cell can be carried out by a general genetic engineering technique. In addition, when an antibody for which the addition of fucose thereto is inhibited is produced using the cell of the present invention, it is not necessary that all the produced antibodies experience the addition of fucose thereto. The proportion of protein to which fucose has been added in antibody compositions should be reduced.

Furthermore, the present invention also encompasses animals (excluding humans) wherein fucose transporter gene expression is inhibited. A recombinant polypeptide can be produced in vivo using such animals. An example of such animal wherein fucose transporter gene expression is inhibited is the above fucose transporter-knockout animal. Production of knockout animals wherein a specific gene is knocked-out as described above is already a well-known technique. Persons skilled in the art can appropriately produce such fucose transporter gene-knockout animals. Moreover, animals wherein fucose transporter gene expression is inhibited can be produced by, for example, introducing a gene expressing an antisense oligonucleotide for a fucose transporter.

DNA encoding target protein is introduced into these animals, polypeptides are produced in vivo within the animals, and then the polypeptides are collected. The term "host" in the present invention encompasses these animals and the like. When animals are used, there are production systems using mammals and production systems using insects. As mammals, goats, pigs, sheep, mice, or cattle can be used (Vicki Glaser, SPECTRUM Biotechnology Applications, 1993).

For example, a target DNA is prepared in the form of a fusion gene with a gene encoding a polypeptide such as goat β casein that is uniquely produced in milk. Subsequently, a DNA fragment comprising the fusion gene is injected into a goat embryo and then the embryo is transplanted into a female goat. A target polypeptide can be obtained from milk that is produced by transgenic goats born from goats that have accepted such embryos or from the progenies of such transgenic goats. To increase the amount of milk containing polypeptides, which is produced by transgenic goats, an appropriate hormone may also be used for such transgenic goats (Ebert, K. M. et al., Bio/Technology (1994) 12, 699-702).

The thus obtained polypeptide can be isolated from within host cells or outside the cells (e.g., media) and then purified as a substantially pure and uniform polypeptide. To separate and purify polypeptides, separation and purification methods that are generally used for polypeptide purification may be employed and are not specifically limited. For example, polypeptides can be separated and purified by the use of appropriate selection and combination of a chromatography column, a filter, ultrafiltration, salting-out, solvent precipitation, solvent extraction, distillation, immunoprecipitation, SDS-polyacrylamide gel electrophoresis, an isoelectric focusing method, dialysis, recrystallization, and the like.

Examples of chromatography include affinity chromatography, ion exchange chromatography, hydrophobic chromatography, gel filtration, reverse phase chromatography, and adsorption chromatography (Strategies for Protein Purification and Characterization: A Laboratory Course Manual, Ed Daniel R. Marshak et al., Cold Spring Harbor Laboratory Press, 1996). These types of chromatography can be carried out using liquid-phase chromatography such as HPLC or FPLC.

In addition, when a proper protein modification enzyme is caused to act on polypeptides before or after purification, modification can be arbitrarily carried out or peptides can be partially removed. As protein modification enzymes, trypsin, chymotrypsin, lysylendopeptidase, protein kinase, and glucosidase, for example, are used.

A known sequence can also be used for a gene encoding the H chain or the L chain of an antibody that is produced by the production method of the present invention. Furthermore, such gene can also be obtained by a method known by persons skilled in the art. For example, a gene encoding an antibody can be cloned and obtained from a hybridoma producing a monoclonal antibody or can also be obtained from an antibody library. Hybridomas can be produced basically using a known technique as described below. Specifically, a hybridoma can be produced by using as a sensitizing antigen a desired antigen or a cell that expresses a desired antigen, carrying out immunization according to a general immunization method using such antigen, fusing the thus obtained immunocyte with a known parent cell by a general cell fusion method, and then screening for a monoclonal antibody-producing cell (hybridoma) by a general screening method. The cDNA of an antibody variable region (V region) is synthesized from the mRNA of the thus obtained hybridoma using reverse transcriptase. The cDNA is ligated to DNA encoding a desired antibody constant region (C region), so that a gene encoding the H chain or the L chain can be obtained. A sensitizing antigen upon immunization is not specifically limited. For example, the full-length protein of a target receptor, a partial peptide (e.g., extracellular region), and the like can be used. Antigens can be prepared by a method known by persons skilled in the art. For example, antigens can be prepared according to a method using baculovirus (e.g., WO98/46777). Hybridomas can be produced according to, for example, Milstein et al's method (Kohler, G., and Milstein, C., Methods Enzymol. 1981, 73, 3-46) or the like. When the immunogenicity of an antigen is low, such antigen is bound to a macromolecule having immunogenicity, such as albumin, and then immunization is carried out.

Regarding an antibody library, many antibody libraries are already known. In addition, a production method for an antibody library is known. Hence, persons skilled in the art can appropriately obtain an antibody library.

Antibodies that are expressed and produced as described above can be purified by a known method that is used for general protein purification. Antibodies can be separated and purified by appropriate selection or combination of, for example, an affinity column (e.g., protein A column), a chromatography column, a filter, ultrafiltration, salting-out, and dialysis (Antibodies: A Laboratory Manual, Ed Harlow and David Lane, Cold Spring Harbor Laboratory, 1988).

A known means can be used for measuring the antigen-binding activity (Antibodies A Laboratory Manual, Ed Harlow, David Lane, Cold Spring Harbor Laboratory, 1988). For example, ELISA (enzyme-linked immunosorbent assay), EIA (enzyme-linked immunoassay), RIA (radioimmunoassay), or a fluorescent immunoassay can be used.

The sugar chain structure of protein produced using the cell of the present invention can be analyzed by a method described in a 2-dimensional sugar chain mapping method (Anal. Biochem, 171, 73 (1988); Biochemical Experimental Methods 23-Methods for Studying Glycoprotein Sugar Chains, edited by Reiko Takahashi, Center for Academic Publications Japan (1989)). Moreover, sugar chains can also be analyzed by mass spectrometry such as MALDI-TOF-MS.

A compound that binds to a fucose transporter and then inhibits fucose transport from the cytoplasm into the Golgi apparatus can be screened for by the following method. Specifically, a fucose transporter is contacted with a sample to be tested that presumably contains a compound binding to the fucose transporter, and then the binding activity between the polypeptide and the sample to be tested is detected, so that a compound having activity of binding to the fucose transporter can be selected.

Furthermore, a fucose transporter is contacted with a sample to be tested and then the fucose transport activity of the fucose transporter is detected, so that a compound that inhibits the fucose transport activity of the fucose transporter can be selected.

The polypeptide of the present invention that is used for screening may be a recombinant polypeptide, a polypeptide derived from nature, or a partial peptide. Furthermore, the polypeptide of the present invention to be used for screening may be in a form whereby it is expressed on the cell surface or the form of a membrane fraction. Examples of a sample to be tested are not specifically limited and include cell extracts, cell culture supernatants, products of fermentation microorganisms, extracts of marine organisms, plant extracts, purified or crudely purified polypeptides, non-peptide compounds, synthetic low molecular weight compounds, and natural compounds. The polypeptide of the present invention (that is contacted with such sample to be tested) can be contacted in the form of, for example, a purified polypeptide, a soluble polypeptide, a polypeptide bound to a carrier, a polypeptide that is fused with another polypeptide, a polypeptide expressed on the cell membrane, or a membrane fraction, with a sample to be tested.

As a method for screening for a polypeptide that binds to the polypeptide of the present invention, many methods known by persons skilled in the art can be used. Such screening can be carried out by an immunoprecipitation method, for example. Specifically, such screening can be carried out as follows. A gene encoding the polypeptide of the present invention is inserted into a vector for expressing a foreign gene, such as pSV2neo, pcDNA I, or pCD8, so that the gene is expressed in animal cells or the like. As promoters to be used for expression, any promoters that can be generally used can be used. Examples of such promoter include an SV40 early promoter (Rigby In Williamson (ed.), Genetic Engineering, Vol. 3. Academic Press, London, p. 83-141 (1982)), an EF-1α promoter (Kim et al., Gene 91, pp. 217-223 (1990)), a CAG promoter (Niwa et al. Gene 108, pp. 193-200 (1991)), an RSV LTR promoter (Cullen Methods in Enzymology 152, pp. 684-704 (1987)), an SRα promoter (Takebe et al. Mol. Cell. Biol. 8, p. 466 (1988)), a CMV immediate early promoter (Seed and Aruffo Proc. Natl. Acad. Sci. U.S.A. 84, pp. 3365-3369 (1987)), an SV40 late promoter (Gheysen and Fiers, J. Mol. Appl. Genet. 1, pp. 385-394 (1982)), an Adenovirus late promoter (Kaufman et al. Mol. Cell. Biol. 9, p. 946 (1989)), and an HSV TK promoter.

Examples of a method for expressing a foreign gene by introducing the gene into animal cells include an electroporation method (Chu, G. et al., Nucl. Acid Res. 15, 1311-1326 (1987)), a calcium phosphate method (Chen, C and Okayama, H., Mol. Cell. Biol. 7, 2745-2752 (1987)), a DEAE dextran method (Lopata, M. A. et al. Nucl. Acids Res. 12, 5707-5717 (1984); Sussman, D. J. and Milman, G., Mol. Cell. Biol. 4, 1642-1643 (1985)), and a lipofectin method (Derijard, B., Cell 7, 1025-1037 (1994); Lamb, B. T. et al., Nature Genetics 5, 22-30 (1993); Rabindran, S. K. et al., Science 259, 230-234 (1993)). Any of these methods may be employed.

The polypeptide of the present invention can be expressed as a fusion polypeptide by introducing a recognition site (epitope) of a monoclonal antibody, the specificity of which has been clarified, into the N- or C-terminus of the polypeptide of the present invention. As an epitope-antibody system to be used herein, a commercial system can be used (Experimental Medicine 13, 85-90 (1995)). A vector that enables expression of a fusion polypeptide with β-galactosidase, a maltose-binding protein, glutathione-S-transferase, a green fluorescent protein (GFP), or the like via a multi-cloning site is marketed.

To keep the properties of the polypeptide of the present invention unchanged as far as possible when it is prepared in the form of a fusion polypeptide, a method has been reported wherein only a small epitope portion consisting of several to more than a dozen amino acids is introduced, so as to prepare a fusion polypeptide. For example, epitopes such as polyhistidine (His-tag), influenza hemagglutinin HA, human c-myc, FLAG, a vesicular stomatitis virus glycoprotein (VSV-GP), a T7 gene 10 protein (T7-tag), a human herpes simplex virus glycoprotein (HSV-tag), and an E-tag (an epitope on a monoclonal phage) and monoclonal antibodies that recognize such epitopes can be used as epitope-antibody systems for screening for polypeptides that bind to the polypeptide of the present invention (Experimental Medicine 13, 85-90 (1995)).

In immunoprecipitation, such antibody is added to a cell lysis solution prepared using an appropriate surfactant, so as to form an immune complex. The immune complex comprises the polypeptide of the present invention, a polypeptide capable of binding thereto, and an antibody. In addition to the use of an antibody against the above epitope, immunoprecipitation can also be carried out using an antibody against the polypeptide of the present invention. Such antibody against the polypeptide of the present invention can be prepared by, for example, introducing a gene encoding the polypeptide of the present invention into an appropriate *Escherichia coli* expression vector for expression within *Escherichia coli*, purifying the thus expressed polypeptide, and then immunizing rabbits, mice, rats, goats, chickens, or the like with the polypeptide. Moreover, such antibodies can also be prepared by immunizing a partial peptide of the synthesized polypeptide of the present invention with the above animals.

Immune complexes can be precipitated using Protein A Sepharose or Protein G Sepharose, for example, if antibodies are mouse IgG antibodies. Furthermore, when the polypeptide of the present invention is prepared as, for example, a fusion polypeptide with an epitope such as GST, an immune complex can also be formed using a substance such as glutathione Sepharose 4B that specifically binds to such epitope in a manner similar to that in a case where an antibody of the polypeptide of the present invention is used.

General methods for immunoprecipitation can be carried out by or according to, for example, a method described in literature (Harlow, E. and Lane, D.: Antibodies, pp. 511-552, Cold Spring Harbor Laboratory Publications, New York (1988)).

SDS-PAGE is generally employed for the analysis of immunoprecipitated polypeptides. Through the use of gel with an appropriate concentration, a bound polypeptide can be analyzed based on the molecular weight of the polypeptide. At this time, it is generally difficult to detect such polypeptide that has bound to the polypeptide of the present invention by a general staining method for polypeptides, such as Coomassie staining or silver staining. Detection sensitivity can be improved by culturing cells in a culture solution containing $^{35}$S-methionine or $^{35}$S-cysteine, which is a radioactive isotope, so as to label polypeptides within the cells and then detecting them. If the molecular amount of a polypeptide is revealed, such target polypeptide can be directly purified from SDS-polyacrylamide gel and then the sequence thereof can also be determined.

Furthermore, as a method for isolating a polypeptide that binds to the polypeptide of the present invention, an West western blotting method (Skolnik, E. Y. et al., Cell (1991) 65, 83-90), for example, can be employed. Specifically, a cDNA library is constructed from cells, tissues, or organs (e.g., testis) that are predicted to express a polypeptide that binds to the polypeptide of the present invention using a phage vector (e.g., λgt11 and ZAP). The resultant is then expressed on LB-agarose and then the expressed polypeptide is immobilized on a filter. The purified and labeled polypeptide of the present invention is caused to react with the above filter. Subsequently, plaques expressing polypeptides binding to the polypeptide of the present invention are detected based on the labels. Examples of a method for labeling the polypeptide of the present invention include a method using binding between biotin and avidin, a method using an antibody that specifically binds to the polypeptide of the present invention or a polypeptide (e.g., GST) fusing with the polypeptide of the present invention, a method using a radioisotope, and a method using fluorescence.

Another embodiment of the screening method of the present invention is a method that is conducted using a 2-hybrid system using cells (Fields, S., and Sternglanz, R., Trends. Genet. (1994) 10, 286-292; Dalton S, and Treisman R (1992), Characterization of SAP-1, a protein recruited by serum response factor to the c-fos serum response element., Cell 68, 597-612; "MATCHMARKER Two-Hybrid System," "Mammalian MATCHMAKER Two-Hybrid Assay Kit," "MATCHMAKER One-Hybrid System" (these systems and kits are all produced by Clontech), and "HybriZAP Two-Hybrid Vector System" (produced by Stratagene Corp.)).

In the 2-hybrid system, the polypeptide of the present invention or a partial peptide thereof is fused with an SRF DNA-binding region or a GAL4 DNA-binding region and then the product is expressed in yeast cells. A cDNA library that is expressed while being fused with a VP16 or GAL4 transcription activation region is constructed from cells that are predicted to express a polypeptide binding to the polypeptide of the present invention. The cDNA library is then introduced into the above yeast cells. A library-derived cDNA is isolated from a detected positive clone. (A positive clone can be confirmed when a polypeptide that binds to the polypeptide of the present invention is expressed within a yeast cell, following which a reporter gene is activated because of the binding of the two.) By introducing the isolated cDNA into *Escherichia coli* for expression, the polypeptide encoded by the cDNA can be obtained. Accordingly, a polypeptide that binds to the polypeptide of the present invention or the gene thereof can be prepared.

Examples of a reporter gene to be used in the 2-hybrid system include, but are not limited to, in addition to an HIS3 gene, an Ade2 gene, a LacZ gene, a CAT gene, a luciferase gene, and a PAI-1 (Plasminogen activator inhibitor type 1) gene. Screening by the 2-hybrid method can also be carried out using mammalian cells in addition to yeast.

A compound that binds to the polypeptide of the present invention can also be screened for using affinity chromatography. For example, the polypeptide of the present invention is immobilized to a carrier of an affinity column and then a sample to be tested, which is predicted to express a polypeptide that binds to the polypeptide of the present invention, is applied. Examples of a sample to be tested in this case include a cell extract and a cell lysate. After application of a sample to be tested, the column is washed, and then a polypeptide that has bound to the polypeptide of the present invention can be prepared.

The amino acid sequence of the thus obtained polypeptide is analyzed and then an oligo DNA is synthesized based on the sequence. A DNA encoding the polypeptide can be obtained by screening a cDNA library using the DNA as a probe.

Furthermore, an example of a method for isolating not only a polypeptide but also a compound (including agonists and antagonists) that binds to the polypeptide of the present invention, which is known by persons skilled in the art, is a method that involves causing a synthetic compound, a natural product bank, or a random phage peptide display library to act on the immobilized polypeptide of the present invention and then screening for a molecule that binds to the polypeptide of the present invention, or a screening method using high throughput based on combinatorial chemistry technology (Wrighton N C; Farrell F X; Chang R; Kashyap A K; Barbone F P; Mulcahy L S; Johnson D L; Barrett R W; Jolliffe L K; Dower W J., Small peptides as potent mimetics of the protein hormone erythropoietin, Science (UNITED STATES) Jul. 26 1996, 273 pp. 458-64; Verdine G L., The combinatorial chemistry of nature, Nature (ENGLAND) Nov. 7 1996, 384, pp. 11-13; Hogan J C Jr., Directed combinatorial chemistry, Nature (ENGLAND) Nov. 7 1996, 384, pp. 17-9).

In the present invention, a biosensor using the surface plasmon resonance phenomenon can also be used as a means for detecting or measuring bound compounds. With such a biosensor, interaction between the polypeptide of the present invention and a compound to be tested can be observed in real time as surface plasmon resonance signals using a fine amount of polypeptides without labeling them (e.g., produced by BIAcore or Pharmacia). Hence, by the use of a biosensor produced by BIAcore or the like, binding between the polypeptide of the present invention and a compound to be tested can be evaluated.

A method for screening for a substance that inhibits the fucose transport activity of the polypeptide of the present invention can be carried out by a method known by persons skilled in the art. For example, the polypeptide of the present invention is expressed on a membrane (e.g., cell membrane, Golgi apparatus membrane, or viral membrane). Fucose labeled with a fluorescent substance or the like is contacted with a substance to be tested and then the amount of incorporated fucose is measured. Thus, a substance that inhibits the fucose transport activity of the polypeptide of the present invention can be screened for.

A compound that can be isolated by the screening according to the present invention is a candidate for regulating the activity of the polypeptide of the present invention and may be applied for the production of an antibody with high cytotoxic activity.

Cytotoxic Activity of Antibody

Antibodies produced by the method of the present invention have enhanced cytotoxic activity.

Examples of cytotoxic activity in the present invention include antibody-dependent cell-mediated cytotoxicity (ADCC) activity and complement-dependent cytotoxicity (CDC) activity. In the present invention, CDC activity means cytotoxic activity of a complement system. ADCC activity means activity to damage a target cell. Specifically, when a specific antibody attaches to a cell surface antigen of a target cell, an Fcγ receptor-retaining cell (e.g., an immunocyte) binds to the Fc portion of the antibody via an Fcγ receptor, damaging the target cell.

Whether or not an antibody has ADCC activity or has CDC activity can be measured by a known method (e.g., Current protocols in Immunology, Chapter 7, Immunologic studies in humans, Editor John E. Coligan et al., John Wiley & Sons, Inc., (1993)).

Specifically, effector cells, a complement solution, and target cells are prepared.

(1) Preparation of Effector Cells

A spleen is extracted from a CBA/N mouse or the like, and then spleen cells are separated in an RPMI1640 medium (produced by GIBCO). After washing with the same medium containing 10% fetal bovine serum (FBS, produced by HyClone), the cells are prepared to a concentration of $5\times10^6$/ml, thereby preparing effector cells.

(2) Preparation of a Complement Solution

Baby Rabbit Complement (produced by CEDARLANE LABORATORIES LIMITED) is diluted 10-fold in a 10% FBS-containing medium (produced by GIBCO), thereby preparing a complement solution.

(3) Preparation of Target Cells

Pancreatic cancer cell lines (e.g., AsPC-1 and Capan-2) are radiolabeled by culturing the cell lines with 0.2 mCi $^{51}$Cr-sodium chromate (produced by Amersham Pharmacia Biotech) in a 10% FBS-containing DMEM medium at 37° C. for 1 hour. After radiolabeling, the cells are washed three times in a 10% FBS-containing RPMI1640 medium and then prepared to a cell concentration of $2\times10^5$/ml, thereby preparing target cells.

Subsequently, ADCC activity or CDC activity are measured. To measure ADCC activity, target cells and antibodies are added in amounts of 50 μl each to a 96-well U-bottomed plate (produced by Beckton Dickinson) and are then allowed to react on ice for 15 minutes. Next, 100 μl of effector cells is added, followed by 4 hours of culture in a carbon dioxide gas incubator. The final antibody concentration is 0 or 10 μg/ml. After culture, 100 μl of the supernatant is collected, and then radioactivity is measured using a gamma counter (COBRAI-IAUTO-GMMA, MODEL D5005, produced by Packard Instrument Company). Cytotoxic activity (%) can be calculated by (A-C)/(B-C)×100. "A" denotes radioactivity (cpm) in each sample, "B" denotes radioactivity (cpm) in a sample supplemented with 1% NP-40 (produced by NACALAI TESQUE, INC.), and "C" denotes radioactivity (cpm) in a sample containing only target cells.

Furthermore, to measure CDC activity, target cells and anti-PepT antibodies are added in amounts of 50 μl each to a 96-well flat-bottomed plate (produced by Becton Dickinson) and are then allowed to react on ice for 15 minutes. Subsequently, 100 μl of a complement solution is added, followed by 4 hours of culture in a carbon dioxide gas incubator. The final antibody concentration is 0 or 3 μg/ml. After culture, 100 μl of the supernatant is collected, and then radioactivity is measured using a gamma counter. Cytotoxic activity can be calculated in a manner similar to that used for measurement of ADCC activity.

EXAMPLES

The present invention will be specifically described in the following examples. However, the examples are not intended to limit the technical scope of the present invention.

Example 1

Obtainment of GDP-Fucose Transporter Gene Fragment from Chinese Hamster Ovary (CHO) Cell Line The cDNA sequence of human GDP-fucose transporter (accession#AF326199) and the same of mouse GDP-fucose transporter (accession#AK050311) were obtained from the NCBI database. After the sequences were analyzed using GENETYX-SV/RC, primers were designed using portions of sequences (FIG. 1) where high homology was noted between the human and mouse sequences. RT-PCR was then carried out using polyA+ RNA extracted from a CHO cell line (DXB11) using an RNA extraction kit (TAKARA: catrimox 14 RNA isolation kit) as a template and an RT-PCR kit (TOYOBO: RT-PCRHigh). The thus obtained fragment was subcloned into pBluescriptSK+. After the sequence thereof was confirmed, it was excised with an appropriate restriction enzyme and then used as a probe for library screening.

Example 2

Cloning of the Full-Length cDNA of GDP-Fucose Transporter

The GDP-fucose transporter fragment obtained in Example 1 was labeled with α32P dCTP using a Random Prime labeling system (Amersham). The CHO-cell-derived cDNA library used herein was specifically derived from the CHO-K1 cell line (LambdaZAP-CMV XR Library: Stratagene Corp.). Screening was carried out basically according to the manuals. Specifically, in primary screening, *Escherichia coli* (XL-1-Blue MRF') was infected with $10^6$ phages and then inoculated together with soft agar on 10 plates. The thus obtained plaques were transferred to nylon membranes (Hybond NX: Amersham). The membranes were subjected to alkaline and neutralization treatment according to a standard method. After UV crosslinking, hybridization was carried out using the above probe. Secondary screening and tertiary screening were carried out for the obtained positive clones. Finally, 9 purified positive clones were obtained. *Escherichia coli* (XLOLR) was infected with each clone and a helper phage (ExAsist interference-resistant helper phage: Stratagene Corp.). The resultants were collected as plasmids (pCMV-Script EX) and then the sequences were examined (FIG. 2). FIG. 1 shows comparison between the mouse transporter gene sequence and the human transporter gene sequence. When compared with the CHO-cell-derived sequence, homology with the human sequence was found to be 85.3% and the homology with the mouse sequence was found to be 91.5%.

Example 3

Cloning of Genomic DNA of GDP-Fucose Transporter

To prepare a gene fragment on the 5' side and the same on the 3' side as probes, primers were designed using the GDP-fucose transporter fragment obtained in Example 1 as a template. The 5' side fragment and the 3' side fragment were obtained by PCR. Regarding primers, a combination (FIG. 3) of the primer for RT-PCR used in Example 1 and a primer (with which sequences corresponding to exon 1 and exon 2 as predicted from a mouse genome can be obtained) was designed. Labeling of the 5' and 3' probes and screening were carried out by the method as shown in Example 2 using a CHO-cell-derived genomic DNA library (CHO-K1 cell line-derived Lambda FIX II Library: Stratagene Corp.). Finally, 11 positive clones were obtained. Of these clones, 7 clones were used for infecting *Escherichia coli* (XL-1 Blue MRA). Phages were collected from 100 mL of a liquid culture and then phage DNA was collected using a QIAGEN Lambda kit (QIAGEN). The thus collected phage DNA was digested with an appropriate restriction enzyme, followed by selection and mapping of independent clones by Southern blot hybridization.

Example 4

Determination of Genomic DNA Sequence of GDP-Fucose Transporter of CHO-K1 Cell

The DNA comprising the CHO genomic gene obtained in Example 3 was digested with various restriction enzymes and then subjected to 0.8% agarose gel electrophoresis. Subsequently, according to a standard method, a restriction enzyme map (FIG. 3) was produced by Southern blotting using the 5' side and the 3' side fragments of the GDP-fucose transporter cDNA obtained in Example 2 as probes. Bands respectively hybridizing to these fragments were excised and then collected using a QIAquick Gel Extraction Kit (QIAGEN) according to the attached manuals. The collected DNA fragments were ligated to pBluescriptSK+ using a Rapid DNA ligation kit (Roche) and then the resultant was introduced into *Escherichia coli* DH5α strain (TOYOBO CO., LTD.). Plasmids were collected from the thus obtained recombinant

*Escherichia coli* and then analyzed using an ABI3100 Genetic Analyzer (FIG. 4, SEQ ID NO: 1).

Example 5

Suppression of GDP-Fucose Transporter Expression in CHO Cell Using RNAi $5\times10^5$ DG44 cells were suspended in an IMDM medium (Invitrogen Corp.) containing 5 mL of 10% FCS (MOREGATE BIOTECH), 200 µmol/L Geneticin (Invitrogen Corp.), and 200 nmol/L MTX. The resultant was then inoculated in a Falcon 25 cm² culture bottle. 24 hours later, synthetic siRNA (sense strand UAA CCU CUG CCU CAA GUA CdTdT (SEQ ID NO: 3) and antisense strand GUA CUU GAG GCA GAG GUU AdTdT (SEQ ID NO: 4)) (B-Bridge International Inc.) for a GDP-fucose transporter were transfected (2 nM to 500 nM) using lipofectamine 2000 (Invitrogen Corp.). At 48 hours after transfection, the cells were collected. RNA was extracted from the cells using an SV total RNA isolation system (Promega Corp.). RT-PCR reaction was carried out using a TaqMan PCR Corereagent kit and TaqMqan Reverse transcription reagents (Applied Biosystems). GDP-fucose transporter expression was quantified using PRISM7700 (Applied Biosystems). As a result, GDP-fucose transporter gene expression was suppressed at the mRNA level.

Figure 5:
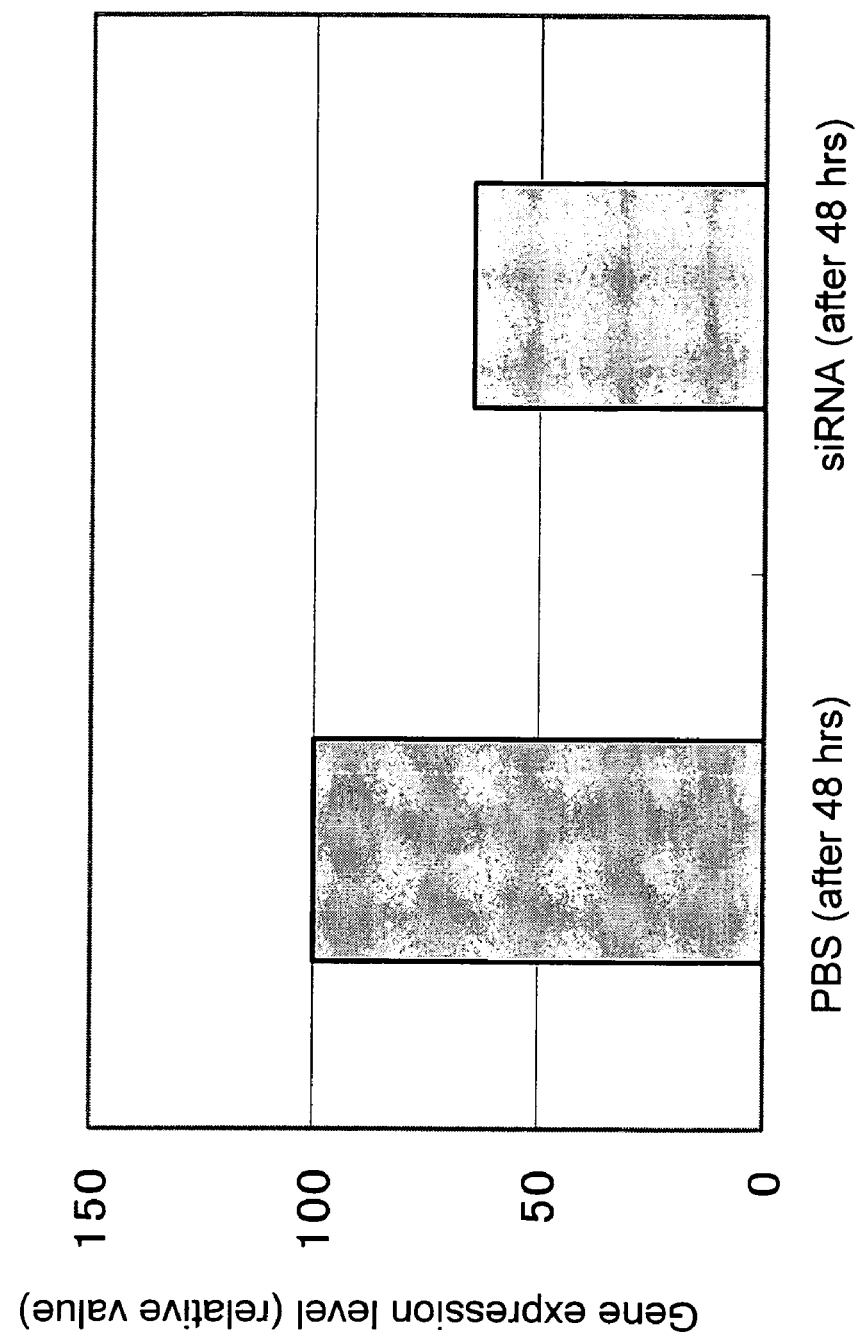
FIG. 5 shows the results of inhibiting a transporter gene using siRNA.

FIG. 5 shows the results. A graph in FIG. 5 shows relative values when GDP-fucose transporter gene expression at 48 hours after transfection of PBS was determined to be 100.

Example 6

Disruption of Fucose Transporter Gene in CHO Cell Construction of Targeting Vector A mouse pgk-1 gene promoter was excised with EcoR I-Pst I from a pKJ2 vector (Popo H, Biochemical Genetics vol. 28, pp. 299-308, 1990) and then cloned into the EcoR I-Pst I site of pBluescript (Stratagene Corp.), thereby producing pBSK-pgk-1. A hygromycin resistance gene ($Hyg^r$) was subjected to PCR using pcDNA3.1/Hygro (Invitrogen Corp.) and Hyg5-AV and Hyg3-BH primers. Thus, an Eco T221 site and a Kozak sequence were added to the 5' side of $Hyg^r$ and a BamH I site was added to the 3' side comprising a region extending to an SV40 polyA addition signal, thereby extracting $Hyg^r$.

```
Forward primer
Hyg5-AV       5'-ATG CAT GCC ACC    (SEQ ID NO: 5)
              ATG AAA AAG CCT GAA
              CTC ACC-3'

Reverse primer
Hyg3-BH       5'-GGA TCC CAG GCT    (SEQ ID NO: 6)
              TTA CAC TTT ATG CTT
              C-3'
```

Figure 6:
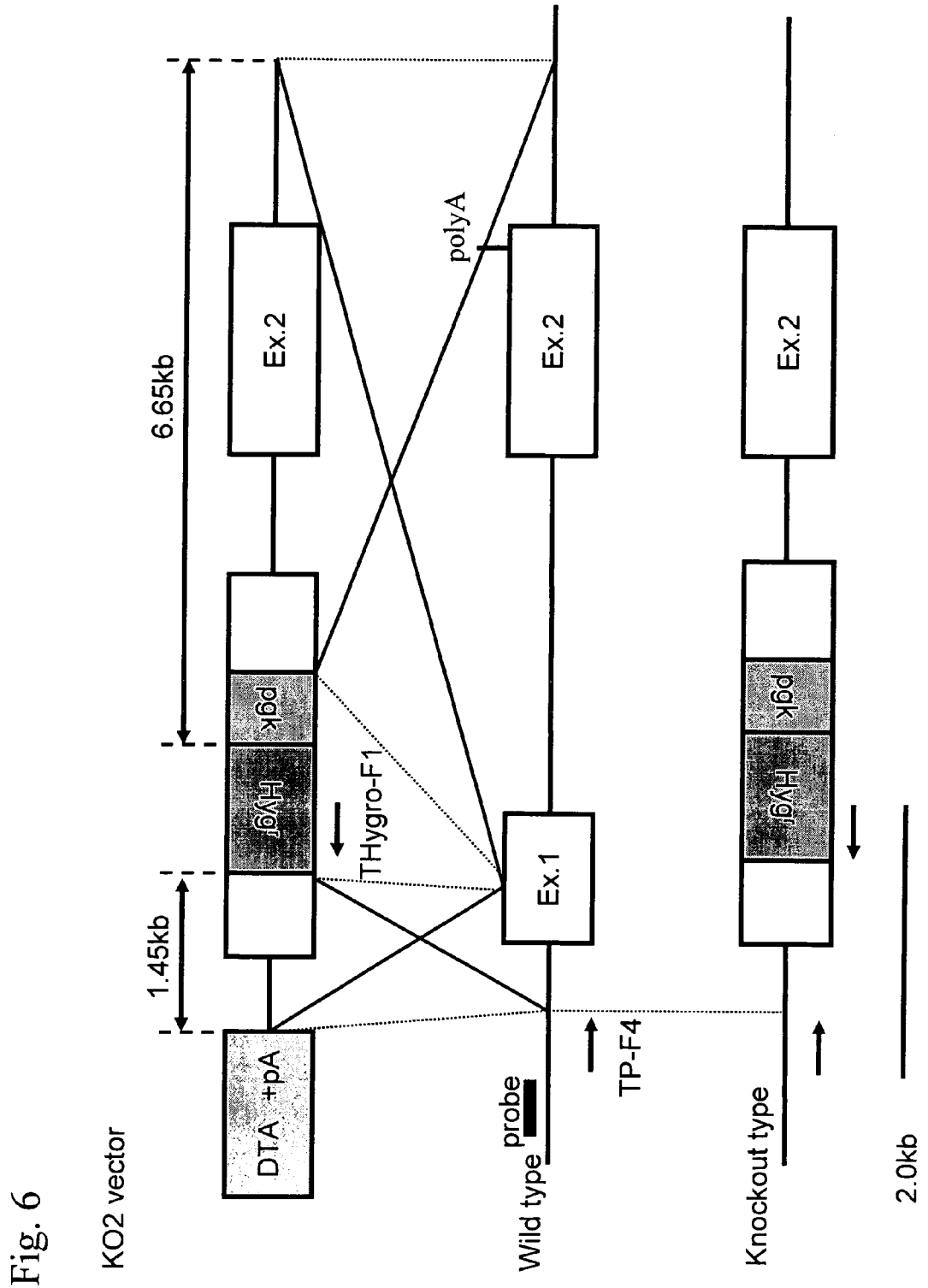
FIG. 6 shows the structure of a targeting (KO2) vector and an outline of PCR screening.

The $Hyg^r$ (Eco T221-BamH I) fragment was inserted into the Pst I-BamH I site of pBSK-PGK, thereby producing pBSK-pgk-1-$Hyg^r$. A targeting vector (hereinafter referred to as the KO2 vector) for a fucose transporter was constructed (FIG. 6) by respectively inserting the 5' side (ranging from No. 2780 Sma I to No. 4232 BamH I in SEQ ID NO: 1), 3' side (ranging from No. 4284 to No. 10934 Sac I), and pgk-1-$Hyg^r$ fragments of the fucose transporter into a pMC1DT-A vector (Yagi T, Proc. Natl. Acad. Sci. U.S.A. vol. 87, pp. 9918-9922, 1990). The KO2 vector was cleaved with Not I and then introduced into cells. By the use of the KO2 vector, the fucose transporter will lack 46 base pairs of exon 1 comprising the initiation codon and lose the relevant functions.

Introduction Into CHO Cells

HT Supplement (100×) (Invitrogen Corp. cat. 11067-030) and penicillin streptomycin (Invitrogen Corp.: cat. 15140-122) were each added to CHO-S-SFMII HT-(Invitrogen Corp.: cat 12052-098) in a volume one-hundredth of the volume of CHO-S-SFMII HT-. The solution was used as media for culture (hereinafter referred to as SFMII (+)). The DXB11 cell line of CHO cells was subcultured and cells after gene transfer were also cultured in SFMII (+). $8\times10^6$ CHO cells were suspended in 0.8 mL of Dulbecco's phosphate buffer (hereinafter abbreviated as "PBS"; Invitrogen Corp.: cat 14190-144). 30 µg of the targeting vector (KO2 vector) was added to the cell suspension. The cell suspension was transferred to a Gene Pulser Cuvette (4 mm) (Bio-Rad Laboratories Inc.: cat. 1652088). After the suspension was allowed to stand on ice for 10 minutes, the vector was introduced into the cells by an electroporation method using GENE-PULSER II (Bio-Rad Laboratories Inc.: code No. 340BR) under the condition of 1.5 kV and 25 µFD. After introduction of the vector, the cells were suspended in 200 ml of SFMII(+) medium. The cells were then inoculated at 100 µl/well to twenty 96-well flat-bottomed plates (IWAKI & CO., LTD.: cat. 1860-096). The cells in the plates were cultured in a $CO_2$ incubator for 24 hours at 37° C., followed by selection using hygromycin B (Invitrogen Corp.: cat. 10687-010). Hygromycin B was dissolved in SFMII(+) to a concentration of 300 µg/ml and then added at 100 µl/well.

Homologous recombinants were screened for by the PCR method. CHO cells used in screening were cultured in a 96-well flat-bottomed plate. After removal of culture supernatants, a buffer for cell lysis was added at 50 µl/well. After incubation at 55° C. for 2 hours, proteinase K was inactivated by subsequent heating at 95° C. for 15 minutes, so as to prepare a template for PCR. The buffer for cell lysis per well was composed of 5 µl of 10× LA buffer II (attached to TaKaRa LA Taq), 2.5 µl of 10% NP-40 (Roche: cat. 1 332 473), 4 µl of proteinase K (20 mg/ml and TaKaRa: cat. 9033), and 38.5 µl of distilled water (NACALAI TESQUE, INC.: cat. 36421-35). A PCR reaction mixture was determined to contain 1 µl of the above PCR sample, 5 µl of 10× LA buffer, 5 µl of $MgCl_2$ (25 mM), 5 µl of dNTP (2.5 mM), 2 µl of each primer (10 µM each), 0.5 µl of LA Taq (5 IU/µl and cat. RR002B), and 29.5 µl of distilled water (total 50 µl). Moreover, PCR conditions consist of pre-heating at 95° C. for 1 minute, 40 amplification cycles (each cycle consisting of 95° C. for 30 seconds and 70° C. for 3 minutes), and additional heating at 70° C. for 7 minutes.

Primers are as shown below. In CHO cell samples wherein homologous recombination has taken place, an approximately 2.0-kb band was amplified. Regarding the primers, TP-F4 was located in the 5' side fucose transporter genomic region outside the KO2 vector and THygro-R1 was located within a hygromycin resistance gene in the KO2 vector.

```
Forward primer
TP-F4         5'-GGA ATG CAG CTT    (SEQ ID NO: 7)
              CCT CAA GGG ACT CGC-
              3'

Reverse primer
THygro-F1     5'-GCA CTC GTC CGA    (SEQ ID NO: 8)
              GGG CAA AGG AAT AGC-
              3'
```

The number of the thus analyzed CHO cells was 537. Of these cells, 17 were considered to be homologous recombinants (homologous recombination efficiency was approximately 3.2% at this time).

Figure 7:
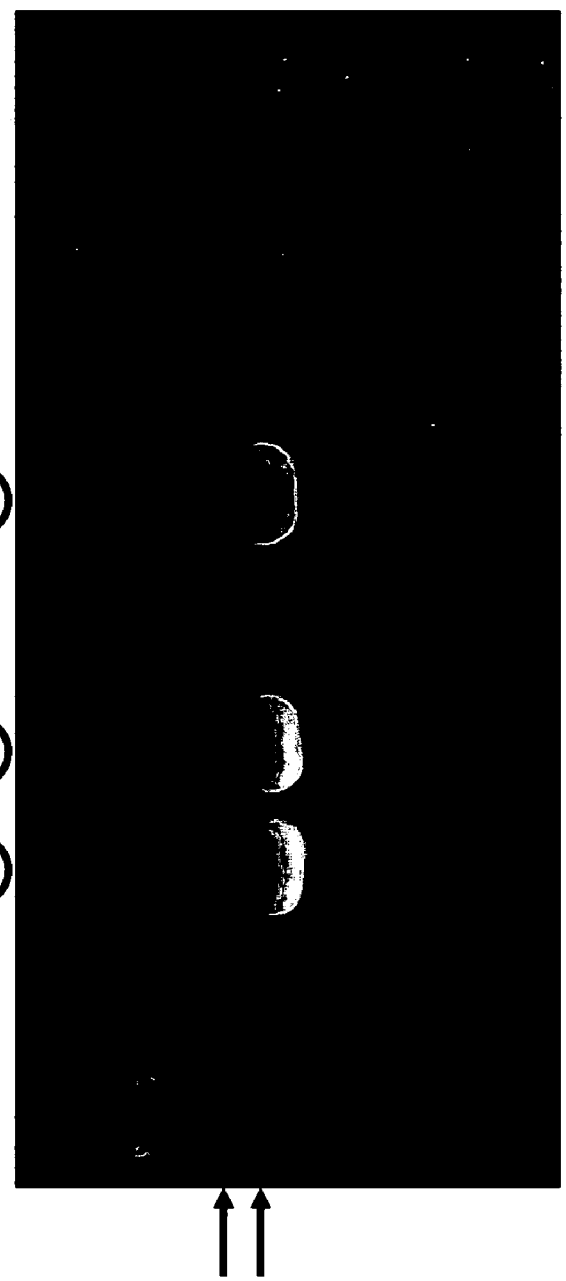
FIG. 7 is a photograph showing the results of PCR screening.

FIG. 7 shows data resulting when the PCR products in the screening were subjected to 1% agarose gel electrophoresis. 2.0-kb bands appeared in samples indicated with "◯." These clones were considered to be homologous recombinants. Next, 2.0-kb bands were excised from the gel and then purified using a Mag Extractor (TOYOBO CO., LTD.: cat. NPK-601). 200 ng of the purified PCR product was subjected to direct sequencing using TP-F4 and THygro-F1. Thus, the PCR product was confirmed to have a nucleotide sequence resulting from homologous recombination, resulting in the conclusion that the product was a homologous recombinant.

Such confirmation was also carried out by the Southern blot method. The cells cultured in a 24-well plate were collected, genomic DNA was prepared according to a standard method, and then Southern blot was carried out. A 387-bp probe was prepared from the region ranging from No. 2, 113 to No.2, 500 of SEQ ID NO: 1 by the PCR method using the following 2 types of primer. The thus prepared probe was used for confirmation by the Southern blot method. The genomic DNA was cleaved with Bgl II or EcoR I.

```
Forward primer
Bgl-F:       5'-TGT GCT GGG AAT    (SEQ ID NO: 9)
             TGA ACC CAG GAC-3'

Reverse primer
Bgl-R:       5'-CTA CTT GTC TGT    (SEQ ID NO: 10)
             GCT TTC TTC C-3'
```

Figure 8:
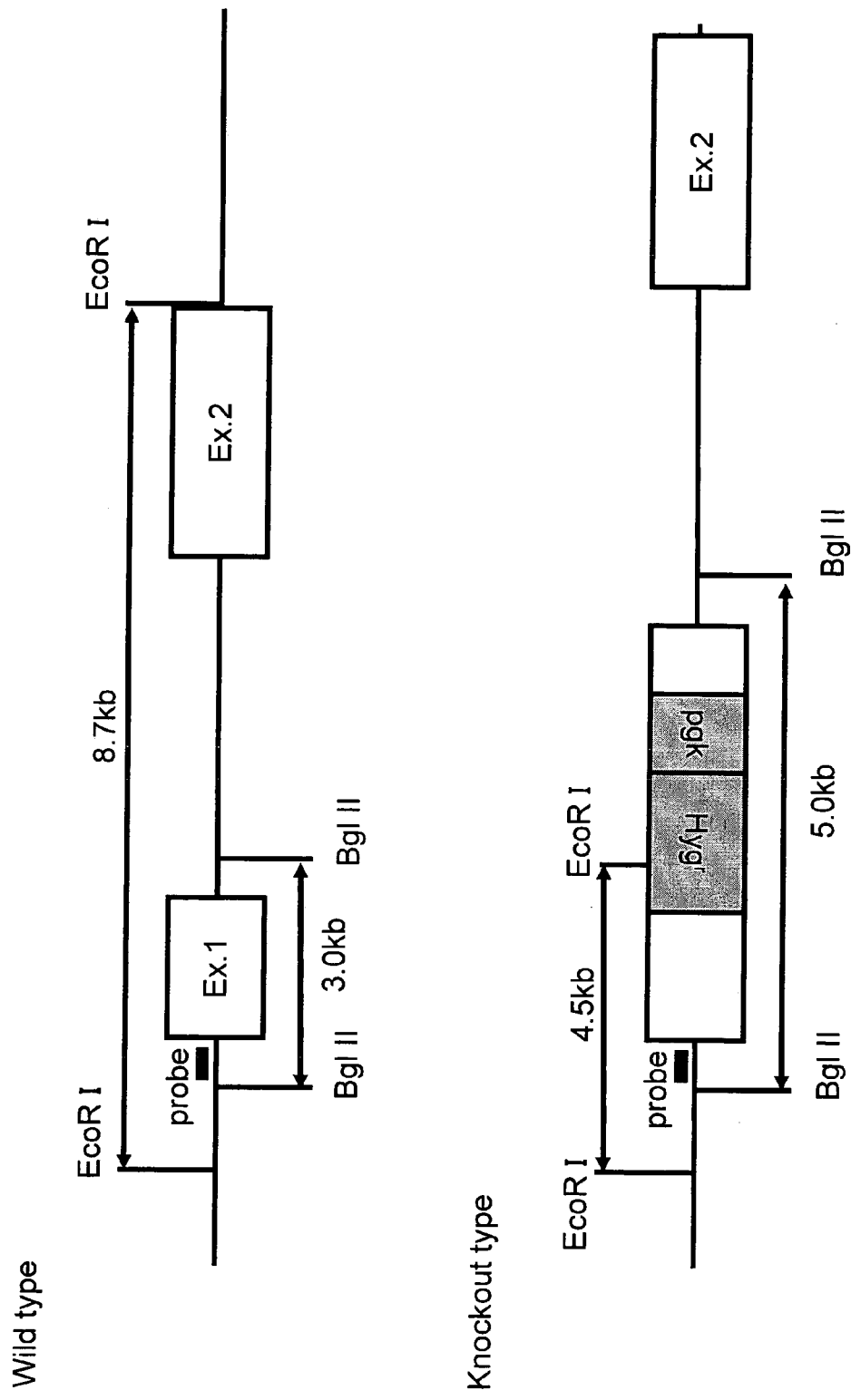
FIG. 8 shows restriction enzyme maps for a wild-type chromosome and a knockout-type chromosome.
Figure 9:
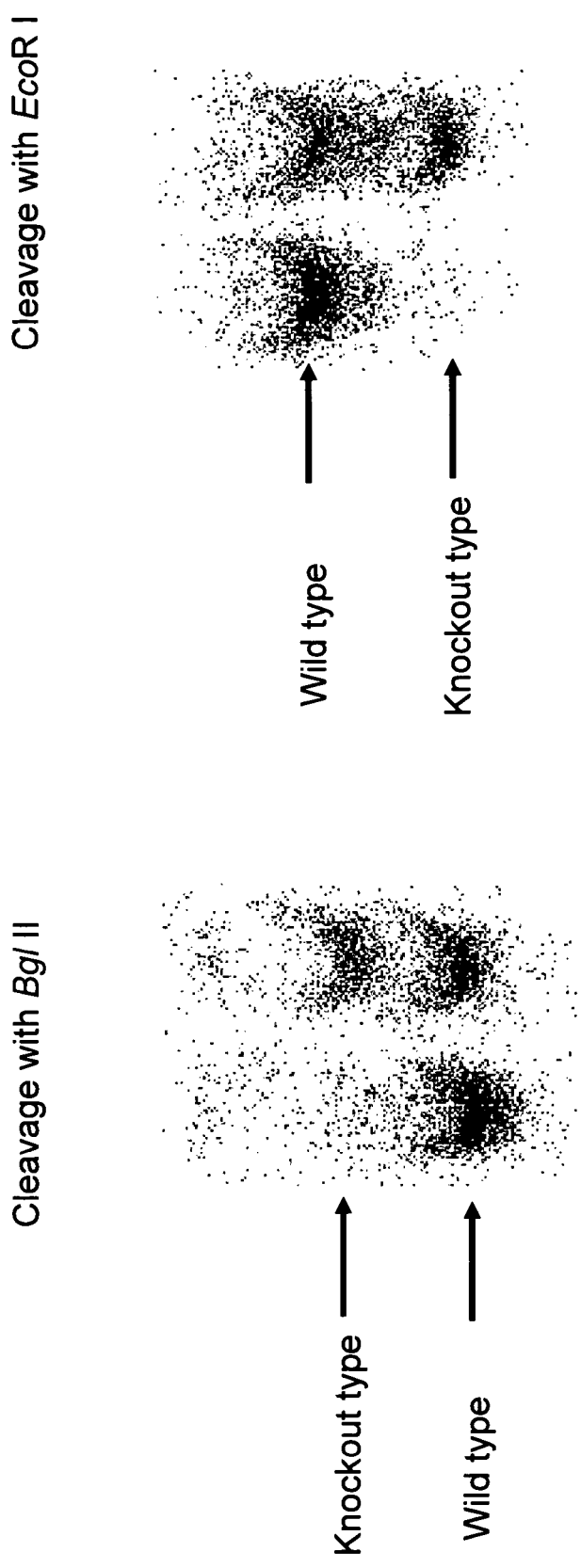
FIG. 9 shows photographs showing the results of carrying out the Southern blot method.

As a result of cleavage with Bgl II, an approximately 3.0-kb band appeared from the chromosome of the original fucose transporter and an approximately 5.0-kb band appeared from the knocked-out chromosome. Furthermore, as a result of cleavage with EcoR I, an approximately 8.7-kb band appeared from the chromosome of the original fucose transporter and an approximately 4.5-kb band appeared from the knocked-out chromosome (FIG. 8). FIG. 9 shows the data when Southern blot was actually carried out.

Sequence Listing Free Text
SEQ ID NOS: 3 and 4: synthetic RNA

INDUSTRIAL APPLICABILITY

According to the present invention, a fucose transporter polypeptide and a fucose transporter gene can be obtained. Furthermore, a recombinant protein-producing cell having a disrupted fucose transporter gene is obtained. When recombinant protein is produced in the cell, a recombinant protein wherein the addition of fucose is lowered or is eliminated can be produced. Particularly when protein is an antibody, cytotoxic activity is enhanced due to lowered fucose addition or elimination of fucose addition. Hence, such protein is useful as an antibody pharmaceutical having an anti-tumor effect.

All publications cited herein are incorporated herein in their entirety. A person skilled in the art would easily understand that various modifications and changes of the present invention are feasible within the technical idea and the scope of the invention as disclosed in the attached claims. The present invention is intended to include such modifications and changes.

The invention claimed is:

1. An isolated Chinese hamster cell, wherein one or more exons of the genomic Chinese hamster fucose transporter gene having the sequence of SEQ ID NO: 1 are disrupted.

2. The isolated Chinese hamster cell according to claim 1, wherein the Chinese hamster cell is a Chinese hamster ovary (CHO) cell.

3. The isolated CHO cell according to claim 2, wherein one or more of the genomic Chinese hamster fucose transporter gene are disrupted by homologous recombination using a gene targeting vector against the sequence in the genomic Chinese hamster fucose transporter gene having the sequence of SEQ ID NO: 1.

4. The isolated Chinese hamster cell according to claim 3, wherein exon 1 is disrupted.

5. The isolated Chinese hamster cell according to claim 3, wherein the Chinese hamster fucose transporter gene is disrupted by a positive selection marker.

6. The isolated Chinese hamster cell according to claim 5, wherein the positive selection marker is a drug resistance gene.

7. The isolated Chinese hamster cell according to claim 5, wherein the positive selection marker is a hygromycin resistance gene or a neomycin resistance gene.

8. The isolated Chinese hamster cell according to claim 5, wherein the positive selection marker disrupts an exon.

9. The isolated Chinese hamster cell according to claim 3, wherein the gene targeting vector comprises,
   a positive selection marker,
   a first nucleotide sequence homologous to at least part of SEQ ID NO:1 that is located 5' of the positive selection marker,
   a second nucleotide sequence homologous to at least part of SEQ ID NO:1 that is located 3' of the positive selection marker,
   a first restriction enzyme site for linearizing the vector located outside the positive selection marker, the first nucleotide sequence and the second nucleotide sequence, and
   a second restriction enzyme site for detecting homologous recombination.

10. The isolated Chinese hamster cell according to claim 9, wherein at least one of the first nucleotide sequence and the second nucleotide sequence is homologous to at least a part of an intron.

11. The isolated Chinese hamster cell according to claim 1 or 2, wherein exon 1 is disrupted.

* * * * *

SEQUENCE LISTING

```
<160> NUMBER OF SEQ ID NOS: 19

<210> SEQ ID NO 1
<211> LENGTH: 10939
<212> TYPE: DNA
<213> ORGANISM: Cricetulus griseus

<400> SEQUENCE: 1
gagctcaatt  aaccctcact  aaagggagtc  gactcgatcc  tttacagaaa  acttgcaaac      60
cctcttggag  tagaaaagta  gtagtatctg  acacaagtat  cagcaaaatg  caaacttctc     120
cccatcccca  gaaaaccatt  ataaaaaccc  ccatatctta  tgcccaactg  tagtgatata     180
ttatttatga  tttattaaaa  cttgcttaag  gattcagaaa  gcaaagtcag  ccttaagcta     240
tagagaccag  gcagtcagtg  gtggtacaca  cctttaatcc  caggactcag  gattaagaag     300
tagacggacc  tctgttagtt  caagtctacc  attacctaca  caagagtgaa  gagtaaccga     360
tctcatgcct  ttgatcccag  cagctgggat  catgtgcatt  caatcccagc  attcgggagt     420
tatataagac  aggagcaagg  tctcagagct  ggcattcatt  ctccagccac  attgaggata     480
ggaaaacatt  gaagtgtcag  gatgctgagg  agaggcagca  gtttgaggtt  tggtagaacc     540
aggatcacct  tttggtctga  ggtagagtaa  gaactgtggc  tggctgcttt  gcttttctga     600
tcttcagctt  gaagcttgaa  ctccaatatt  tgtctctggg  tctattatta  tcatgttaca     660
cctaaactta  aagctgattt  acgcaagaca  gttgtaggtg  gacctttctt  tcctgcccac     720
cagttcccaa  ataactgaca  cggagactca  atattaatta  taaatgattg  gttaatagct     780
cagtcttgtt  actggctaac  tcttacattt  taaattaact  catttccatc  cctttacttg     840
```

-continued

```
ctgccatgtg gttcatggct tgttcaagtc ctgcttcttc tgtctctggc tggtgatgcc    900
tctggttctg cccttttatcc cagaattctc ctagtctggc tctcctgccc agctataggc    960
cagtcagctg tttattaacc aatgagaata atacatattt atagtgtaca aagattgctc   1020
ctcaacaccc aattttttat gtgcaacctg agaatctgga ctcattgccc tcatgcttgc   1080
agaggcggca cccttaccca ctaagccacc tttctagccc tgttgctttt gtttttttgag  1140
acaggttcca ctatgtagcc caggctggcc tcaaactgac cattctcctg cctaaacctc   1200
ccgaacactg gaattatagt caaggcctac ctgccctggc attttcacac ttttattttcc  1260
tggctgagtc cattgacttt acactcatca aggttgaacc agttggagtt taattacagt   1320
gccaatcgca ctgaatccca cataatcaaa caacttcaag gaagcaaaaa accagtttt    1380
cctgaagatc aatgtcagct tgcctgattc agaatagacc cccgaaaaaa ggcaaatgct   1440
tgataaccaa tttcttctta ttgttcaatc ccctgctgct gtgtgtaagc tcctgagaaa   1500
ggacagtaag gggacattca tgatcagaga aagagcccca actccccccc cagccccacc   1560
cccaccctgt ccacagtctg ttggtttggt ttccccctgg ctgacaccca gaaatcacaa   1620
cataatcacc taggtcactg taacaagttc cttctctggaa aatgctacaa atgatattgg   1680
taacatgagt aatgaataat gcctggagtc caactccctt gtgacccagc aatgttttcc   1740
gtgggtgctc ccttccccag ctgcaggcct gacatgtacc ttaaaaagcc tcccctggag   1800
gacagaattt tgtgggtact atagtgttct cacaaatact tcccctaata cccttactta   1860
gttaccataa ataacatgca gcccctggtg aggcacacag ggctccaatg tacagcttct   1920
cagacactgc aggaaccttc ctctcctaat gcagcactgg tctcttcagg ctggacagca   1980
ggaacccata ccactccaat cctagtgtgg agtagagctg tctacgaaaa ccagcagatc   2040
tatagctaaa tgtgtttcaa ttttatgctt tgacaaattg tactgacccc accccaccc    2100
cttccccctt gctgtgctgg gaattgaacc caggaccttg tgcatgccag gcaagtactc   2160
taacactgag ctatagcccc aatctttcat ccaagtctct atgtgtgccc cactcgctt    2220
tttattttga gacaaaaggt tcttattttg agataaggtc tcactatgtt gccttgactt   2280
tttttttttt ttttttttga actttgacc ttcctacctc agctgagact caagtctttt   2340
taccatcagg cccggctgat ggtaaaataa cagtatttga aatagtttaa acacatcatc   2400
ttaatggtca accacacaat ttccgaaatg ttgctggctc agtctggggc aaacctgtcc   2460
gccccaacat tggtgctagg aagaaagcac agacaagtag ccctcccagc tcaggagtaa   2520
aagacctgga gggggtggcc cacttcggtc aagttcacgg gatggggagg ggtaccctcc   2580
tccagtagtg gtggtatttg gcagttcctc caccgacgcc ctctggaagc acctgcttgg   2640
acccgcaaag ccaggaatgc agcttcctca agggactcgc cagcgagggt aacaggacag   2700
aggcgtccca gagggctggg gcggaaggg ggaagacagg gtcggcctta gatagggcaa    2760
agggccttct ggctgtgttc ccggggtaac cgccccacca cgcctggagc cgacgtggc    2820
gagcgatggg gacagcgagc aggaagtcgt actggggagg gccgcgtagc agatgcagcc   2880
gagggcggcg ctgccaggta cacccgaggg cacccgcgggg gtgagcgcca ggtccctgaa   2940
ccagccaggc ctccagagcc gagtccggcg gaccgacggt acgttctgga atgggaaggg   3000
atccgggaca ccgaattgct gcattgaggg gctcagaggt tctgatgtgg gagtccagaa   3060
agggttttat ctaccggagg tgatgtgact tccggcctct ggaagtgctg ttggagtctc   3120
tgggaccttg ggtcctctcg actaggtttg gaagggggtga aatagggta gggagaaagg   3180
agaggactgc agcaatgtct tcccgaacga cctgggttcg ggagggggtcg aaggacaagg  3240
```

-continued

```
ggctgttgtg gggggtcttc agacgcggag gggtggtatt ctattttctg ggaagatggt    3300
gtcgatgcac ttgaccaagt ctagtcgatc tgaagaggct aggggaacag acagtgagag    3360
aggatggtgg agggagtggc agaacccttc cagaaactgg gagaggctct agcacctgca    3420
accccttccc tggcctccgg ggagtcccag aagagggcag gaccatggac acaggtgcat    3480
tcgtgccggc gcgctccggc ctggcgaagg tgcgcgctct tggaggccgc gggagggcca    3540
gacgcgcgcc cggagagctg gcccttaagg ctacccggga ggcgtgtcag gaaatgcgcc    3600
ctgagcccgc ccctcccgga acgcggcccg agacctggca agctgagacg gaactcggaa    3660
ctagcactcg gctcgcggcc tcggtgaggc cttgcgcccg ccatgcctct gtcattgccc    3720
ctcgggccgc ctccctgaac ctccgtgacc gccctgcagt cctccctccc cccttcgac     3780
tcggcgggcg cttccgggcg ctcccgcagc ccgccctcca cgtagcccac acctccctct    3840
cggcgctccg cttcccacgc ggtccccgac ctgttctttc ctcctccacc ctgcccttct    3900
gtccctctcc cttcctttct cccctcgact cgtcccatt  aggcaacagc cctgtggtc     3960
cagccggcca tggctgtcaa ggctcacacc cttagctagg ccccttctcc cttccctggg    4020
tcttgtctca tgacccctg  ccccgcccgg gagcgagcgc gatgtggagc agtgcctctg    4080
gcaagcagaa cttcacccaa gccatgtgac aattgaaggc tgtaccccca gaccctaaca    4140
tcttggagcc ctgtagacca gggagtgctt ctggccgtgg ggtgacctag ctcttctacc    4200
accatgaaca gggcccctct gaagcggtcc aggatcctgc gcatggcgct gactggaggc    4260
tccactgcct ctgaggaggc agatgaagac agcaggaaca agccgtttct gctgcgggcg    4320
ctgcagatcg cgctggtcgt ctctctctac tgggtcacct ccatctccat ggtattcctc    4380
aacaagtacc tgctggacag ccctcccctg cagctgata  cccctatctt cgtcactttc    4440
taccaatgcc tggtgacctc tctgctgtgc aagggcctca gcactctggc cacctgctgc    4500
cctggcaccg ttgacttccc caccctgaac ctggaccta  aggtggcccg cagcgtgctg    4560
ccactgtcgg tagtcttcat tggcatgata agtttcaata acctctgcct caagtacgta    4620
ggggtggcct tctacaacgt ggggcgctcg ctcaccaccg tgttcaatgt gcttctgtcc    4680
tacctgctgc tcaaacagac cacttccttc tatgccctgc tcacatgtgg catcatcatt    4740
ggtgagtggg gccgggggc  tgtgggagca ggatgggcat cgaactgaag ccctaaaggt    4800
caacactgta ggtacccttta cttactgtcc caggtcccttt gcatcagcag ttacaggaag    4860
agccctgtag aaaacaaata acttccttat ggtcattcaa caagttaggg acccagccag    4920
ggtgaaaata atgttagcag caactacagc aaagatggct ctcgccactt gcatgattaa    4980
aatgtgccag gtactcagat ctaagcattg gatccacatt aactcaacta atccctatta    5040
caaggtaaaa tatatccgaa ttttacagag ggaaaaccaa ggcacagaga ggctaagtag    5100
cttgaccagg atcacacagc taataatcac tgacatagct gggatttaaa cataagcagt    5160
tacctccata gatcacacta tgaccaccat gccactgttc cttctcaaga gttccaggat    5220
cctgtctgtc cagttctctt taaagaggac aacacatctg acattgctac cttgaggtaa    5280
catttgaaat agtgggtaga catatgtttt aagttttatt cttactttt  atgtgtgtgt    5340
gtttgggggg ccaccacagt gtatgggtgg agataagggg acaacttaag aattggtcct    5400
ttctcccacc acatgggtgc tgaggtctga actcaggtca tcaggattgg cacaaatccc    5460
tttacccact gagccatttc actggtccaa tatatgtgtg cttttaagag ctttaacta     5520
ttttcccaga tgtgaatgtc ctgctgatca ttatccccctt ttacccggaa gccctctggg    5580
```

```
aggtgccatc cctgtggtcg tctgcataca aatggggaaa ctgcaactca gagaaacaag   5640
gctacttgcc agggccccac aagtaagata ggctgggatg ccatcccaga ctggccacac   5700
tccctggcct gtgcttcaag ccagtttact ttgttcctgc ccattggaag ttagcatgtt   5760
gcagtcaaac acaataacta caggccaaaa gtgcttttaa attaaagtca gatgaacttt   5820
taaacatcca gagctcctca actgcaggag ttacaacctg attctgcaac catctttgca   5880
gtgcccggta gtcatatgta gctagaggct cttggctagg acagcatgtg ttaggaaaca   5940
tctggccctg agatcattga attgagtgac tgctgggtga caaagaccaa ggcatccgtt   6000
ccctgagagt cctgggcaag cagcaatgtg accttcattt gtacctactc aggttcttta   6060
tctgtcctgt ttgacctact tagtctcctc tggtgtctca gaggcccagg ctgggtactc   6120
tggatgtcag gatcaggcca atgcgcacat ctgcccctaga aatgtcccccc tggttgagca   6180
gctcctgaat ccatcggtaa agggtctgga ccagggagga gtcagataaa aagctgacag   6240
cactgggga ctccatgggg aactcccacc tgccccccaca catccatcct aagagaactg   6300
gtattccttg tttcctcttt gtcctacaag gcaccctggg atcccacttc agtctcccag   6360
ccttgccagg gttagagggc atgagcctcc ttgtggggaa tttagatgca agaaggtaca   6420
gtcactagag aacctgagct cagatcccca agtaaccag tacctgatag tgaggcagct   6480
gagaaccgca gcagcctgcc tgagtggctg aactctgcgg cctccggaac tggccccaac   6540
tgttgggtct cctcttcctt cctcctgtga gggagggccc atctctgata agtgctgtgg   6600
ggactctaga gtaggagga ggaggagcaa tctaagcagg ccttactgag aagtccttgc   6660
tggcatgtgg ctgcctgagg agtacagact gggaacaccc atttgaatga gtaaggtttt   6720
tcctgaaggc catggggagc cacggaggaa aatcatttta gttacaagac aaagagtaga   6780
ttggttaaca tgggagcaag gacatggccc caattttcat agatgaagga aattggaact   6840
cagagaggtt aagtaacttc tcccaaatag ctcagcttca aaatcacaga acagtcagag   6900
tctagatctc tctgatgcct gtgatggtcc tgccattcca tgttgctgat ccctgtggca   6960
tcagtaagcc tctaccttgt gggaatgcag gatctaaatg aagagaggaa gtgctggccc   7020
catgctgtgg tctggaaagc tatgcaggct cttttgagcag agagtgaccc acaagtgaat   7080
agagtcctat gagactcaaa gcaacatcca cccttaagca gctctaacca aatgctcaca   7140
ctgagggagc caaagccaag ttagagtcct gtgcttgccc aaggtcactt tgcctggccc   7200
tcctcctata gcacccgtgt tatcttatag ccctcattac agtgattaca attataatta   7260
gagaggtaac agggccacac tgtccttaca cattcccctg ctagattgta gctgggagag   7320
ggggagatgt aggtggctgg gggagtggga gggaagatgc agattttcat tctgggctct   7380
actccctcag ccatttttttg gtgtgggagt tagactttgg atatgttgat gatgaggtaa   7440
gggccacaga acagtctgaa ctgtggtatc agaatcctgt ccctctccct ctctcctcat   7500
ccctcttcac cttgtcactc ctctgtctgc tacaggtggt ttctggctgg gtatagacca   7560
agagggagct gagggcaccc tgtccctcat aggcaccatc ttcggggtgc tggccagcct   7620
ctgcgtctcc ctcaatgcca tctataccaa gaaggtgctc ccagcagtgg acaacagcat   7680
ctggcgccta accttctata caatgtcaa tgcctgtgtg ctcttcttgc ccctgatggt   7740
tctgctgggt gagctccgtg ccctccttga ctttgctcat ctgtacagtg cccacttctg   7800
gctcatgatg acgctgggtg gcctcttcgg ctttgccatt ggctatgtga caggactgca   7860
gatcaaattc accagtcccc tgaccccaca tgtatcaggc acagccaagg cctgtgcgca   7920
gacagtgctg gccgtgctct actatgaaga gactaagagc ttcctgtggt ggacaagcaa   7980
```

```
cctgatggtg ctgggtggct cctcagccta tacctgggtc aggggctggg agatgcagaa    8040
gacccaagag gaccccagct ccaaagaggg tgagaagagt gctattgggg tgtgagcttc    8100
ttcagggacc tgggactgaa cccaagtggg gcctacacag cactgaaggc ttcccatgga    8160
gctagccagt gtggccctga gcaatactgt ttacatcctc cttggaatat gatctaagag    8220
gagccagggt ctttcctggt aatgtcagaa agctgccaaa tctcctgtct gccccatctt    8280
gttttgggaa aaccctacca ggaatggcac ccctacctgc ctcctcctag agcctgtcta    8340
cctccatatc atctctgggg ttgggaccag ctgcagcctt aagggctgg attgatgaag     8400
tgatgtcttc tacacaaggg agatgggttg tgatcccact aattgaaggg atttgggtga    8460
ccccacacct ctgggatcca gggcaggtag agtagtagct taggtgctat taacatcagg    8520
aacacctcag cctgcctttg aagggaagtg ggagcttggc caagggagga aatggccatt    8580
ctgccctctt cagtgtggat gagtatggca gacctgttca tggcagctgc acctggggt    8640
ggctgataag aaaacattca cctctgcatt tcatatttgc agctctagaa cggggagag     8700
ccacacatct tttacgggtt aagtagggtg atgagctcct ccgcagtccc taaccccagc    8760
tttacctgcc tggcttccct tggcccagct acctagctgt actccctttc tgtactcttc    8820
tcttctccgt catggcctcc cccaacacct ccatctgcag gcaggaagtg gagtccactt    8880
gtaacctctg ttcccatgac agagcccttt gaatacctga accctcatg acagtaagag     8940
acatttatgt tctctgggc tgggctgaa ggagcccact ggttctcact tagcctatct      9000
ggctcctgtc acaaaaaaaa aaaagaaaa aaaaaagca taaaccaagt tactaagaac      9060
agaagttggt ttataacgtt ctggggcagc aaagcccaga tgaagggacc catcgaccct    9120
ctctgtccat atcctcatgc tgcagaagta caggcaagct cctttaagcc tcatatagga    9180
acactagcct cactcatgag ggttttactc catgacctgt caacctcaaa gccttcaaca    9240
tgaggactcc aacgtaaatt tggggacaga agcactcaga ccatacccca gcaccacacc    9300
ctcctaacct cagggtagct gtcattctcc tagtctcctc tcttgggcct ttagaacccc    9360
catttccttg gggtaatgtc tgatgttttt gtccctgtca taaaagatg gagagactgt     9420
gtccagcctt tgattcctac ttcctacaat cccaggttct aatgaagttt gtggggcctg    9480
atgccctgag ttgtatgtga tttaataata aaaagcaag atacagcatg tgtgtggact     9540
gagtgagggc cacagggatc taaaagccaa gtgtgagggg acccagctac agcaggcagc    9600
atcctgagcc tggaatctct tcaggacaag aattctccat atacctacct actctgggga    9660
gtaggtggcc agagttcaag cttcccttag taccaactac cactggctgt gctcttactg    9720
aaggcagaca tggcactgag tgctgtccat ctgtcactca tctccacagc cattcctaat    9780
gtgtggggtg ggagccatca ccaaaccca ttttcagata aggacacagg ctcagagagg      9840
cttgtgtgga gaaagtagc agcagaattc agagagctgg gtctcctgca gcaccttgga    9900
ctgccagcag ccacagtgct tgtcacacag cacatactca aaagaatgcc agcccctca     9960
gcctagagtg cctggccttt ctttcagatg aggaagaggg tcaaagctgt tagcttgccc    10020
accatatgac cacatacatg accaacagct tgagggaggg aggattactg tggctcccag    10080
cctgagaggt gggacaccca aatgtattag gtccttgaat cagggctgac cttgtgattc    10140
agtcactcct accagaatgc tggggaatgg ggatgccaaa ggcaaggag ctttctaag      10200
gtgtggtgta agataggcat ttctgcttcc atgtacacct gtgagcagag taggaaggcc    10260
ctgtggagaa tatatcccac aaaccagtag cccttcctgg cagtgggtga atactgccac    10320
```

```
cctatacccc tatgcaaggc cagtagaacc acccaaccca caacatctag agaaattaca    10380
ggtcatctta agcctctaaa ttgtggagaa actcgacatg cgcacgattc ctaacctgct    10440
agcctagggt gcggggtgga taatttaagg aaactggggt ttcttataga atcggaggct    10500
ccatgaagtc accctgacaa gaggtcagca atagccagca gcagtggcta ctcctaagcc    10560
tccagacaga gcaccctgtg aatgtacctt attctcacat ctgggtgtct ataggtgtga    10620
ctgggtcaga tgtcacccag gccattgcaa tgggccctta gccccatggg gtgttgggat    10680
agcagccaag cagctcccat gctgagatac tgcctgcagt agactgatgg ataagaaaac    10740
aaggcccaaa atgttttctt tccagacttg atctttcttt gttcaaaaat gctgttttcc    10800
cttaaacttg cccaaaccca ttgttttgca gttgaggaaa ataaggcata gaaagattaa    10860
aggaagtttc tgaggttaca gagcaaagta ctggcttcac ctgaaataga caggtgtgcc    10920
ctgatcctga tttgagctc                                                 10939
```

<210> SEQ ID NO 2
<211> LENGTH: 352
<212> TYPE: PRT
<213> ORGANISM: Cricetulus griseus

<400> SEQUENCE: 2

```
Met Ala Leu Thr Gly Gly Ser Thr Ala Ser Glu Glu Ala Asp Glu Asp
 1               5                  10                  15

Ser Arg Asn Lys Pro Phe Leu Leu Arg Ala Leu Gln Ile Ala Leu Val
                20                  25                  30

Val Ser Leu Tyr Trp Val Thr Ser Ile Ser Met Val Phe Leu Asn Lys
            35                  40                  45

Tyr Leu Leu Asp Ser Pro Ser Leu Gln Leu Asp Thr Pro Ile Phe Val
        50                  55                  60

Thr Phe Tyr Gln Cys Leu Val Thr Ser Leu Leu Cys Lys Gly Leu Ser
 65                  70                  75                  80

Thr Leu Ala Thr Cys Cys Pro Gly Thr Val Asp Phe Pro Thr Leu Asn
                85                  90                  95

Leu Asp Leu Lys Val Ala Arg Ser Val Leu Pro Leu Ser Val Val Phe
            100                 105                 110

Ile Gly Met Ile Ser Phe Asn Asn Leu Cys Leu Lys Tyr Val Gly Val
        115                 120                 125

Ala Phe Tyr Asn Val Gly Arg Ser Leu Thr Thr Val Phe Asn Val Leu
    130                 135                 140

Leu Ser Tyr Leu Leu Leu Lys Gln Thr Thr Ser Phe Tyr Ala Leu Leu
145                 150                 155                 160

Thr Cys Gly Ile Ile Ile Gly Gly Phe Trp Leu Gly Ile Asp Gln Glu
                165                 170                 175

Gly Ala Glu Gly Thr Leu Ser Leu Ile Gly Thr Ile Phe Gly Val Leu
            180                 185                 190

Ala Ser Leu Cys Val Ser Leu Asn Ala Ile Tyr Thr Lys Lys Val Leu
        195                 200                 205

Pro Ala Val Asp Asn Ser Ile Trp Arg Leu Thr Phe Tyr Asn Asn Val
    210                 215                 220

Asn Ala Cys Val Leu Phe Leu Pro Leu Met Val Leu Leu Gly Glu Leu
225                 230                 235                 240

Arg Ala Leu Leu Asp Phe Ala His Leu Tyr Ser Ala His Phe Trp Leu
                245                 250                 255

Met Met Thr Leu Gly Gly Leu Phe Gly Phe Ala Ile Gly Tyr Val Thr
```

-continued

```
                    260                 265                 270
Gly Leu Gln Ile Lys Phe Thr Ser Pro Leu Thr His Asn Val Ser Gly
            275                 280                 285
Thr Ala Lys Ala Cys Ala Gln Thr Val Leu Ala Val Leu Tyr Tyr Glu
        290                 295                 300
Glu Thr Lys Ser Phe Leu Trp Trp Thr Ser Asn Leu Met Val Leu Gly
305                 310                 315                 320
Gly Ser Ser Ala Tyr Thr Trp Val Arg Gly Trp Glu Met Gln Lys Thr
                325                 330                 335
Gln Glu Asp Pro Ser Ser Lys Glu Gly Glu Lys Ser Ala Ile Gly Val
            340                 345                 350

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence:Synthetic
      RNA

<400> SEQUENCE: 3
uaaccucugc cucaaguaca gc                                              22

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence:Synthetic
      RNA

<400> SEQUENCE: 4
guacuugagg cagagguua                                                  19

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 5
atgcatgcca ccatgaaaaa gcctgaactc acc                                  33

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 6
ggatcccagg ctttacactt tatgcttc                                        28

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 7
ggaatgcagc ttcctcaagg gactcgc                                         27
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 8
gcactcgtcc gagggcaaag gaatagc                                           27

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 9
tgtgctggga attgaaccca ggac                                              24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 10
ctacttgtct gtgctttctt cc                                                22

<210> SEQ ID NO 11
<211> LENGTH: 1095
<212> TYPE: DNA
<213> ORGANISM: Homo sapiens

<400> SEQUENCE: 11
atgaataggg cccctctgaa gcggtccagg atcctgcaca tggcgctgac cggggcctca        60 gaccccctg cagaggcaga ggccaacggg gagaagccct ttctgctgcg ggcattgcag        120
atcgcgctgg tggtctccct ctactgggtc acctccatct ccatggtgtt ccttaataag       180
tacctgctgg acagcccctc cctgcggctg acacccccca tcttcgtcac cttctaccag       240
tgcctggtga ccacgctgct gtgcaaaggc ctcagcgctc tggccgcctg ctgccctggt       300
gccgtggact tccccagctt gcgcctggac ctcagggtgg cccgcagcgt cctgcccctg       360
tcggtggtct tcatcggcat gatcaccttc aataacctct gcctcaagta cgtcggtgtg       420
gccttctaca atgtgggccg ctcactcacc accgtcttca cgtgctgct ctcctacctg        480 ctgctcaagc agaccaccct cttctatgcc ctgctcacct gcggtatcat catcggggc        540 ttctggcttg gtgtggacca ggagggggca gaaggcaccc tgtcgtggct gggcaccgtc       600
ttcggcgtgc tggctagcct ctgtgtctcg ctcaacgcca tctacaccac gaaggtgctc       660
ccggcggtgg acggcagcat ctggcgcctg actttctaca caacgtcaa cgcctgcatc        720 ctcttcctgc ccctgctcct gctgctcggg gagcttcagg ccctgcgtga ctttgcccag       780
ctgggcagtg cccacttctg ggggatgatg acgctgggcg gcctgtttgg cttttgccatc     840 ggctacgtga caggactgca gatcaagttc accagtccgc tgacccacaa tgtgtcgggc       900

-continued

| | |
|---|---|
| acggccaagg cctgtgccca gacagtgctg gccgtgctct actacgagga gaccaagagc | 960 |
| ttcctctggt ggacgagcaa catgatggtg ctgggcggct cctccgccta cacctgggtc | 1020 |
| aggggctggg agatgaagaa gactccggag gagcccagcc ccaaagacag cgagaagagc | 1080 |
| gccatggggg tgtga | 1095 |

<210> SEQ ID NO 12
<211> LENGTH: 1053
<212> TYPE: DNA
<213> ORGANISM: Mus musculus

<400> SEQUENCE: 12

| | |
|---|---|
| atggcgctga ctggagtctc tgctgtctcc gaggagtcag agagcgggaa caagccattt | 60 |
| ctgctccggg ctctgcagat cgcgctggtg gtctctctct actgggtcac ctccatttcc | 120 |
| atggtattcc tcaacaagta cctgctggac agcccctccc tgcagctgga taccccatt | 180 |
| tttgtcacct tctaccaatg cctggtgacc tcactgctgt gcaagggcct cagcactctg | 240 |
| gccacctgct gccccggcat ggtagacttc cccacccaa acctggacct caaggtggcc | 300 |
| cgaagtgtgc tgccgctgtc agtggtcttt atcggcatga taccttcaa taacctctgc | 360 |
| ctcaagtacg taggggtgcc cttctacaac gtgggacgct cgctcaccac cgtgttcaac | 420 |
| gttcttctct cctacctgct gctcaaacag accacttcct tctatgccct gctcacctgc | 480 |
| ggcgtcatca ttggtggttt ctggctgggt atagaccaag aaggagctga gggaaccttg | 540 |
| tccctgacgg gcaccatctt cggggtgctg ccagcctct cgtctccct caatgccatc | 600 |
| tataccaaga aggtgctccc tgcagtagac cacagtatct ggcgcctaac cttctataac | 660 |
| aatgtcaatg cctgcgtgct cttcttgccc ctgatgatag tgctgggcga gctccgtgcc | 720 |
| ctcctggcct tcactcatct gagcagtgcc cacttctggc tcatgatgac gctgggtggc | 780 |
| ctgtttggct ttgccatcgg ctatgtgaca ggactgcaga tcaaattcac cagtcccctg | 840 |
| acccataacg tgtcaggcac ggccaaggcc tgtgcacaga cagtgctggc cgtgctctac | 900 |
| tacgaagaga ttaagagctt cctgtggtgg acaagcaacc tgatggtgct gggtggctcc | 960 |
| tccgcctaca cctgggtcag gggctgggag atgcagaaga cccaggagga ccccagctcc | 1020 |
| aaagatggtg agaagagtgc tatcagggtg tga | 1053 |

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 13

| | |
|---|---|
| tgcagatcgc gctggtggtc tc | 22 |

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 14

| | |
|---|---|
| gccccctgacc caggtgtagg c | 21 |

<210> SEQ ID NO 15
<211> LENGTH: 2424

```
<212> TYPE: DNA
<213> ORGANISM: Cricetulus griseus

<400> SEQUENCE: 15
gattcggcac gaggcgctcc gcttcccacg cggtccccga cctgttcttt cctcctccac     60
cctgcccttc tgtccctctc ccttcctttc tccctcgac tcgtccctat taggcaacag     120
cccctgtggt ccagccggcc atggctgtca aggctcacac ccttagctag gccccttctc    180
ccttccctgg gtcttgtctc atgaccccct gccccgcccg ggagcgagcg cgatgtggag    240
cagtgcctct ggcaagcaga acttcaccca agccatgtga caattgaagg ctgtaccccc    300
cagaccctaa catcttggag ccctgtagac cagggagtgc ttctggccgt ggggtgacct    360
agctcttcta ccaccatgaa cagggcccct ctgaagcggt ccaggatcct gcgcatggcg    420
ctgactggag gctccactgc ctctgaggag gcagatgaag acagcaggaa caagccgttt    480
ctgctgcggg cgctgcagat cgcgctggtc gtctctctct actgggtcac ctccatctcc    540
atggtattcc tcaacaagta cctgctggac agcccctccc tgcagctgga taccctatc     600 ttcgtcactt tctaccaatg cctggtgacc tctctgctgt gcaagggcct cagcactctg    660
gccacctgct gccctggcac cgttgacttc cccaccctga acctggacct taaggtggcc    720
cgcagcgtgc tgccactgtc ggtagtcttc attggcatga taagtttcaa taacctctgc    780
ctcaagtacg taggggtggc cttctacaac gtggggcgct cgctcaccac cgtgttcaat    840
gtgcttctgt cctacctgct gctcaaacag accacttcct tctatgccct gctcacatgt    900
ggcatcatca ttggtggttt ctggctgggt atagaccaag agggagctga gggcacccTG    960
tccctcatag gcaccatctt cggggtgctg ccagcctct gcgtctccct caatgccatc     1020
tataccaaga aggtgctccc agcagtggac aacagcatct ggcgcctaac cttctataac    1080
aatgtcaatg cctgtgtgct cttcttgccc ctgatggttc tgctgggtga gctccgtgcc    1140
ctccttgact tgctcatct gtacagtgcc cacttctggc tcatgatgac gctgggtggc    1200
ctcttcggct ttgccattgg ctatgtgaca ggactgcaga tcaaattcac cagtcccctg    1260
acccacaatg tatcaggcac agccaaggcc tgtgcgcaga cagtgctggc cgtgctctac    1320
tatgaagaga ctaagagctt cctgtggtgg acaagcaacc tgatggtgct gggtggctcc    1380
tcagcctata cctgggtcag gggctgggag atgcagaaga cccaagagga ccccagctcc    1440
aaagagggtg agaagagtgc tattgggggtg tgagcttctt cagggacctg ggactgaacc    1500
caagtggggc ctacacagca ctgaaggctt cccatggagc tagccagtgt ggccctgagc    1560
aatactgttt acatcctcct tggaatatga tctaagagga gccagggtct ttcctggtaa    1620
tgtcagaaag ctgccaaatc tcctgtctgc cccatcttgt tttgggaaaa cccaccagg    1680 aatggcaccc ctacctgcct cctcctagag cctgtctacc tccatatcat ctctggggtt    1740
gggaccagct gcagccttaa ggggctggat tgatgaagtg atgtcttcta cacaagggag    1800
atgggttgtg atcccactaa ttgaagggat ttgggtgacc ccacacctct gggatccagg    1860
gcaggtagag tagtagctta ggtgctatta acatcaggaa cacctcagcc tgcctttgaa    1920
gggaagtggg agcttggcca agggaggaaa tggccattct gccctcttca gtgtggatga    1980
gtatggcaga cctgttcatg gcagctgcac cctggggtgg ctgataagaa aacattcacc    2040
```

-continued

```
tctgcatttc atatttgcag ctctagaacg ggggagagcc acacatcttt tacgggttaa    2100
gtagggtgat gagctcctcc gcagtcccta accccagttt tacctgcctg gcttcccttg    2160
gcccagctac ctagctgtac tccctttctg tactcttctc ttctccgtca tggcctcccc    2220
caacacctcc atctgcaggc aggaagtgga gtccacttgt aacctctgtt cccatgacag    2280
agccctttga atacctgaac ccctcatgac agtaagagac atttatgttc tctggggctg    2340
gggctgaagg agcccactgg ttctcactta gcctatctgg ctcctgtcac aaaaaaaaaa    2400
aaaaaaaaaa aaaaaaaact cgag                                           2424

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 16
tgcagatcgc gctggtggtc tc                                               22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 17
gctccttctt ggtctatacc                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 18
agaccacttc cttctatgcc                                                  20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 19
gcccctgacc caggtgtagg c                                                21
```